United States Patent
Zhang et al.

(10) Patent No.: US 10,378,010 B2
(45) Date of Patent: Aug. 13, 2019

(54) METHODS AND SYSTEMS FOR CONSTRUCTION OF NORMALIZED NUCLEIC ACID LIBRARIES

(71) Applicant: ILLUMINA, INC., San Diego, CA (US)

(72) Inventors: Zhihong Zhang, San Diego, CA (US); Yangbin Gao, San Diego, CA (US); Allen E. Eckhardt, San Diego, CA (US); Petr Capek, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 17 days.

(21) Appl. No.: 15/481,401

(22) Filed: Apr. 6, 2017

(65) Prior Publication Data

US 2017/0292124 A1    Oct. 12, 2017

Related U.S. Application Data

(60) Provisional application No. 62/319,746, filed on Apr. 7, 2016, provisional application No. 62/348,766, filed on Jun. 10, 2016.

(51) Int. Cl.
*C12Q 1/68* (2018.01)
*C12N 15/10* (2006.01)
(Continued)

(52) U.S. Cl.
CPC ....... *C12N 15/1075* (2013.01); *C12Q 1/6806* (2013.01); *C12Q 1/686* (2013.01);
(Continued)

(58) Field of Classification Search
None
See application file for complete search history.

(56) References Cited

U.S. PATENT DOCUMENTS

| 5,223,414 A | 6/1993 | Zarling et al. |
| 6,565,727 B1 | 5/2003 | Shenderov |

(Continued)

FOREIGN PATENT DOCUMENTS

| WO | WO 2002/080822 | 10/2002 |
| WO | WO 2007/120241 | 10/2007 |

(Continued)

OTHER PUBLICATIONS

2014/0322716 A1.*

(Continued)

*Primary Examiner* — Aaron A Priest
(74) *Attorney, Agent, or Firm* — Knobbe, Martens, Olson & Bear LLP

(57) ABSTRACT

The present disclosure generally relates to nucleic acid amplification systems and methods suitable for construction of nucleic acid samples, including construction of normalized nucleic acid libraries. In some embodiments, the method includes providing one or more input nucleic acid samples, contacting each of the input nucleic acid samples (e.g., input library) with a reaction mixture including first amplification or normalization primers and second amplification or normalization primers, wherein the first amplification or normalization primers are immobilized on a solid support and the second amplification or normalization primers are in solution phase, and amplifying the input nucleic acid samples under conditions such that substantially all of the first amplification or normalization primers are incorporated into amplification products. Further provided are systems and droplet actuator devices that are configured to carry out the methods disclosed herein. Compositions that include nucleic acid samples and libraries, preferably normalized, prepared in accordance with the disclosed methods and systems are also provided.

24 Claims, 39 Drawing Sheets

(51) Int. Cl.
*C12Q 1/6806* (2018.01)
*C12Q 1/686* (2018.01)
*C12Q 1/6874* (2018.01)
*C12Q 1/6844* (2018.01)
*B01L 3/00* (2006.01)

(52) U.S. Cl.
CPC ......... *C12Q 1/6844* (2013.01); *C12Q 1/6874* (2013.01); *B01L 3/502792* (2013.01)

(56) References Cited

U.S. PATENT DOCUMENTS

| | | |
|---|---|---|
| 6,773,566 B2 | 8/2004 | Shenderov |
| 6,911,132 B2 | 6/2005 | Pamula et al. |
| 6,977,033 B2 | 12/2005 | Becker et al. |
| 7,052,244 B2 | 5/2006 | Fouillet et al. |
| 7,163,612 B2 | 1/2007 | Sterling et al. |
| 7,211,414 B2 | 5/2007 | Hardin et al. |
| 7,315,019 B2 | 1/2008 | Turner et al. |
| 7,328,979 B2 | 2/2008 | Decre et al. |
| 7,329,492 B2 | 2/2008 | Hardin et al. |
| 7,329,860 B2 | 2/2008 | Feng et al. |
| 7,399,590 B2 | 7/2008 | Piepenburg et al. |
| 7,405,281 B2 | 7/2008 | Xu et al. |
| 7,439,014 B2 | 10/2008 | Pamula et al. |
| 7,547,380 B2 | 6/2009 | Velev |
| 7,641,779 B2 | 1/2010 | Becker et al. |
| 7,727,466 B2 | 6/2010 | Meathrel et al. |
| 7,829,284 B2 | 11/2010 | Kong et al. |
| 8,039,817 B2 | 10/2011 | Feng et al. |
| 8,241,573 B2 | 8/2012 | Banerjee et al. |
| 2003/0132538 A1 | 7/2003 | Chandler |
| 2003/0205632 A1 | 11/2003 | Kim et al. |
| 2005/0118574 A1 | 6/2005 | Chandler et al. |
| 2005/0175996 A1* | 8/2005 | Chen ............... C12Q 1/6806 435/6.11 |
| 2005/0179746 A1 | 8/2005 | Roux et al. |
| 2005/0191686 A1 | 9/2005 | Han et al. |
| 2005/0260686 A1 | 11/2005 | Watkins et al. |
| 2005/0277197 A1 | 12/2005 | Chandler et al. |
| 2006/0039823 A1 | 2/2006 | Yamakawa et al. |
| 2006/0159962 A1 | 7/2006 | Chandler et al. |
| 2006/0164490 A1 | 7/2006 | Kim et al. |
| 2006/0194331 A1 | 8/2006 | Pamula et al. |
| 2007/0023292 A1 | 2/2007 | Kim et al. |
| 2007/0064990 A1 | 3/2007 | Roth |
| 2007/0207513 A1 | 9/2007 | Sorensen et al. |
| 2008/0003571 A1* | 1/2008 | McKernan ............ B82Y 15/00 435/6.12 |
| 2008/0009420 A1* | 1/2008 | Schroth ............... C12Q 1/6848 506/16 |
| 2008/0053205 A1 | 3/2008 | Pollack et al. |
| 2008/0108082 A1 | 5/2008 | Rank et al. |
| 2008/0124252 A1 | 5/2008 | Marchand et al. |
| 2008/0151240 A1 | 6/2008 | Roth |
| 2008/0283414 A1 | 11/2008 | Monroe et al. |
| 2008/0305481 A1 | 12/2008 | Whitman et al. |
| 2009/0192044 A1 | 7/2009 | Fouillet et al. |
| 2009/0272914 A1 | 11/2009 | Feng et al. |
| 2009/0283407 A1 | 11/2009 | Shah et al. |
| 2009/0321262 A1 | 12/2009 | Adachi et al. |
| 2010/0096266 A1 | 4/2010 | Kim et al. |
| 2010/0194408 A1 | 8/2010 | Sturmer et al. |
| 2011/0048951 A1 | 3/2011 | Wu |
| 2011/0118132 A1 | 5/2011 | Winger et al. |
| 2012/0270305 A1 | 10/2012 | Reed et al. |
| 2013/0338042 A1 | 12/2013 | Shen et al. |
| 2014/0141436 A1* | 5/2014 | Erlich et al. ......... C12Q 1/6881 435/6.12 |
| 2014/0322716 A1* | 10/2014 | Robins ................ C12Q 1/6846 435/6.12 |
| 2015/0133310 A1* | 5/2015 | Hayden ................ C12Q 1/6844 506/2 |

FOREIGN PATENT DOCUMENTS

| | | |
|---|---|---|
| WO | WO 2007/133710 | 11/2007 |
| WO | WO 2007/147063 | 12/2007 |
| WO | WO 2008/042067 | 4/2008 |
| WO | WO 2008/101194 | 8/2008 |
| WO | WO 2008/116221 | 9/2008 |
| WO | WO 2008/134153 | 11/2008 |
| WO | WO 2008/098236 | 1/2009 |
| WO | WO 2009/021173 | 2/2009 |
| WO | WO 2009/115335 | 9/2009 |
| WO | WO 2010/027894 | 6/2010 |
| WO | WO 2011/002957 | 1/2011 |
| WO | WO 2013/117595 | 8/2013 |
| WO | WO 2013/131962 | 9/2013 |

OTHER PUBLICATIONS

Blomquist et al., Targeted RNA-Sequencing with Competitive Multiplex-PCR Amplicon Libraries, PLoS One. 2013; 8(11): e79120, Published online Nov. 13, 2013.*

Sint et al., Advances in multiplex PCR: balancing primer efficiencies and improving detection success, Methods Ecol Evol. Oct. 2012;3(5):898-905.*

Kane et al., Application of less primer method to multiplex PCR, International Congress Series 1288 (2006) 694-696.*

Ma et al., Isothermal amplification method for next-generation sequencing, Proc Natl Acad Sci U S A. Aug. 27, 2013; 110(35): 14320-14323, Published online Aug. 12, 2013.*

Dhindsa, Virtual Electrowetting Channels: Electronic Liquid Transport with Continuous Channel Functionality, Lab Chip, 2010, 10:832-836.

International Search Report and Written Opinion dated May 31, 2107 for International Application No. PCT/US2017/026169 filed Apr. 5, 2017.

* cited by examiner

METHODS AND SYSTEMS FOR CONSTRUCTION OF NORMALIZED NUCLEIC ACID LIBRARIES

RELATED APPLICATIONS

This application claims priority to U.S. Provisional Patent Application Ser. No. 62/319,746, filed on Apr. 7, 2016, and U.S. Provisional Patent Application Ser. No. 62/348,766, filed on Jun. 10, 2016, each of which is hereby expressly incorporated by reference in its entirety.

FIELD

This disclosure relates generally to the field of production and normalization of nucleic acid libraries, and particularly relates to devices, systems and methods for preparation of normalized nucleic acid libraries suitable for various downstream analytical applications such as nucleic acid sequencing, particularly next generation sequencing.

BACKGROUND

The materials described in this section are not admitted to be prior art by inclusion in this section.

As common practice, biological samples used to prepare nucleic acid libraries for downstream analyses are homogeneously processed according to standardized assay protocols without regard to customized procedures for each sample. An important quality control (QC) measurement is nucleic acid concentration of nucleic acid libraries since performance of many modern nucleic acid analysis technologies is dependent on the nucleic acid concentration of input nucleic acids. Since such downstream analyses typically use expensive reagents and incur significant costs to perform, samples not meeting nucleic acid concentration requirements and/or other QC measurements are simply discarded on the assumption that the sample preparation was intrinsically unsuitable for the desired application.

For example, in next-generation sequencing (NGS) applications, also known as high-throughput sequencing, it is often desirable but logistically challenging to prepare nucleic acid libraries with substantially uniform DNA molar concentrations. This problem often arises in the preparation of nucleic acid libraries constructed from a plurality of heterogeneous biological samples, particularly when a desirable source biological sample is disproportionately underrepresented. This problem additionally arises when a target nucleic acid molecule is a relatively rarer and/or more unstable nucleic acid species when compared to even other nucleic acids that are derived from the same biological sample.

SUMMARY

This section provides a general summary of the disclosure, and is not comprehensive of its full scope or all of its features.

The present disclosure generally relates to systems and methods for amplification and/or normalization of nucleic acids that can be performed on individual nucleic acid samples or libraries in order to generate a master pool of nucleic acid libraries having customized molar concentrations of target nucleic acid molecules. In some embodiments, the disclosed methods allow for generating nucleic acid libraries having substantially uniform concentrations across multiple nucleic acid libraries. In some embodiments, the disclosed systems and methods allow for preparation of targeted amplicon samples or libraries on a droplet actuator using a digital fluidic, e.g. microfluidic, procedure.

A droplet actuator as described herein typically includes one or more substrates configured to form a surface or gap for conducting droplet operations. The one or more substrates establish a droplet operations surface or gap for conducting droplet operations and may also include electrodes arranged to conduct the droplet operations. The droplet operation substrate or the gap between the substrates may be coated or filled with a filler fluid that is immiscible with the liquid that forms the droplets.

Droplet actuators are used in a variety of applications in which precise and accurate handling of small volumes of liquid samples and reagents are required for achieving reliable analytical results. For example, droplet actuators are used to conduct a variety of molecular protocols, such as amplification of nucleic acids (e.g., polymerase chain reaction (PCR)). In one exemplary application, PCR techniques are used in the preparation of targeted amplicon samples or libraries for sequencing. On-bench protocols (e.g., plate-based protocols) have been developed for preparation of targeted amplicon samples or libraries. However, on-bench protocols typically involve multiple labor and time intensive steps (e.g., pipetting, reagent preparation, etc.) and relatively large sample input amounts. In addition, the quality of sequence data and subsequent data analysis depends on the quality of amplicon sample or library construction. Therefore, there is a need for a flexible, automated platform for construction of nucleic acid samples or libraries that provides high yield, uniformity, and specificity across multiple samples and/or libraries from relatively low DNA inputs, with less reagent consumption, and allows a user to operate over a range of multiplexed operations.

In one aspect, disclosed herein are embodiments of methods for nucleic acid amplification that include (a) providing a nucleic acid sample including target nucleic acid molecules; (b) contacting the nucleic acid sample with a reaction mixture comprising a solid phase and a liquid phase, where the solid phase includes a plurality of first amplification primers immobilized on a solid support, the first amplification primers capable of specifically hybridizing to a first sequence of the target nucleic acid molecules, and where the liquid phase includes a plurality of second amplification primers in solution, the plurality of second primers capable of specifically hybridizing to a second sequence of the target nucleic acid molecules; and (c) amplifying the target nucleic acid molecules under isothermal conditions such that substantially all of the first amplification primers are incorporated into amplification products, wherein the plurality of first primers is provided in an amount which limits the yield of amplification products to a predefined amount, and the plurality of second amplification primers is provided in an amount that exceeds the amount of the first amplification primers.

Implementations of embodiments of the methods according to this aspect and other aspects of the disclosure can include one or more of the following features. In some embodiments, the plurality of second amplification primers is provided in an amount within an order of magnitude of the amount of first amplification primer. In some embodiments, the plurality of second amplification primers is provided in an amount that exceeds the amount of the first amplification primers by at least 100%. In some embodiments, the methods further include separating the amplification products from the solid support. In some embodiments, the solid support includes a plurality of beads. In some embodiments, the solid support includes beads selected from magnetic beads, paramagnetic beads, plastic beads, polystyrene beads, glass beads, agarose beads, flow cytometry microbeads, polystyrene microparticles, polystyrene nanoparticles, functionalized polystyrene microparticles, functionalized polystyrene nanoparticles, coated polystyrene microparticles, coated polystyrene nanoparticles, silica microbeads, fluorescent microspheres, fluorescent nanospheres, functionalized fluorescent microspheres, functionalized fluorescent nanospheres, coated fluorescent microspheres, coated fluorescent nanospheres, color dyed microparticles, color dyed nanoparticles, magnetic microparticles, magnetic nanoparticles, superparamagnetic microparticles, superparamagnetic nanoparticles, and combinations thereof. In some embodiments, the beads are in an aqueous reaction buffer. In some embodiments, the beads are in fluid communication with each other. In some embodiments, the beads include streptavidin beads onto which the first amplification primers are affixed through conjugated biotin. In some embodiments, the beads are monoclonal. In some embodiments, the beads are polyclonal. In some embodiments, the solid support is a surface of a reaction site. In some embodiments, the surface of a reaction site includes a bottom portion of an inner surface of a well, a groove, a flow cell, a reaction chamber or channel.

Some embodiments disclosed herein relate to methods for nucleic acid amplification in which the nucleic acid sample includes single-stranded nucleic acid molecules. Some embodiments disclosed herein relate to methods for nucleic acid amplification in which the nucleic acid sample includes double-stranded nucleic acid molecules.

In some embodiments of the methods for nucleic acid amplification disclosed herein, the first amplification primers and the second amplification primers includes sequences complementary to known nucleotide sequences within the target nucleic acid molecules. In some embodiments, the known nucleotide sequences correspond to the first ends and second ends of the target nucleic acid molecules. In some embodiments, the first ends and second ends of the target nucleic acid molecules include universal sequencing tail-adaptors that have been added to the target nucleic acid molecules. In some embodiments, each of the first and/or second amplification primers further includes an indexing portion. In some embodiments, at least a portion of the first amplification primers further includes a capture portion having sequence complementarity to a region of the target nucleic acid molecules in addition to a known sequence of the target nucleic acid molecules. In some embodiments, the capture portion is generated by hybridizing a capture oligonucleotide to a first amplification primer immobilized onto the solid support and extending the immobilized amplification primer to generate an extended amplification primer having sequence complementarity to the capture oligonucleotide.

In some embodiments of the methods for nucleic amplification disclosed herein, the amplification step is performed on a plurality of nucleic acid samples. In some embodiments, the amount of each of the plurality of nucleic acid samples is not normalized across the plurality of nucleic acid samples. In some embodiments, the plurality of nucleic acid samples is combined before the amplification step. In some embodiments, the amplification products from the plurality of nucleic acid samples are combined to form a nucleic acid pooled library. In some embodiments, the amplification products from the plurality of nucleic acid samples are combined before being separated from the respective solid support. In some embodiments, the amplification products from the plurality of nucleic acid samples are combined after being separated from the respective solid support.

Some embodiments of the methods disclosed herein further include a step of obtaining a nucleotide sequence of the amplification products. In some embodiments, the nucleotide sequence of the amplification products is obtained by nucleic acid sequencing. In some embodiments, the nucleic acid sequencing includes high-throughput sequencing, e.g. next generation sequencing (NGS).

In some embodiments, the present disclosure provides methods for nucleic acid amplification that include (a) providing a nucleic acid sample including target nucleic acid molecules; (b) contacting the nucleic acid sample with a reaction mixture comprising a solid phase and a liquid phase, where the solid phase includes a plurality of first amplification primers immobilized on a solid support, the first amplification primers capable of specifically hybridizing to a first sequence of the target nucleic acid molecules, and where the liquid phase includes a plurality of second amplification primers in solution, the plurality of second primers capable of specifically hybridizing to a second sequence of the target nucleic acid molecules; and (c) amplifying the target nucleic acid molecules under isothermal conditions such that substantially all of the first amplification primers are incorporated into amplification products, wherein the plurality of first primers is provided in an amount which limits the yield of amplification products to a predefined amount, and where at least a portion of the first amplification primers further comprises a capture portion having sequence complementarity to a region of the target nucleic acid molecules in addition to a known sequences of the target nucleic acid molecules, and the capture portion is generated by hybridizing a capture oligonucleotide to a first amplification primer immobilized onto the solid support and extending the immobilized amplification primer to generate an extended amplification primer having sequence complementarity to the capture oligonucleotide. In some embodiments of the methods disclosed herein, the reaction mixture further comprises one or more of a recombinase, a single-strand DNA-binding protein, a helicase, and a strand-displacing polymerase. Further provided are compositions that include amplification products produced by a method according to this aspect and other aspects of the disclosure.

In one aspect, disclosed herein are embodiments of methods for nucleic acid amplification and/or normalization that include (a) providing an input nucleic acid sample including target nucleic acid molecules; (b) contacting the input nucleic acid sample with a reaction mixture comprising a plurality of first normalization primers and a plurality of second normalization primers, where the plurality of first normalization primers immobilized on a solid support, the first normalization primers capable of specifically hybridizing to a first sequence of the target nucleic acid molecules, and where the plurality of second normalization primers in solution, the plurality of second primers capable of specifically hybridizing to a second sequence of the target nucleic acid molecules; and (c) amplifying the target nucleic acid molecules under isothermal conditions such that substantially all of the first normalization primers are incorporated into amplification products, wherein the plurality of first primers is provided in an amount which limits the yield of amplification products to a predefined amount, and the plurality of second normalization primers is provided in an amount that exceeds the amount of the first normalization primers.

Implementations of embodiments of the methods according to the disclosure can include one or more of the following features. In some embodiments, the plurality of second normalization primers is provided in an amount within an order of magnitude of the amount of first normalization primer. In some embodiments, the plurality of second normalization primers is provided in an amount that exceeds the amount of the first normalization primers by at least 100%. In some embodiments, the methods further include separating the amplification products from the solid support. In some embodiments, the plurality of first normalization primers is hybridized with the target nucleic acid molecules prior to being immobilized on the solid support. In some embodiments, the plurality of first normalization primers is immobilized on the solid support prior to being hybridized with the target nucleic acid molecules. In some embodiments, the solid support includes a plurality of beads. In some embodiments, the solid support includes beads selected from magnetic beads, paramagnetic beads, magnetically responsive beads, plastic beads, polystyrene beads, glass beads, agarose beads, and combinations thereof. In some embodiments, the solid support includes beads selected from magnetic beads, paramagnetic beads, plastic beads, polystyrene beads, glass beads, agarose beads, flow cytometry microbeads, polystyrene microparticles, polystyrene nanoparticles, functionalized polystyrene microparticles, functionalized polystyrene nanoparticles, coated polystyrene microparticles, coated polystyrene nanoparticles, silica microbeads, fluorescent microspheres, fluorescent nanospheres, functionalized fluorescent microspheres, functionalized fluorescent nanospheres, coated fluorescent microspheres, coated fluorescent nanospheres, color dyed microparticles, color dyed nanoparticles, magnetic microparticles, magnetic nanoparticles, superparamagnetic microparticles, superparamagnetic nanoparticles, and combinations thereof. In some embodiments, the beads are in an aqueous reaction buffer. In some embodiments, the beads are in fluid communication with each other. In some embodiments, the beads include streptavidin beads onto which the first normalization primers are affixed through conjugated biotin. In some embodiments, the beads are monoclonal. In some embodiments, the beads are polyclonal. In some embodiments, the solid support is a surface of a reaction site. In some embodiments, the surface of a reaction site includes a bottom portion of an inner surface of a well, a groove, a flow cell, a reaction chamber or channel.

Some embodiments disclosed herein relate to methods for nucleic acid amplification and/or normalization in which the input nucleic acid sample includes single-stranded nucleic acid molecules. Some embodiments disclosed herein relate to methods for nucleic acid amplification in which the input nucleic acid sample includes double-stranded nucleic acid molecules. In some embodiments, the input nucleic acid sample includes a mixture of single-stranded nucleic acids and double stranded nucleic acids.

In some embodiments of the methods for nucleic acid amplification and/or normalization disclosed herein, at least one of the first normalization primers and/or the second normalization primers includes a region having sequence complementarity to known nucleotide sequences within the target nucleic acid molecules. In some embodiments, the known nucleotide sequences correspond to the first ends and second ends of the target nucleic acid molecules. In some embodiments, the first ends and second ends of the target nucleic acid molecules include universal primer regions that have been added to the target nucleic acid molecules. In some embodiments, the universal primer regions include a sequencing-by-synthesis (SBS) primer sequence. In some embodiments, at least one of the first and/or second normalization primers further includes an indexing portion. In some embodiments, at least one of the first and/or second normalization primers further includes a region having sequence complementarity to the universal primer regions added to the target nucleic acid molecules. In some embodiments, at least a portion of the first normalization primers further comprises a capture portion having sequence complementarity to a cognate region of the target nucleic acid molecules in addition of a known sequence of the target nucleic acid molecules. In some embodiments, the capture portion is generated by hybridizing a capture oligonucleotide to a first normalization primer and extending the first normalization primer to generate an extended normalization primer having sequence complementarity to the capture oligonucleotide.

In some embodiments of the methods for nucleic acid amplification and/or normalization disclosed herein, the normalizing amplification step is performed on a plurality of input nucleic acid samples. In some embodiments, the amount of each of the input nucleic acid samples is not equalized across the plurality of input nucleic acid samples. In some embodiments, the plurality of input nucleic acid samples is combined before the amplification step. In some embodiments, the amplification products from the plurality of input nucleic acid samples are combined to form a nucleic acid pooled nucleic acid library. In some embodiments, the amplification products from the plurality of input nucleic acid samples are combined before being separated from the respective solid support. In some embodiments, the amplification products from the plurality of input nucleic acid samples are combined after being separated from the respective solid support.

Some embodiments of the methods disclosed herein further include a step of obtaining a nucleotide sequence of the amplification products. In some embodiments, the nucleotide sequence of the amplification products is obtained by nucleic acid sequencing. In In some embodiments, the nucleic acid sequencing includes high-throughput sequencing, e.g., next generation sequencing (NGS).

In some embodiments, the present disclosure provides methods for nucleic acid amplification that include (a) providing an input nucleic acid sample including target nucleic acid molecules; (b) contacting the input nucleic acid sample with a reaction mixture comprising plurality of first normalization primers and a plurality of second normalization primers, where the plurality of first normalization primers is immobilized on a solid support, the first normalization primers capable of specifically hybridizing to a first sequence of the target nucleic acid molecules, and where the plurality of second normalization primers is in solution, the plurality of second primers capable of specifically hybridizing to a second sequence of the target nucleic acid molecules; and (c) amplifying the target nucleic acid molecules under isothermal conditions such that substantially all of the first normalization primers are incorporated into amplification products, wherein the plurality of first primers is provided in an amount which limits the yield of amplification products to a predefined amount, and where at least a portion of the first normalization primers further comprises a capture portion having sequence complementarity to a region of the target nucleic acid molecules in addition to a known sequences of the target nucleic acid molecules, and the capture portion is generated by hybridizing a capture oligonucleotide to a first normalization primer and extending the first normalization primer to generate an extended normalization primer having sequence complementarity to the capture oligonucleotide.

In some embodiments of the methods disclosed herein, the reaction mixture further comprises one or more of a recombinase, a single-strand DNA-binding protein, a helicase, and a strand-displacing polymerase.

In some embodiments of the methods according to this aspect and other aspects of the present disclosure, prior to step (a), the target nucleic acid molecules in the input nucleic acid sample are subjected to a first enrichment amplification reaction which includes a first target-specific primer and a second target-specific primer. In some embodiments, each of the first target-specific primer and the second target-specific primer includes a region having sequence complementarity to known sequences of the target nucleic acid molecules. In some embodiments, each of the first target-specific primer and the second target-specific primer includes a universal primer region. In some embodiments, the universal primer region of the first target-specific primer includes a sequencing-by-synthesis (SBS) primer sequence.

In some embodiments of the methods disclosed herein, prior to step (a), the target nucleic acid molecules in the input nucleic acid sample are subjected to a second enrichment amplification reaction which includes a first universal primer and a second universal primer, wherein the first universal primer includes a region having sequence complementarity to the universal primer region of the first target-specific primer, and the second universal primer includes a region having sequence complementarity to the universal primer region of the second target-specific primer. In some embodiments, each of the first and/or second universal primers further includes an indexing portion.

In some embodiments, the method for nucleic acid amplification as disclosed herein is performed in multiplexed format. In some embodiments, the method disclosed herein is performed in multiplexed format on a droplet actuator.

In on aspect, some embodiments disclosed herein relate to a method for multiplexed amplification of nucleic acid samples on a droplet actuator, the method including: (a) providing a plurality of input nucleic acid samples including target nucleic acid molecules; (b) loading the plurality of input nucleic acid samples onto a droplet operations surface of the droplet actuator having droplet operations electrodes arranged thereon; (c) dispending a normalization reagent droplet comprising a plurality of first normalization primers and a plurality of second normalization primers, wherein (i) the plurality of first normalization primers is immobilized on a solid support and capable of specifically hybridizing to a first sequence of the target nucleic acid molecules, (ii) the plurality of second normalization primers is in solution and capable of specifically hybridizing to a second sequence of the target nucleic acid molecules; and (d) amplifying the target nucleic acid molecules under isothermal conditions such that substantially all of the first normalization primers are incorporated into amplification products. In some embodiments, the method of this aspect and other aspects further includes, prior to step (c), dispensing a first enrichment PCR reagent droplet onto a droplet operations surface of the droplet actuator, wherein the first enrichment PCR reagent droplet including a first target-specific primer and a second target-specific primer; and thermally cycling the target nucleic acid molecules in the plurality of input nucleic acid samples to form enriched nucleic acid samples. In some embodiments, each of the first target-specific primer and/or the second target-specific primer includes a region having sequence complementarity to known sequences of the target nucleic acid molecules. In some embodiments, each of the first target-specific primer and/or the second target-specific primer further includes a universal primer region. In some embodiments, the universal primer region of the first target-specific primer includes a sequencing-by-synthesis (SBS) primer sequence. In some embodiments, at least one of the first and/or second target-specific primers further includes an indexing portion.

In some embodiments, the method of this aspect and other aspects further includes, prior to step (c), dispensing a second enrichment PCR reagent droplet onto a droplet operations surface of the droplet actuator, wherein the second enrichment PCR reagent droplet comprising a first universal primer and a second universal primer; and thermally cycling the target nucleic acid molecules in the plurality of input nucleic acid samples to form enriched nucleic acid samples. In some embodiments, at least one of the first and/or second universal primers further includes a primer sequence region. In some embodiments, at least one of the first and/or second universal primers further includes an indexing portion.

In some embodiments, the method of this aspect and other aspects further includes, prior to step (c), dispensing a first enrichment PCR reagent droplet onto a droplet operations surface of the droplet actuator, wherein the first enrichment PCR reagent droplet including a first target-specific primer and a second target-specific primer; dispensing a second enrichment PCR reagent droplet onto a droplet operations surface of the droplet actuator, wherein the second enrichment PCR reagent droplet including a first universal primer and a second universal primer; combining the second enrichment PCR reagent droplet with the first enrichment PCR reagent droplet using droplet operations to form a combined enrichment PCR reagent droplet; and thermally cycling the target nucleic acid molecules in the plurality of input nucleic acid samples to form enriched nucleic acid samples.

In one aspect, some embodiments disclosed herein relate to a microfluidic system for performing multiplexed amplification of nucleic acid samples on a droplet actuator, in which the microfluidic system includes a processor for executing code, a memory communicatively coupled to the processor, and a program code stored in the memory that causes the processor to execute a method of multiplexed amplification of nucleic acid samples, wherein the method comprising (a) loading a plurality of input nucleic acid samples onto a droplet operations surface of the droplet actuator having droplet operations electrodes arranged thereon, each of the plurality of input nucleic acid samples comprising target nucleic molecules; (b) dispensing a normalization reagent droplet comprising a plurality of first normalization primers and a plurality of second normalization primers, wherein the plurality of first normalization primers is immobilized on a solid support and capable of specifically hybridizing to a first sequence of the target nucleic acid molecules, and the plurality of second normalization primers is in solution and capable of specifically hybridizing to a second sequence of the target nucleic acid molecules; and (c) amplifying the target nucleic acid molecules under isothermal conditions such that substantially all of the first normalization primers are incorporated into amplification products.

In various embodiments of the disclosure, implementations of the microfluidic system disclosed herein can include one or more of the following components: (a) a heating device; (b) a droplet actuator thermally coupled to the heating device; (c) a detector optically coupled to the droplet actuator; (d) an impedance sensing module; (e) a disruption device for lysing a biomaterial comprising nucleic acids; and a controller that is electronically coupled to one or more of the components of (a) to (d). In some embodiments, the controller of the microfluidic system disclosed herein includes a program code, a processor for executing the program code, and a local memory in communication with the processor, wherein the program code causes the processor to execute a method of multiplexed amplification of nucleic acid samples, the method including (a) loading a plurality of input nucleic acid samples onto a droplet operations surface of the droplet actuator having droplet operations electrodes arranged thereon, each of the plurality of input nucleic acid samples comprising target nucleic molecules; (b) dispensing a normalization reagent droplet including a plurality of first normalization primers and a plurality of second normalization primers, wherein the plurality of first normalization primers is immobilized on a solid support and capable of specifically hybridizing to a first sequence of the target nucleic acid molecules, the plurality of second normalization primers is in solution and capable of specifically hybridizing to a second sequence of the target nucleic acid molecules; (c) amplifying the target nucleic acid molecules under isothermal conditions such that substantially all of the first normalization primers are incorporated into amplification products.

In some embodiments, the program code of the controller causes the processor to execute a method of multiplexed amplification of nucleic acid samples that further includes, prior to step (a), dispensing a first enrichment PCR reagent droplet onto a droplet operations surface of the droplet actuator, wherein the first enrichment PCR reagent droplet including a first target-specific primer and a second target-specific primer; and thermally cycling the target nucleic acid molecules in the plurality of input nucleic acid samples to form enriched nucleic acid samples. In some embodiments, the program code causes the processor to execute a method of multiplexed amplification of nucleic acid samples that further includes, prior to step (a), dispensing a second enrichment PCR reagent droplet onto a droplet operations surface of the droplet actuator, wherein the second enrichment PCR reagent droplet comprising a first universal primer and a second universal primer, and thermally cycling the target nucleic acid molecules in the plurality of input nucleic acid samples to form enriched nucleic acid samples. In some embodiments, the program code causes the processor to execute a method of multiplexed amplification of nucleic acid samples that further includes, prior to step (a), dispensing a first enrichment PCR reagent droplet onto a droplet operations surface of the droplet actuator, wherein the first enrichment PCR reagent droplet including a first target-specific primer and a second target-specific primer; dispensing a second enrichment PCR reagent droplet onto a droplet operations surface of the droplet actuator, wherein the second enrichment PCR reagent droplet including a first universal primer and a second universal primer; combining the second enrichment PCR reagent droplet with the first enrichment PCR reagent droplet using droplet operations to form a combined enrichment PCR reagent droplet; and thermally cycling the target nucleic acid molecules in the plurality of input nucleic acid samples to form enriched nucleic acid samples. In some embodiments, the microfluidic system disclosed herein further includes one or more magnets movable from and into proximity to one or more of the fluid reservoirs, wherein the positions of magnets are optionally controlled by a motor. In some embodiments, the microfluidic system disclosed herein further includes one or more heating devices to providing thermal control thereof.

In some embodiments, the program code is partially or entirely stored in a local memory of the controller or on a remote computing device. In some embodiments, the program code is locally and/or remotely executed.

In some embodiments, the droplet actuator of the microfluidic systems disclosed herein includes (a) a bottom substrate and a top substrate separated by a droplet operations gap, wherein either one or both of the bottom and the top substrate including electrodes configured for conducting droplet operations in the gap; (b) an electrode arrangement including one or more of paths, reaction lanes, and an array of droplet operations electrodes; (c) a plurality of fluid reservoirs interconnected through the electrode arrangement configured for dispensing separated fluids along the electrodes; and (d) a plurality of temperature control zones. In some embodiments, the droplet operations gap is filled with a filler fluid. In some embodiments, the filler fluid is a silicone oil fluid or a hexadecane filler fluid. In some embodiments, the plurality of fluid reservoirs includes one or more reagent reservoirs, one or more sample reservoirs, one or more index reservoirs, one or more waste reservoirs, or a combination thereof. In some embodiments, the droplet actuator further includes one or more biochemical reaction zones for performing certain processing steps for each nucleic acid amplification reaction. In some embodiments, at least one of the fluid reservoirs includes an input port for loading fluids therein. In some embodiments, the droplet actuator disclosed herein further includes one or more magnets movable from and into proximity to one or more of the droplet operations electrodes. In some embodiments, the magnets are permanent magnets. In some embodiments, the magnets are electromagnets. In some embodiments, the temperature control zones include differing temperature from one another. In some embodiments, the temperature control zones include essentially the same temperature. In some embodiments, the electrode arrangement in the droplet actuator disclosed herein includes one or more of dispensing operation electrodes, transporting operation electrodes, merging operation electrodes, incubating operation electrodes, splitting operation electrodes, mixing operation electrodes, or combinations thereof.

In one aspect, some embodiments disclosed herein relate to a computer readable medium storing processor executable instructions for performing a method of multiplexed nucleic acid amplification on a droplet actuator, the method including (a) loading the plurality of input nucleic acid samples onto a droplet operations surface of the droplet actuator having droplet operations electrodes arranged thereon, each of the plurality of input nucleic acid samples including target nucleic molecules; (b) dispensing a normalization reagent droplet including a plurality of first normalization primers and a plurality of second normalization primers, wherein the plurality of first normalization primers is immobilized on a solid support and capable of specifically hybridizing to a first sequence of the target nucleic acid molecules, the plurality of second normalization primers is in solution and capable of specifically hybridizing to a second sequence of the target nucleic acid molecules; (c) amplifying the target nucleic acid molecules under isothermal conditions such that substantially all of the first normalization primers are incorporated into amplification products.

Also provided, in one aspect of the disclosure, are compositions that include amplification products produced by a method or a system disclosed herein.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 11A: PCR efficiency per PCR cycle. FIG. 11B: Uniformity improvements.

DETAILED DESCRIPTION

Figure 1:
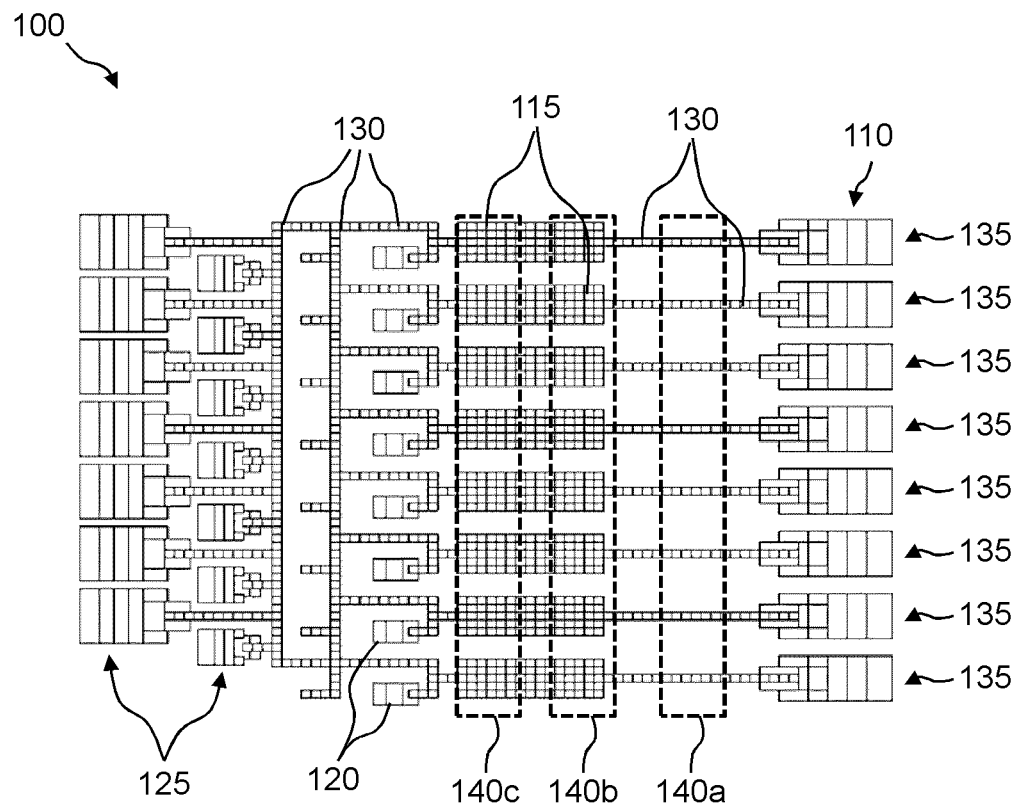
FIG. 1 illustrates a top view of an example of an electrode arrangement of a droplet actuator suitable for use in conducting a multiplexed targeted amplicon sample preparation protocol.

The present disclosure generally relates to nucleic acid amplification devices, systems, and methods including novel approaches suitable for construction of nucleic acid samples, including construction of amplified/normalized nucleic acid samples and libraries, optionally in customized fashion, for downstream analytical applications, including sequencing applications utilizing techniques such as next-generation sequencing (NGS) and related methodologies such as genotyping-by-sequencing (GBS). In some embodiments, the method includes contacting a plurality of input nucleic acid samples with a reaction mixture including first primers and second primers, wherein the first and second primers can be amplification primers or normalization primers depending on specific workflows. In some embodiments, the first amplification or normalization primers are immobilized on a solid support and the second amplification or normalization primers are in solution phase, and the amplification or normalization of the input nucleic acid samples is performed under conditions such that the amounts of nucleic acids in the resultant amplified/normalized samples are in substantially similar concentrations relative to one another regardless of the amounts of input samples. In some embodiments, substantially all of the first amplification or normalization primers are incorporated into amplification products. For example, in some embodiments at least 80%, at least 85%, at least 90%, at least 95%, at least 96%, at least 97%, at least 98%, at least 99%, 100%, or a range defined by any two of the preceding values, of the first amplification or normalization primers are incorporated into amplification products. Further provided are systems and droplet actuator devices that are configured to carry out the methods disclosed herein. Nucleic acid libraries prepared in accordance with the disclosed methods are also provided.

In one aspect, some embodiments of the disclosure relate to droplet actuator devices for and methods of preparing targeted amplicon samples or libraries for downstream analytical applications such as, for example, sequencing applications. Using digital microfluidics technology, the droplet actuator devices and methods of the disclosure provide automated liquid handling for amplification and selection of targeted regions of genomic DNA for processing into amplicon samples or libraries for downstream analytical applications, e.g. sequencing. In various embodiments, library construction parameters, such as DNA input (e.g., 1 ng or less), library yield and uniformity, time-to-result, and reagent consumption, are substantially improved over the existing state of the art.

In one aspect, some embodiments of the methods disclosed herein use a 2-stage amplification reaction, wherein a first amplification reaction is driven by target-specific primers and a second amplification reaction is driven by universal primers. The 2-stage amplification reaction allows for selection of reaction conditions (e.g., annealing and extension temperatures, incubation times, and number of PCR cycles) specific for each type of amplification, e.g., target-specific primer amplification or universal primer amplification, and provides for more efficient targeted amplification (e.g., improved library yield and uniformity).

In some embodiments, the targeted amplicons in the resulting nucleic acid samples or libraries are then enriched in a solution-based hybridization reaction using target-specific capture probes and then immobilized on capture beads for subsequent processing steps. In some embodiments of the methods disclosed herein, a solution-based hybridization reaction is generally more kinetically favorable compared to a solid-phase hybridization reaction, thereby creating a more robust system and providing for improved target capture, as well as improved uniformity and specificity across multiple samples and/or libraries.

In one aspect, some embodiments of the methods disclosed herein employ at least one set of first amplification or normalization primers in solution phase and at least another set of second amplification or normalization primers immobilized on a solid phase support during amplification or normalization of the nucleic acid library. This feature of this aspect of the disclosure advantageously differs from current library preparation procedures in which both primers are either in a solution phase or both primers are affixed onto a solid phase. Additionally, in some particular implementations of the methods disclosed herein, the set of first primers immobilized on the solid support is provided in an amount which limits the yield of amplification products to a predefined amount, and the set of second primers in solution is provided in an amount that exceeds the amount of the first primers. Advantages achieved by this specific primer configuration is twofold: (1) It allows conveniently washing away of any amplification products that is found in solution after amplification, resulting in an amplified/normalized amount of amplification products remained immobilized on the solid support which can be subsequently isolated, such that a predefined amount of amplification products can be generated. In contrast, existing library preparation methods typically produce excess amounts of amplification products, which are measured, and then subjected to a dilution step to obtain desired amounts is required; (2) in some particular implementations, the methods disclosed herein allow construction of a plurality of nucleic acid libraries in which the output DNA amounts are normalized to substantially uniform concentrations across the libraries regardless of the amounts of input DNA samples.

In one aspect, the methods of the disclosure use a kinetic exclusion amplification procedure, also referred to as exclusion amplification (ExAmp) reaction to equalize sample quantities and adjust the concentration of amplicon DNA for subsequent sequencing applications. In some embodiments, the ExAmp library normalization reaction is an isothermal amplification reaction that uses a first primer sequence (e.g., primer including a P7 primer sequence) immobilized on the capture beads and a second primer sequence (e.g., primer including a P5 primer sequence) in solution as normalization primers for library normalization. Generally, a process of library normalization can be performed over a wide range of PCR product (amplicon) inputs (e.g., those having over at least two orders of magnitude change of input). In addition, the reaction conditions (e.g., incubation time, P7 and/or P5 primer concentration, and reaction components) can be selected such that all available primers immobilized on the capture beads are extended into amplicons, e.g., the reaction is allowed to run to saturation.

In general, the flexibility and programmability of a droplet actuator device provides for precise control over the various biochemical reactions performed during construction of a targeted amplicon sample or library.

In one exemplified application, the droplet actuators and methods of the disclosure are used for preparation of a targeted amplicon sample or library for identification of genetic variants, e.g., single nucleotide polymorphisms (SNPs).

In the following detailed description, reference is made to the accompanying Figures, which form a part hereof. The illustrative embodiments described in the detailed description, Figures, and claims are not meant to be limiting. Other embodiments may be used, and other changes may be made, without departing from the spirit or scope of the subject matter presented here. It will be readily understood that the embodiments of the present disclosure, as generally described herein, and illustrated in the Figures, can be arranged, substituted, combined, and designed in a wide variety of different configurations, all of which are explicitly contemplated and make part of this disclosure.

Unless expressly defined otherwise, all terms of art, notations and other scientific terms or terminology used herein are intended to have the meanings commonly understood by those of skill in the art to which this disclosure pertains when read in light of this disclosure.

Some Definitions

Unless otherwise defined, all terms of art, notations and other scientific terms or terminology used herein are intended to have the meanings commonly understood by those of skill in the art to which this disclosure pertains when read in light of this disclosure. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a molecule" includes one or more molecules, including mixtures thereof. As used in this disclosure and the appended claims, the term "and/or" can be singular or inclusive. For example, "A and/or B" is used herein to include all of the following alternatives: "A", "B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The term "activate," as used herein with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed. For example, an electrode may be activated using an AC signal having a frequency from about 1 Hz to about 10 MHz, or from about 10 Hz to about 60 Hz, or from about 20 Hz to about 40 Hz, or about 30 Hz.

As used herein, the term "droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; non-limiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference.

In various embodiments of the disclosure, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., Nature 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Determination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et. al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. According to some of embodiments disclosed herein, a droplet may include one or more beads depending on specific workflows and/or downstream applications.

The term "droplet actuator," as used herein, means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference.

In some embodiments disclosed herein, certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the patents and applications referenced herein and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In some embodiments, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. In some embodiments disclosed herein where multiple substrates are used, a spacer may be provided between the substrates to determine the height of the gap therebetween and define on-actuator dispensing reservoirs. The spacer height may, for example, be at least about 5 µm, 100 µm, 200 µm, 250 µm, 275 µm or more. Alternatively or additionally the spacer height may be at most about 600 µm, 400 µm, 350 µm, 300 µm, or less. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component One or more reference electrodes may be provided on the base (or bottom) and/or top substrates and/or in the gap. Examples of reference electrode arrangements are provided in the patents and patent applications referenced herein. In various embodiments, the manipulation of droplets by a droplet actuator may be electrode mediated, e.g., electrowetting mediated or dielectrophoresis mediated or Coulombic force mediated.

Examples of other techniques for controlling droplet operations that may be used in the droplet actuators of the present disclosure include using devices that induce hydrodynamic fluidic pressure, such as those that operate on the basis of mechanical principles (e.g., external syringe pumps, pneumatic membrane pumps, vibrating membrane pumps, vacuum devices, centrifugal forces, piezoelectric/ultrasonic pumps and acoustic forces); electrical or magnetic principles (e.g., electroosmotic flow, electrokinetic pumps, ferrofluidic plugs, electrohydrodynamic pumps, attraction or repulsion using magnetic forces and magnetohydrodynamic pumps); thermodynamic principles (e.g., gas bubble generation/phase-change-induced volume expansion); other kinds of surface-wetting principles (e.g., electrowetting, and opto-electrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap).

Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc.), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference. In some embodiments disclosed herein, one or both substrates may be fabricated using a printed circuit board (PCB), glass, indium tin oxide (ITO)-coated glass, and/or semiconductor materials as the substrate. When the substrate is ITO-coated glass, the ITO coating is, for example, a thickness of at least about 20 nm, 50 nm, 75 nm, 100 nm or more. Alternatively or additionally, the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc., Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.).

Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers.

Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan.

Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

"Droplet operation", as used herein, means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For non-limiting examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In some embodiments disclosed herein, the electrode is operated in AC mode but is switched to DC mode for imaging. It is helpful for conducting droplet operations for the footprint area of droplet to be similar to electrowetting area; in other words, 1×-, 2×- 3×-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or non-conductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler fluids may be selected for compatibility with droplet actuator materials. As an example, fluorinated filler fluids may be usefully employed with fluorinated surface coatings. Fluorinated filler fluids are useful to reduce loss of lipophilic compounds, such as umbelliferone substrates like 6-hexadecanoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77), Galden HT200 (bp=200° C., viscosity=2.4 cSt, d=1.79), Galden HT230 (bp=230° C., viscosity=4.4 cSt, d=1.82) (all from Solvay Solexis); those in the Novec line, such as Novec 7500 (bp=128° C., viscosity=0.8 cSt, d=1.61), Fluorinert FC-40 (bp=155° C., viscosity=1.8 cSt, d=1.85), Fluorinert FC-43 (bp=174° C., viscosity=2.5 cSt, d=1.86) (both from 3M). In general, selection of perfluorinated filler fluids is based on kinematic viscosity (<7 cSt is preferred, but not required), and on boiling point (>150° C. is preferred, but not required, for use in DNA/RNA-based applications (PCR, etc.)). Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid.

The term "hybridization", as used herein, refers generally to the ability of nucleic acid molecules to join via complementary base strand pairing. Such hybridization may occur when nucleic acid molecules are contacted under appropriate conditions and/or circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, nucleic acid molecules are said to exhibit "complete complementarity" when every nucleotide of one of the molecules is complementary to its base pairing partner nucleotide of the other. Two molecules are said to be "minimally complementary" if they can hybridize to one another with sufficient stability to permit them to remain annealed to one another under at least conventional "low-stringency" conditions. In some instances, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional stringency conditions are described by Sambrook et al., *Molecular Cloning, A Laboratory Handbook*, Cold Spring Harbor Laboratory Press, 1989), and by Haymes et al. In: *Nucleic Acid Hybridization, A Practical Approach*, IRL Press, Washington, D.C. (1985), each of which is herein incorporated by reference in its entirety, and for the disclosure discussed herein. Departures from complete complementarity are therefore permissible in some embodiments, as long as such departures do not completely preclude the capacity of the molecules to form a double-stranded structure. Thus, in order for a nucleic acid molecule or fragment thereof of the present disclosure to serve as a primer or probe in some embodiments it needs only be sufficiently complementary in sequence to be able to form a stable double-stranded structure under the particular solvent and salt concentrations employed. In other embodiments, the nucleic acids disclosed herein are fully complementary to their targets.

The term "immobilize", as used herein with respect to magnetically responsive beads, means that the beads are substantially restrained in position in a droplet or in filler fluid on a droplet actuator. For example, in some embodiments disclosed herein, immobilized beads are sufficiently restrained in position in a droplet to permit execution of a droplet splitting operation, yielding one droplet with substantially all of the beads and one droplet substantially lacking in the beads. In reference to nucleic acid molecule, e.g. a primer or oligonucleotide, the term "immobilize," and its derivatives, as used herein refers to the attachment of a nucleic acid molecule directly to a solid support through at least one intermediate component such as, for example, biotin. As used herein, the terms "attach" and "affix" and their respective derivatives include adsorption, such as, physisorption or chemisorption, ligand/receptor interaction, covalent bonding, hydrogen bonding, or ionic bonding of a polymeric substance or a nucleic acid molecule to a solid support.

As used herein, the term "magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracr-RNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

"Reservoir" means an enclosure or partial enclosure configured for holding, storing, or supplying liquid. In some embodiments, a droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. In some embodiments, a system using an off-cartridge reservoir will typically include a fluid passage means whereby liquid may be transferred from the off-cartridge reservoir into an on-cartridge reservoir or into a droplet operations gap.

As used herein, the term a "nucleic acid sample" refers to a collection of nucleic acid molecules. In some embodiments, the nucleic acid sample is from a single biological source, e.g. one individual or one tissue sample, and in other embodiments the nucleic acid sample is a pooled sample, e.g., containing nucleic acids from more than one organism, individual or tissue.

The term nucleic acid sample encompasses "nucleic acid library" which, as used herein, includes a nucleic acid library that has been prepared by any method known in the art. In some embodiments, providing the nucleic acid library includes the steps required for preparing the library, for example, including the process of incorporating one or more nucleic acid samples into a vector-based collection, such as by ligation into a vector and transformation of a host. In some embodiments, providing a nucleic acid library includes the process of incorporating a nucleic acid sample into a non-vector-based collection, such as by ligation to adaptors. In some embodiments, the adaptors can anneal to PCR primers to facilitate amplification by PCR or can be universal primer regions such as, for example, sequencing tail adaptors. In some embodiments, the adaptors can be universal sequencing adaptors.

The term "substantially" as used herein has its ordinary meaning as read in light of the specification, and can mean, for example, at least 80%, at least 85%, at least 90%, at least 95%, at least 96%, at least 97%, at least 98%, at least 99%.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the present disclosure, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

As used herein, the term "universal sequence" refers to a region of sequence that is common to two or more nucleic acid molecules where the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus, a universal capture nucleic acid or a universal primer such as, a universal sequencing tail-adaptor, includes a sequence that can hybridize specifically to a universal sequence. In some embodiments of the methods disclosed herein, target nucleic acid molecules may be modified to attach universal adaptors, for example, at one or both ends of the different target sequences, for example by ligation or by amplification using primer-directed amplification.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," issued on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

The terms "fluidics cartridge," "digital fluidics cartridge," "droplet actuator," and "droplet actuator cartridge" as used throughout the description can be synonymous.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

In some embodiments of the methods or processes described herein, the steps can be carried out in any order, except when a temporal or operational sequence is explicitly recited. Furthermore, in some embodiments, the specified steps can be carried out concurrently unless explicit claim language recites that they be carried out separately. For example, in some embodiments a claimed step of doing X and a claimed step of doing Y can be conducted simultaneously within a single operation, and the resulting process will fall within the literal scope of the claimed process.

As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

Headings, e.g., (a), (b), (i) etc., are presented merely for ease of reading the specification and claims, and do not limit in any way the scope of the disclosure or its alternatives. The use of headings in the specification or claims does not require the steps or elements be performed in alphabetical or numerical order or the order in which they are presented.

I. Methods for Normalizing Nucleic Acid Samples

Various embodiments of the disclosure generally relate to systems and methods for construction of nucleic acid samples, including construction of amplified/normalized nucleic acid samples and nucleic acid libraries for downstream analytical applications. In one aspect, some embodiments of the methods disclosed herein employ at least one set of first amplification or normalization primers immobilized on a solid phase support and at least another set of second amplification or normalization primers in solution phase during normalization of the nucleic acid samples or nucleic acid libraries. As discussed above, this biphasic feature of the disclosed methods differs from current library preparation procedures in which both primers are either in a solution phase or both primers are affixed onto a solid phase. The first amplification or normalization primers in solution phase offer fast kinetics, while the second amplification or normalization primers immobilized on a solid phase support offer ability to normalize the nucleic acid samples and ease of purification. Additionally, in some particular implementations of the methods disclosed herein, the set of first primers immobilized on the solid support is provided in an amount which limits the yield of amplification products to a predefined amount, and the set of second primers in solution is provided in an amount that exceeds the amount of the first primers. In some embodiments, the primer configuration can provide one or more of the following advantages: (1) convenient washing away of any amplification products that is found in solution after amplification, resulting in an amplified/normalized amount of amplification products remained immobilized on the solid support which can be subsequently isolated, such that a predefined amount of amplification products can be generated; (2) construction of a plurality of nucleic acid samples or nucleic acid libraries in which the DNA amounts are normalized to substantially uniform concentrations across the nucleic acid libraries regardless of the amounts of input DNA in the original samples.

In one aspect, the present disclosure provides a method for nucleic acid amplification that includes providing a nucleic acid sample including target nucleic acid molecules; contacting the nucleic acid sample with a reaction mixture comprising a solid phase and a liquid phase, the solid phase includes a plurality of first amplification primers immobilized on a solid support, the first amplification primers capable of specifically hybridizing to a first sequence of the target nucleic acid molecules, and the liquid phase includes a plurality of second amplification primers in solution, the plurality of second primers capable of specifically hybridizing to a second sequence of the target nucleic acid molecules; and amplifying the target nucleic acid molecules under isothermal conditions such that substantially all of the first amplification primers are incorporated into amplification products, wherein the plurality of first primers is provided in an amount which limits the yield of amplification products to a predefined amount, and the plurality of second amplification primers is provided in an amount that exceeds the amount of the first amplification primers.

Figure 2:
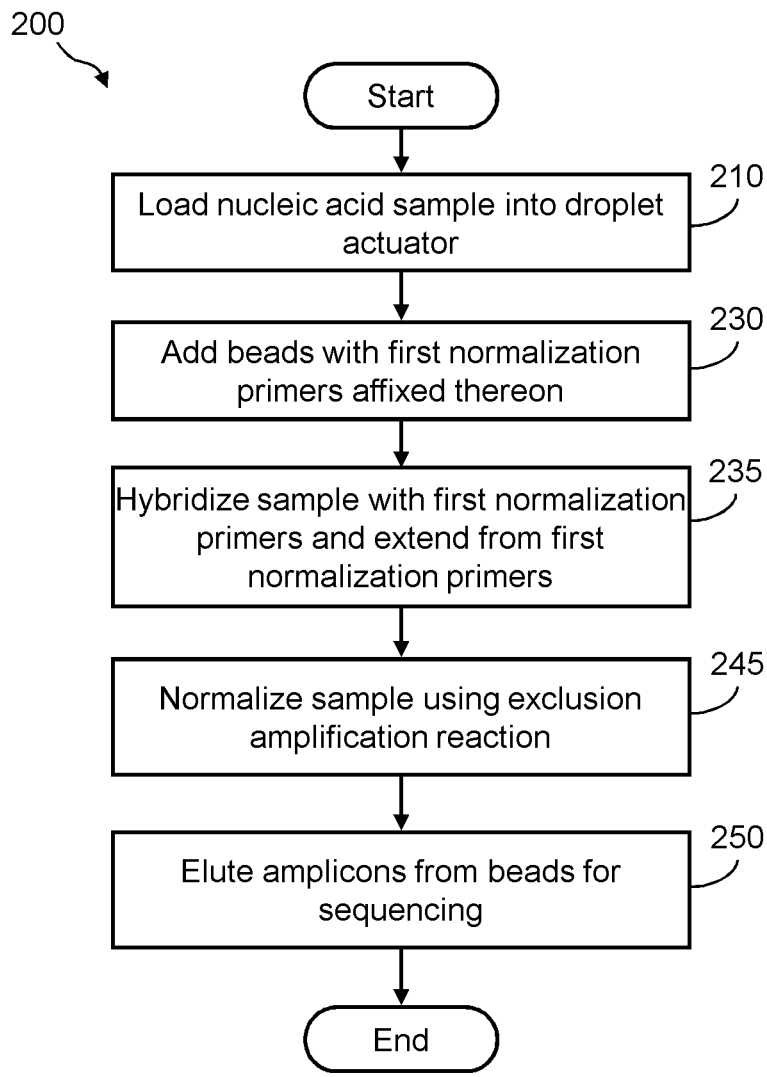
FIG. 2 illustrates a flow diagram of a non-limiting example of a method of nucleic acid amplification and normalization in accordance with some embodiments of the disclosure. The hybridization between target nucleic acid molecules and the first amplification or normalization primers takes place on a solid support. In this example, the solid support is a plurality of capture beads. Alternatively, the solid support can also be a surface of a reaction site.

FIG. 2 illustrates a flow diagram of a non-limiting example of a method of amplifying and/or normalizing nucleic acid sample according to some embodiments of the disclosure, in which the amount of target nucleic acid molecules in a nucleic acid sample is amplified/normalized in a reaction mixture that includes a solid phase and a liquid phase. Depending on specific workflows and downstream applications, extendable primers used in this and other exemplary methods of the present disclosure can be amplification primers or normalization primers. Method 200 may include, but is not limited to, the following steps.

At a step 210, an input nucleic acid sample such as, for example, a genomic DNA sample, comprising target nucleic acid molecules is provided. This step can be achieved, for example, by loading the nucleic acid sample into a sample reservoir of a droplet actuator. At a step 230, the target nucleic acid molecules are brought into contact with a reaction mixture comprising a solid phase and a liquid phase. The solid phase of the reaction mixture includes a plurality of first amplification or normalization primers (e.g., primers including a P7 primer sequence) capable of specifically hybridizing to a first sequence of the target nucleic acid molecules where the first amplification or normalization primers are immobilized on a solid support such as, for instance, capture beads. The liquid phase of the reaction mixture includes a plurality of second amplification or normalization primers in solution, the plurality of second primers capable of specifically hybridizing to a second sequence of the target nucleic acid molecules (e.g., primers including a P5 primer sequence). At a step 235, the first amplification or normalization primer hybridized to targeted nucleic acid sequences is extended to form an immobilized complementary DNA strand and, at a step 245, the extended target nucleic acid molecules are amplified under isothermal conditions such that substantially all of the first amplification or normalization primers are incorporated into amplification products. In some embodiments of the disclosed methods, the plurality of first immobilized primers is provided in an amount which limits the yield of amplification products to a predefined amount, and the plurality of second amplification or normalization primers is provided in an amount that exceeds the amount of the first amplification or normalization primers. At an optional step 250, the amplified/normalized nucleic acid samples are eluted from the capture beads for downstream analytical applications such as, for example, high-throughput sequencing.

Figure 3:
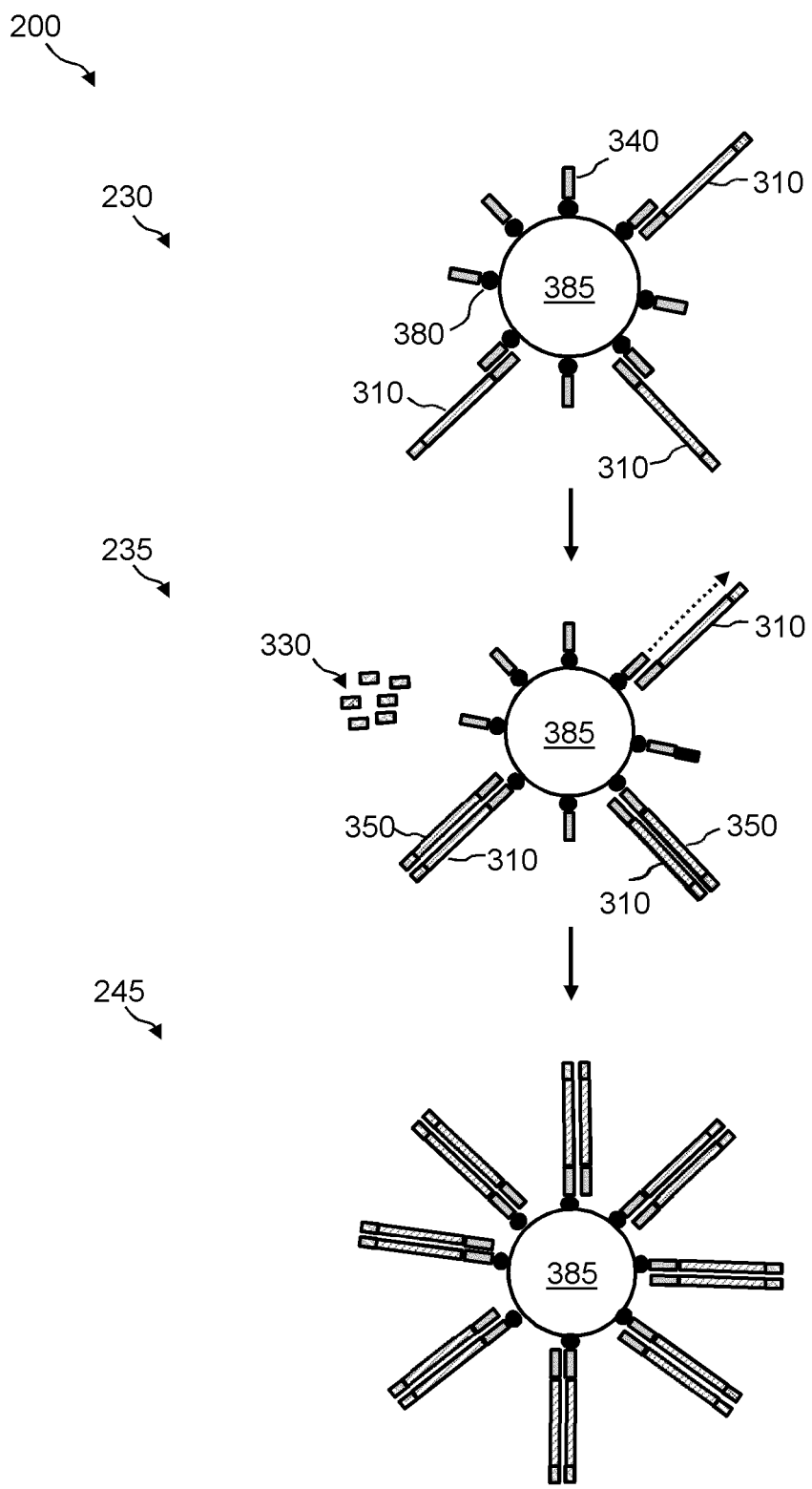
FIG. 3 shows pictorially the steps of the method of FIG. 2.

FIG. 3 shows pictorially the steps of method 200 of FIG. 2. Namely, an input nucleic acid sample (not shown) includes a target nucleic acid molecule 310. First amplification or normalization primer (e.g., reverse primer) includes a target-specific region 340. Second amplification or normalization primer (e.g., forward primer) includes a target-specific region 330. In some embodiments, the target-specific regions 330 and 340 flank a region of interest on the target nucleic acid molecule 310. In some embodiments, the target-specific regions can have sequence complementarity to adaptors or universal primer sequences in the target nucleic acids, which can be added to the target nucleic acids in a sequence specific manner. In some embodiments, as disclosed in more detail below, adaptors or universal primer sequences in the target nucleic acids can be added to the target nucleic acids in a sequence independent manner. An amplicon 350 is then synthesized using the forward primer and reverse primer. In the reaction, the first amplification or normalization primer (e.g., reverse primer) is immobilized on the solid support. For example, the reverse amplification or normalization primer is conjugated to a biotin label 380 and is immobilized on a streptavidin (SA) coated capture bead 385.

Figure 4:
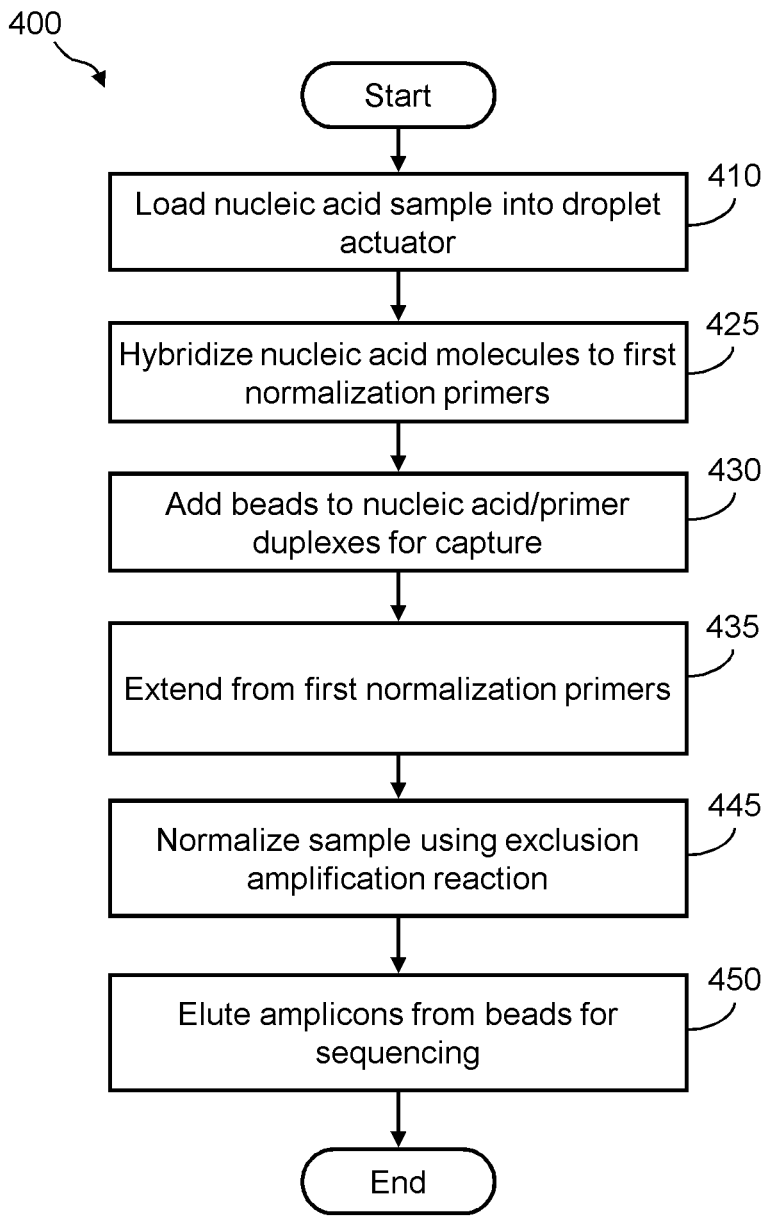
FIG. 4 depicts a flow diagram of another non-limiting example of a method of nucleic acid amplification and normalization as described herein, wherein the hybridization between target nucleic acid molecules and the first amplification or normalization primers takes place in solution phase.
Figure 5:
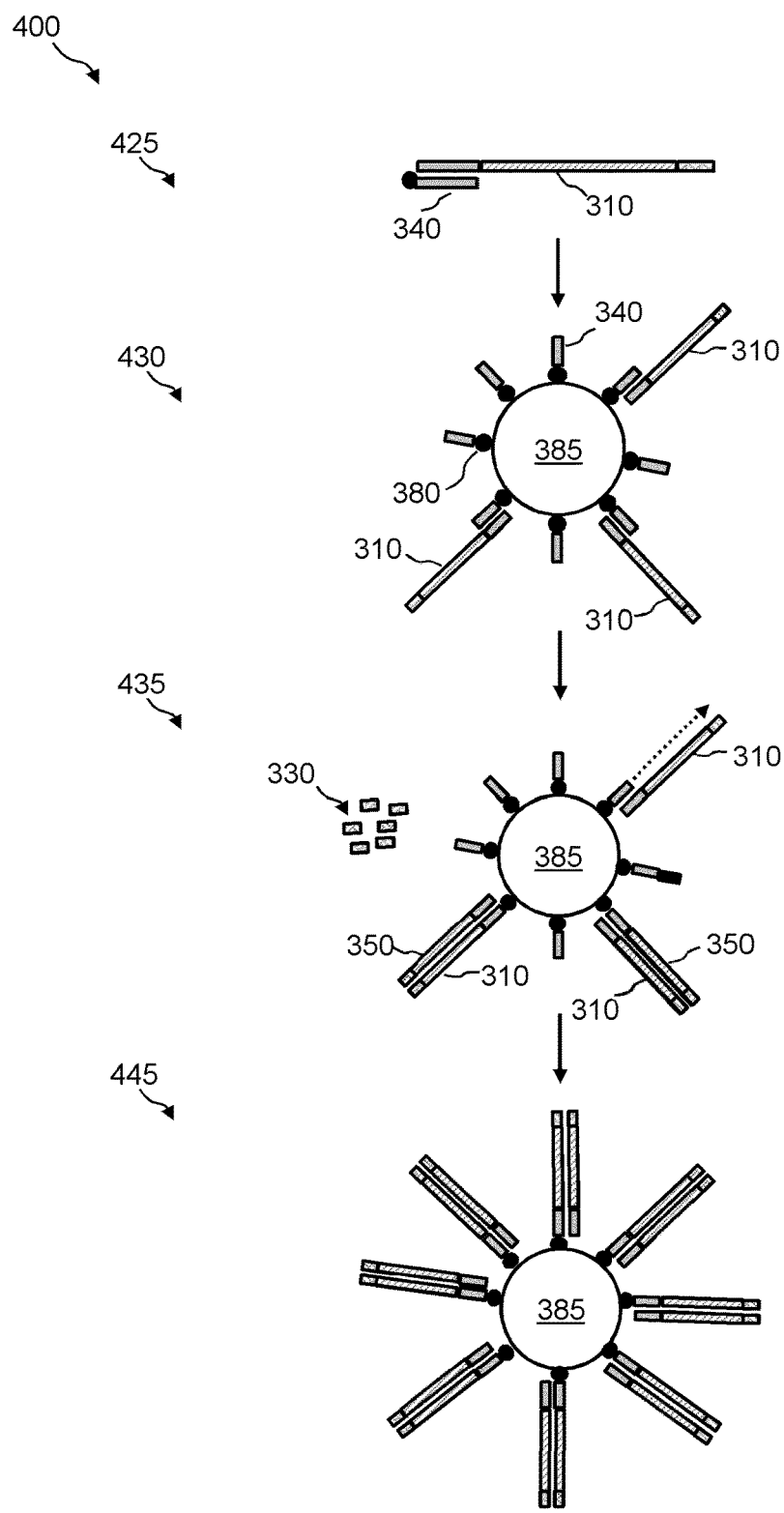
FIG. 5 shows pictorially the steps of the method of FIG. 4.

In some embodiments of the methods according to this and other aspects of the disclosure, the plurality of first amplification or normalization primers (e.g., reverse primers) is hybridized with the target nucleic acid molecules prior to being immobilized on the solid support. A flow diagram of a non-limiting example of a method according to these embodiments of the disclosure is shown at FIGS. 4 and 5. At a step 425, the first amplification or normalization primers 340 are hybridized to a target nucleic acid molecule 310 of the nucleic acid sample to form target molecule\normalization-primer duplexes. This hybridization step is carried out in solution phase. At a step 430, capture beads such as, for example, streptavidin-coated capture beads, are added to the hybridization reaction for capture of hybridized target molecule\primer duplexes. Hybridized molecule\normalization-primer duplexes and un-hybridized primers are immobilized on the capture beads by formation of a biotin-streptavidin binding complex. The remaining steps 435, 445, and 450 are carried out similarly to the corresponding steps 235, 245, and 250 of the exemplary methods described in FIGS. 2 and 3.

According to some embodiments of the methods disclosed herein, a sample or a library of target nucleic acids can have an average strand length that is desired or appropriate for a particular application of the methods or compositions set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for populations of target nucleic acids as disclosed herein can be in a range between a maximum and minimum value set forth above.

Solid Support

In some embodiments, the amplification and/or normalization reaction mixture of the methods disclosed herein includes one or more solid supports. Solid supports suitable for the methods disclosed herein can generally be of any convenient size and fabricated from any number of known materials. Preferably, the solid support used in the methods disclosed herein can be of any suitable type that provides a known binding capacity, resulting in a substantially unfluctuating amount of bound nucleic acids per fixed amount of solid support. Example of such materials include: inorganics, natural polymers, and synthetic polymers. Specific examples of these materials include: cellulose, cellulose derivatives, acrylic resins, glass, silica gels, gelatin, polystyrene, polyvinyl pyrrolidone, co-polymers of vinyl and acrylamide, polystyrene cross-linked with divinylbenzene or the like, polyacrylamides, latex gels, silicon, plastics, nitrocellulose, polystyrene, dextran, rubber, natural sponges, silica gels, control pore glass, metals, cross-linked dextrans (e.g., Sephadex™) agarose gel (Sepharose™), and other solid supports known to those of skill in the art.

In some embodiments, the solid phase supports can include synthetic polymer supports, such as polystyrene, polypropylene, substituted polystyrene (e.g., carboxylated or aminated polystyrene), polyamides, polyacrylamides, polyvinylchloride, and the like, or any material useful in nucleic acid affinity chromatography.

In some embodiments of the methods disclosed herein, the solid support can include beads. The term "bead," as used herein with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in Watkins et al., U.S. Patent Pub. No. 20050260686, entitled "Multiplex Flow Assays Preferably with Magnetic Particles as Solid Phase," published on Nov. 24, 2005; Chandler., U.S. Patent Pub. No. 20030132538, entitled "Encapsulation of Discrete Quanta of Fluorescent Particles," published on Jul. 17, 2003; Chandler et al., U.S. Patent Pub. No. 20050118574, entitled "Multiplexed Analysis of Clinical Specimens Apparatus and Method," published on Jun. 2, 2005; Chandler et al., U.S. Patent Pub. No. 20050277197, entitled "Microparticles with Multiple Fluorescent Signals and Methods of Using Same," published on Dec. 15, 2005; and Chandler et al., U.S. Patent Pub. No. 20060159962, entitled "Magnetic Microspheres for use in Fluorescence-based Applications," published on Jul. 20, 2006, the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target Examples of droplet actuator techniques for immobilizing magnetically responsive beads and/or non-magnetically responsive beads and/or conducting droplet operation protocols using beads are described in Pollack et al., U.S. Patent Pub. No. 20080053205, entitled "Droplet-Based Particle Sorting," published on Mar. 6, 2008; U.S. Patent App. No. 61/039,183, entitled "Multiplexing Bead Detection in a Single Droplet," filed on Mar. 25, 2008; Pamula et al., U.S. Patent App. No. 61/047,789, entitled "Droplet Actuator Devices and Droplet Operations Using Beads," filed on Apr. 25, 2008; U.S. Patent App. No. 61/086,183, entitled "Droplet Actuator Devices and Methods for Manipulating Beads," filed on Aug. 5, 2008; Eckhardt et al., International Patent Pub. No. WO/2008/098236, entitled "Droplet Actuator Devices and Methods Employing Magnetic Beads," published on Aug. 14, 2008; Grichko et al., International Patent Pub. No. WO/2008/134153, entitled "Bead-based Multiplexed Analytical Methods and Instrumentation," published on Nov. 6, 2008; Eckhardt et al., International Patent Pub. No. WO/2008/116221, "Bead Sorting on a Droplet Actuator," published on Sep. 25, 2008; and Eckhardt et al., International Patent Pub. No. WO/2007/120241, entitled "Droplet-based Biochemistry," published on Oct. 25, 2007, the entire disclosures of which are incorporated herein by reference. Bead characteristics may be employed in the multiplexing aspects of the present disclosure. Examples of beads having characteristics suitable for multiplexing, as well as methods of detecting and analyzing signals emitted from such beads, may be found in Whitman et al., U.S. Patent Pub. No. 20080305481, entitled "Systems and Methods for Multiplex Analysis of PCR in Real Time," published on Dec. 11, 2008; Roth, U.S. Patent Pub. No. 20080151240, "Methods and Systems for Dynamic Range Expansion," published on Jun. 26, 2008; Sorensen et al., U.S. Patent Pub. No. 20070207513, entitled "Methods, Products, and Kits for Identifying an Analyte in a Sample," published on Sep. 6, 2007; Roth, U.S. Patent Pub. No. 20070064990, entitled "Methods and Systems for Image Data Processing," published on Mar. 22, 2007; Chandler et al., U.S. Patent Pub. No. 20060159962, entitled "Magnetic Microspheres for use in Fluorescence-based Applications," published on Jul. 20, 2006; Chandler et al., U.S. Patent Pub. No. 20050277197, entitled "Microparticles with Multiple Fluorescent Signals and Methods of Using Same," published on Dec. 15, 2005; and Chandler et al., U.S. Patent Publication No. 20050118574, entitled "Multiplexed Analysis of Clinical Specimens Apparatus and Method," published on Jun. 2, 2005, the entire disclosures of which are incorporated herein by reference.

Accordingly, in some preferred embodiments, the beads suitable for the methods disclosed herein can be of any convenient size and fabricated from any number of known materials. In some embodiments, the bead can be, for example, magnetic beads, paramagnetic beads, plastic beads, polystyrene beads, glass beads, agarose beads, and combinations thereof. In some embodiments, the beads are beads approximately 2 to 100 μm in diameter, or 10 to 80 μm in diameter, or 20 to 40 μm in diameter. In some embodiments, the beads can be provided in solution. In some embodiments, the beads can be immobilized on a solid support. In some embodiments, the beads can be provided both in solution and in an immobilized state on a solid support.

In some preferred embodiment, the solid support can include streptavidin. In some embodiments, the solid support is, or can include, streptavidin-coated beads. In some embodiments, the solid support is or can include streptavidin-coated magnetic beads. In some embodiments where the solid phase support includes streptavidin, the nucleic acids molecules can be biotinylated to facilitate binding of the nucleic acids to the solid support.

In some embodiments of the methods disclosed herein, the solid phase support includes a surface of a reaction site. For example, a glass side can be treated to have nucleic acids bound at specific locations on the solid support, e.g., as a high density array. In some embodiments, the reaction site can include a bottom portion of an inner surface of a well, groove, flow cell, reaction chamber or channel. In some embodiments, the site can include a reaction chamber or well. In some embodiments, the reaction site can be part of an array of similar or identical sites. For example, the solid support can be the bottom and/or sides of a well on a microtiter plate.

In some embodiments of the methods disclosed herein, the beads or reactions sites are in an aqueous phase such as, for example, in aqueous reaction buffer. In some embodiments, the beads or reactions sites are in continuous aqueous phase. In some embodiments, the amplifying is performed without sealing the beads or reaction sites from each other. For example, the beads or reaction sites can remain in fluid communication with each other during the amplifying. Accordingly, in some embodiments of the methods disclosed herein, the beads or reaction sites are in fluid communication with each other during the amplifying. In other embodiments, the solid support or beads can be located in discrete locations that are separated from each other and not in fluid communication, e.g., wells of a microtiter plate, or beads located in wells of a microtiter plate.

In some embodiments, the amplification or normalization reaction mixture of the methods disclosed herein include one or more solid supports with amplification or normalization primers affixed thereon. Amplification or normalization primers can be attached to the solid support by methods well known to those of skill in the art. At least one of the supports can include one or more instances of a first primer including a first primer sequence. In some embodiments, at least one polynucleotide template in the reaction mixture (e.g., a member of a nucleic acid sample or nucleic acid library) includes a first primer binding sequence. The first primer binding sequence can be fully or substantially identical, or fully or substantially complementary, to the first primer sequence. In some embodiments, at least one, some or all of the solid supports include a plurality of first primers that are identical to each other. In some embodiments, all of the primers on the solid supports are identical to each other, or all include an identical first primer sequence. In a preferred embodiment, the solid support is a plurality of beads, wherein each bead in the plurality has a plurality of identical primers attached.

In various embodiments of the disclosure, a second amplification or normalization primer is provided in solution phase, which can be optionally exposed to the immobilized first amplification or normalization primer. In some embodiments, the amount of the second amplification or normalization primers in solution phase is greater than the amount of the first amplification or normalization primers immobilized on a solid phase support. By providing an excess amount of the second primer in solution, the amount of first primer immobilized on the solid support will determine the amount of amplification product produced on the solid support. Consequently the amplification results in a substantially constant amount of amplification products per fixed amount of solid phase support. In some embodiments, the plurality of second amplification or normalization primers is provided in an amount within an order of magnitude of the amount of first amplification or normalization primer. In some embodiments, the plurality of second amplification or normalization primers is provided in an amount that exceeds the amount of the first amplification or normalization primers by at least, or at least about, 100%. In other embodiments, the amount of the second primer exceeds the amount of the first primer by at least, or at least about, 150%, at least, or at least about 200%, at least, or at least about 300%, at least, or at least about 400%, or at least, or at least about 1000%, or a range of any two of the proceeding values, for example from about 100% to about 1000%.

Output Amplified/Normalized Samples and Libraries

In some embodiments, the amount of amplification products obtained from each nucleic acid sample can be substantially uniformly represented in a pooled nucleic acid library. In some other embodiments, the amounts of amplification products obtained from the input nucleic acid samples can be present in a pooled library in different, predetermined concentrations by obtaining the amplification products from different, predetermined amounts of solid support or by pooling different amounts of the amplification products.

Accordingly, in some embodiments, the methods disclosed herein allow for generating nucleic acid libraries having normalized amounts and which amounts are substantially uniform across multiple nucleic acid samples and/or libraries. In some embodiments, the nucleic acid amounts in the normalized nucleic acid libraries vary by less than 10%, 5%, 3%, 2%, or 1%. In some embodiments, the methods disclosed herein allow for generating pooled nucleic acid libraries in which the amount of constituent nucleic acids in the resultant pooled nucleic acid libraries are at substantially similar amounts regardless of the amount of input DNA samples. In some embodiments, the amounts of constituent nucleic acids in the pooled nucleic acid libraries vary by less than 10%, 5%, 3%, 2%, or 1%.

In some embodiments, the nucleic acid libraries or pooled libraries generated by the methods described herein can be suitable for downstream analytical applications, including sequencing application utilizing techniques such as next-generation sequencing (NGS) and related methodologies such as genotyping-by-sequencing (GBS).

In some embodiments, the nucleic acid amplification methods disclosed herein can be automated and/or can be performed in a multiplexed format, for example the methods can be performed by a droplet actuator or liquid handling robot.

In some embodiments of the disclosed methods and systems, the beads as described herein can be monoclonal, that is, they can include a single population of amplification or normalization primers that are identical to each other.

In some embodiments, the beads can be polyclonal, that is, they can include a pool of a plurality of monoclonal beads, wherein the pooled monoclonal beads include amplification or normalization primers comprising more than one capture portion having sequence similarity to a cognate region of a target nucleic acid. In some embodiments, the beads can include individual polyclonal beads, that is, they can include amplification or normalization primers comprising more than one capture portion per bead.

In some embodiments, at least one solid support includes two or more different primers affixed thereto. In some embodiments, the at least one support can include at least 2, 3, 4, 5, 6, 7, 8, 9, or 10 different amplification or normalization primers having different nucleic acid sequences. In some embodiments, the solid support has a plurality of discrete locations, each location having a plurality of primers having the same sequence. In some embodiments, the sequences at each of the plurality of locations is the same, in other embodiments the sequences at one or more of the plurality of locations differ from that of one or more other locations.

In some embodiments, the nucleic acid amplification methods disclosed herein further include a step of separating the amplification products from the solid support. Generally, any suitable method for removing nucleic acids from the solid support can be used. In some embodiments, the amplification products are separated from the solid support by elution. In some embodiments, the amplification products are eluted in a heated buffer. In some embodiments where streptavidin is included in solid phase support and the nucleic acids are biotinylated to facilitate binding of the nucleic acids to the solid support, the nucleic acid amplification products can be separated from the solid support via by heat avidin-biotin cleavage.

Input Nucleic Acid Samples

In some embodiments of the methods and systems disclosed herein, the input nucleic acid sample includes single-stranded nucleic acid molecules. In some embodiments, at least one of the target nucleic acid molecules in the input nucleic acid sample is double-stranded, or is rendered at least partly double-stranded using appropriate procedures prior to amplification. In some embodiments, the input nucleic acid sample includes a mixture of single-stranded nucleic acid molecules and double-stranded nucleic acid molecules. In some embodiments, the target nucleic acid molecules can be linear. Alternatively, the target nucleic acid molecules can be circular, or include a combination of linear and circular regions.

In some embodiments, the double stranded target nucleic acid molecules can include a forward strand. In some embodiments, the double stranded target nucleic acid molecules can further include a reverse strand. The forward strand, in some embodiments of the disclosed methods, can include a first primer binding site. The reverse strand, in some embodiments of the disclosed methods, can include a second primer binding site.

In various embodiments of the disclosure, the amount of input nucleic acid can be from about 0.01 ng to 100 ng. In some embodiments, the amount of input nucleic acid is about 0.1 ng, 0.2 ng, 0.3 ng, 0.4 ng, 0.5 ng, 0.6 ng, 0.7 ng, 0.8 ng, 0.9 ng, 1 ng, 1.1 ng, 1.2 ng, 1.3 ng, 1.5 ng, 2.0 ng, 2.5 ng, 3.0 ng, 3.5 ng, 4.0 ng, 4.5 ng, 5.0 ng, or within a range defined by any two of the aforementioned values. In some embodiments, the amount of input nucleic acid is about 5.5 ng, 6.0 ng, 6.5 ng, 7.0 ng, 7.5 ng, 8.0 ng, 8.5 ng, 9.0 ng, 9.5 ng, 10.0 ng, 11.0 ng, 11.5 ng, 12.0 ng, 12.5 ng, 13.0 ng, 13.5 ng, 14.0 ng, 15.0 ng, 15.5 ng, 16.0 ng, 16.5 ng, 17.0 ng, 18.0 ng, 18.5 ng, 19.0 ng, 19.5 ng, 20.0 ng, or within a range defined by any two of the aforementioned values. In some embodiments, the amount of input nucleic acid is about 21.0 ng, 22.0 ng, 22.5 ng, 23.0 ng, 23.5 ng, 24.0 ng, 24.5 ng, 25.0 ng, 26.0 ng, 27.0 ng, 28.0 ng, 29.0 ng, 30.0 ng, 32.5 ng, 35.0 ng, 37.5 ng, 40.0 ng, 42.5 ng, 45.0 ng, 47.5 ng, 50.0 ng, 52.5 ng, 55.0 ng, 60.0 ng, 65.0 ng, 70.0 ng, 75.0 ng, 80.0 ng, 85.0 ng, 90.0 ng, or within a range defined by any two of the aforementioned values. In some embodiments, the amount of input nucleic acid is about 0.08, 0.4, 2.0, 10.0, or 50.0 ng.

In some embodiments of the methods disclosed herein, the target nucleic acid molecules already include a first and/or second primer binding site prior to the amplification step(s). Alternatively, the target nucleic acid molecules do not originally include a primer binding site, and the disclosed methods optionally include attaching or introducing a primer binding site to the target nucleic acid molecules prior to the amplifying. For example, in some embodiments, the disclosed methods can optionally include ligating or otherwise introducing (e.g., by primer directed amplification, including PCR) an adaptor containing a primer binding site to, or into, the target nucleic acid molecules. The adapter can be ligated or otherwise introduced to an end of a linear target nucleic acid molecule, or within the body of a linear or circular nucleic acid molecule. In some embodiments, the target nucleic acid molecule can be circularized after the adapter is ligated or introduced. In some embodiments, a first adapter can be ligated or introduced at a first end of a linear target nucleic acid molecule, and a second adaptor can be ligated or introduced at a second end of the target nucleic acid molecule.

In some embodiments, the first amplification or normalization primers and the second amplification or normalization primers are complementary to binding sites with known nucleotide sequences within the target nucleic acid molecules. In some embodiments, the primer binding sites with known nucleotide sequences correspond to the first ends and second ends of the target nucleic acid molecules.

In some embodiments of the nucleic acid amplification methods disclosed herein, the first ends and second ends of the target nucleic acid molecules include universal primer regions such as, for example, universal sequencing tail adaptors, that have been added to the target nucleic acid molecules.

In some embodiments, at least one of the first and/or second amplification or normalization primers further includes an indexing portion. The indexing portion can be used to identify the source of the target nucleic acids, e.g., the individual or biological sample, such that if amplification products are pooled, the source of the target nucleic acids can later be determined. Alternatively, the indexing portion can be added to the target nucleic acids prior to the normalization step, for example, when adaptors or universal primer sequences are added to the target nucleic acids.

In some embodiments, at least a portion of the first amplification or normalization primers further includes a capture portion having sequence complementarity to a cognate region of the target nucleic acid molecules in addition to a known sequences of the target nucleic acid molecules. For example, if adaptors and/or universal primers are added to the nucleic acid molecules of the input sample, the adaptors and/or universal primers can constitute the "known sequences," while the "capture portion" is complementary to a sequence native to the nucleic acids in the library. In this way, only those portions of the library having the capture sequence will be amplified even though the adaptors and/or universal primers are present on most or all of nucleic acids of the library. In a preferred embodiment, the use of a capture portion permits selective amplification of nucleic acids in the nucleic acid sample, e.g., the nucleic acid library. Embodiments using capture probes are illustrated in FIGS. 6-9, described in more detail below.

In some embodiments, the capture portion is generated by hybridizing a capture oligonucleotide to a first amplification or normalization primer immobilized onto the solid support and extending the immobilized amplification or normalization primer to generate an extended amplification or normalization primer having sequence complementarity to the capture oligonucleotide.

Applicant has demonstrated that the method disclosed herein can be advantageously applied to a single nucleic acid sample or a plurality of nucleic acid samples by using a plurality of solid phase supports. Accordingly, in some embodiments of methods disclosed herein, the amplification step is performed on a plurality of nucleic acid libraries. In some embodiments, the amplification products from the plurality of nucleic acid libraries are combined to form a combined pooled nucleic acid library. In some embodiments, the amplification products derived from the plurality of nucleic acid libraries are combined after being removed from the solid phase support. In some embodiments, the amplification products from the plurality of nucleic acid libraries are combined before being removed from the solid phase support. In some embodiments, the plurality of input nucleic acid samples is combined before the amplification step. In some embodiments, the amount of each input nucleic acid sample is not normalized across the plurality of nucleic acid samples.

In some embodiments, the plurality of input nucleic acid samples comprises at least 2, 4, 8, 12, 24, 48, 96, 200, 384, 400, 500, 100, 1500, or a number of input nucleic acid samples within a range defined by any two of the aforementioned numbers.

In some embodiments, the relative representation of each population of constituent amplification products can be advantageously adjusted in the pooled nucleic acid library. By "advantageously adjusted", as used herein, is meant that the amount of each constituent amplification products in the pooled nucleic acid library can be controlled or predetermined. In some preferred embodiments, the amount of each constituent amplification products is substantially uniformly represented in the pooled nucleic acid library. Alternatively, the plurality of constituent amplification products can be present in the pooled nucleic acid library in different, predetermined concentrations. This may be achieved by assembling different amounts of the solid phase supports with amplification products remaining affixed thereon or by pooling different amounts of the plurality of constituent amplification products after being recovered from the solid phase support. Stated differently, the advantageous adjustment can include selectively adjusting both the proportional representation and the population number of constituent amplification products in the pooled nucleic acid library. In yet some further embodiments, an advantageous adjustment may include subjecting a sample of constituent amplification products to at least one processing step in addition to recovering amplification products from the solid phase support.

Normalization Step

In some embodiments of the methods disclosed herein, nucleic acid amplification is performed under substantially isothermal conditions. The optimal temperature for amplification varies and may for example depend on primer characteristics, such as sequence length, melting temperature as described elsewhere herein, and choice of polymerase. In some embodiments of the present disclosure, the amplification temperature is lower than 60 degrees Celsius, lower than 50 degrees Celsius, lower than 45 degrees Celsius, or lower than 42, 38, 35, 30, 25, or 20 degrees Celsius. In some preferred embodiments, the amplification temperature is 38 degrees Celsius.

In one aspect, the methods of the disclosure include isothermal amplification which can be performed by using, for example, kinetic exclusion amplification (KEA), also referred to as exclusion amplification (Ex-Amp). In some embodiments, the methods of the disclosure use an ExAmp normalization reaction to equalize sample quantities and adjust the concentration of amplicon DNA for subsequent sequencing applications. In some embodiments, the ExAmp library normalization reaction is an isothermal amplification reaction that uses a first normalization primer sequence (e.g., P7 primer sequence) immobilized on the capture beads and a second normalization primer sequence (e.g., P5 primer sequence) in solution as normalization primers for library normalization. Library normalization can be performed over a wide range of PCR product (amplicon) input (e.g., over at least two orders of magnitude change of input). The reaction conditions (e.g., incubation time, P7 and/or P5 primer concentration, and reaction components) can be selected such that all available primers on the capture beads are extended into amplicons, e.g., the reaction is run to saturation.

Accordingly, an amplified/normalized nucleic acid library of the present disclosure can be constructed using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature (e.g., bead) that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

In some embodiments, kinetic exclusion can occur when a process occurs at a sufficiently rapid rate to effectively exclude another event or process from occurring. Take for example a solution of beads having universal primers where the beads are randomly seeded with target nucleic acids in a solution and copies of the target nucleic acid are generated in an amplification process to fill each of the beads to capacity. In accordance with the kinetic exclusion methods of the present disclosure, the seeding and amplification processes can proceed simultaneously under conditions where the amplification rate exceeds the seeding rate. As such, the relatively rapid rate at which copies are made on a particular bead that has been seeded by a first target nucleic acid will effectively exclude a second nucleic acid from seeding that particular bead for amplification. Kinetic exclusion amplification methods can be performed as described in detail in the disclosure of U.S. Application Pub. No. 2013/0338042, which is incorporated herein by reference in its entirety.

Kinetic exclusion can exploit a relatively slow rate for initiating amplification (e.g., a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g., relatively slow diffusion or transport) vs. the relatively rapid rate at which amplification occurs to fill the site (e.g., bead or other site on a solid substrate (e.g., reaction site or well)) with copies of the nucleic acid seed. In another exemplary embodiment, kinetic exclusion can occur due to a delay in the formation of a first copy of a target nucleic acid that has seeded a site (e.g., delayed or slow activation) vs. the relatively rapid rate at which subsequent copies are made to fill the site. In this example, an individual site may have been seeded with several different target nucleic acids (e.g., several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site (e.g., bead) may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g., via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. No. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g., via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. No. 7,399,590 and 7,829,284, each of which is incorporated herein by reference.

In some embodiments of the methods disclosed herein, the amplification reagents used in the methods disclosed herein can further include one or more origin binding proteins. Without being bound by any particular theory, the inclusion of an origin binding protein in the amplification reaction facilitates amplicon formation and, in some case increases the rate of amplicon formation.

In some embodiments of the methods disclosed herein, the amplification reagents used in the methods disclosed herein can further include one or more a polymerase. In some embodiments, the polymerase can be a strand-displacing polymerase such as a Bst polymerase, a polD polymerase, a 9° N polymerase or phi29 polymerase. In some embodiments, the polymerase is a thermostable polymerase. In some embodiments, the template is RNA and the polymerase can be a reverse transcriptase.

Maintenance of sample representation (or specificity) is of critical importance to many library preparation methods because libraries used in several downstream analytical applications, such as next generation sequencing, should meet several requirements. For example, for many cDNA library applications (e.g., search for differentially expressed genes), it is essential to minimize the distortion of cDNA representation in a library with respect to initial mRNA. Stated differently, the content of individual cDNAs in the library, in some downstream applications, must be proportional to the copy number of the initial RNAs. In contrast, for some other applications, the concentrations of different individual cDNAs in a library must be equalized. Applicant has demonstrated that by using the methods described herein, the complexity of the input DNA library could be faithfully maintained, including the DNA species-to-species ratio, and possible minor allele frequency calls, with no observed difference other than the amount of the library being amplified and normalized. See, for example, Examples 13 and 14 below.

II. Methods for Multiplexed Preparation of Targeted Amplicon Libraries

On-bench protocols for targeted gene amplification and construction of a genomic amplicon library for sequencing can be adapted and described as discrete step-by-step, droplet-based protocols. Protocol steps are performed in aqueous droplets within an oil-filled droplet operations gap of a droplet actuator. Samples and assay reagents are manipulated as discrete droplets upon an arrangement of electrodes (e.g., electrode arrangement 100 of FIG. 1). Sample droplets and reagent droplets for use in conducting the various protocol steps may be dispensed and/or combined according to appropriate assay protocols using droplet operations on a droplet actuator. Incubation and washing of assay droplets, including temperature adjustments as needed, may also be performed on a droplet actuator.

In some embodiments, certain protocol steps may be conducted outside of a droplet actuator and certain protocol steps may be conducted on a droplet actuator. For example, in some embodiments, samples and reagents may be prepared outside the droplet actuator and combined and incubated on the droplet actuator. Reagent preparation (e.g., buffers, PCR master mix solutions, and normalization solutions) may also be prepared using on-bench protocols prior to loading on a droplet actuator. In another embodiment reagent and/or samples may be prepared in reservoirs associated with the droplet actuator then flowed to different operations gaps, and/or prepared in the droplet operations gap.

Figure 6:
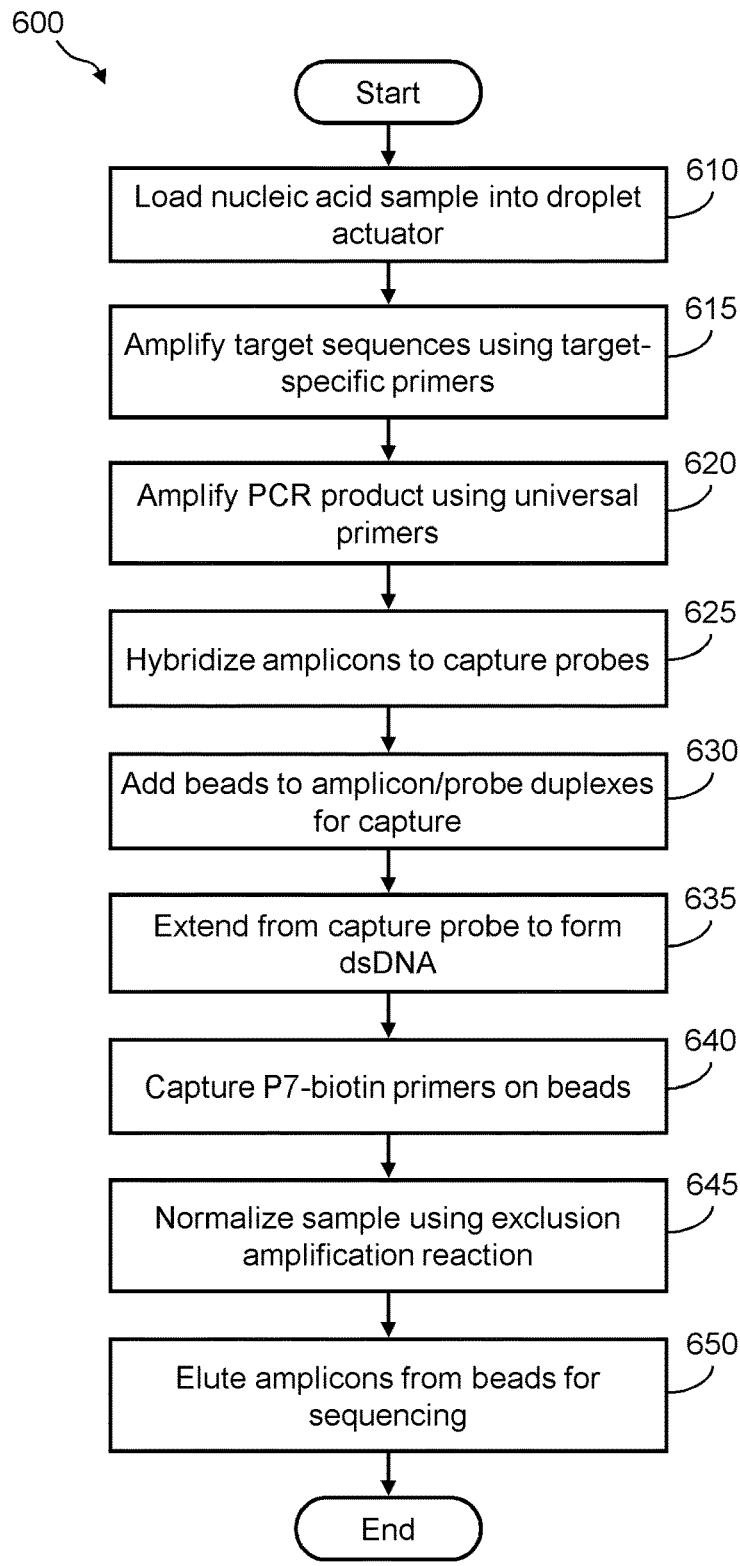
FIG. 6 illustrates a flow diagram of another non-limiting example of a method of preparing an amplified sample and/or a normalized sample for downstream analytical applications such as, for example, sequencing.

FIG. 6 illustrates a flow diagram of a non-limiting example of a method 600 of preparing a targeted amplicon library, for example on a droplet actuator, for downstream analytical applications such as, for example, sequencing in accordance with some embodiments of the disclosure. Method 600 may include, but is not limited to, the following steps.

At a step 610, a nucleic acid sample such as, for example, a genomic DNA sample (e.g., from about 1 ng to about 10 ng) is provided, for example by loading into a sample reservoir of a droplet actuator. In some embodiments, a bead-based protocol performed on the droplet actuator is used to concentrate and purify a genomic DNA sample prior to subsequent sample processing steps. In one example, the bead-based protocol uses magnetically responsive SPRI beads (e.g., Solid Phase Reversible Immobilization beads, Agencourt AMPureXP available from Beckman Coulter) to concentrate and purify the genomic DNA sample. For example, the genomic DNA is immobilized on magnetically responsive beads (e.g., SPRI beads) and a magnet and a series of washes are used to concentrate and purify the DNA prior to subsequent processing steps.

At a step 615, target nucleic acid sequences are amplified in a multiplex PCR amplification reaction using target-specific primer pairs that flank regions of interest. The target-specific primer pairs include, for example, (1) a forward primer that comprises a target-specific region and optionally a sequencing-by-synthesis (SBS) primer sequence, and (2) a reverse primer that comprises a target-specific sequence and optionally a universal sequence. The forward and reverse primers in each primer pair flank a region of interest in the target nucleic acid molecule. In general, any number of primer pairs can be used. In some examples, 200 primer pairs are used in a multiplex amplification format (e.g., 200-plex) to target 200 DNA sequences of interest. The number of PCR cycles can generally be any number of cycles and can be, for example, from 2 to about 100 cycles, about 5 to about 60, about 10 to about 40, about 15 to about 30 PCR cycles. In some examples of the methods disclosed herein, the number of PCR cycles can be from 4 to about 10 cycles, about 6 to about 20, about 8 to about 15, about 10 to about 30 PCR cycles. In some embodiments, from 4 to 6 PCR cycles can be used to amplify the targeted DNA sequences.

At a step 620, a second amplification reaction is performed using a universal primer pair. The universal primer pair includes a forward primer and optionally a reverse primer. In some embodiments, the forward primer includes an SBS complementary sequence, optionally a unique index sequence, and a primer sequence, for example P5 primer sequence. The reverse primer includes a complementary universal primer sequence. The number of PCR cycles can generally be any number of cycles and can be, for example, from 4 to about 10 cycles, about 6 to about 20, about 8 to about 15, about 10 to about 30 PCR cycles. In one example, 14 PCR cycles are used in the second amplification reaction.

At a step 625, amplicons are hybridized to capture probes in a solution-based hybridization reaction. The capture probe includes, for example, a target-specific capture sequence, a primer sequence (e.g., P7 primer sequence), and a biotin label. The target-specific capture sequence has sequence complementarity to a sequence in a targeted region of interest in the nucleic acid sample. In one example, 200 capture probes with different capture sequences are used in a hybridization reaction to target 200 DNA sequences.

At a step 630, capture beads such as, for example, magnetically-responsive streptavidin-coated capture beads (SA capture beads) are added to the hybridization reaction for capture of hybridized amplicon\capture probe duplexes. Hybridized amplicon\capture probe duplexes and un-hybridized capture probes are immobilized on the SA capture beads by formation of a biotin-streptavidin binding complex.

At a step 635, the target-specific capture sequence of capture probes hybridized to targeted DNA sequences is extended to form an immobilized complementary DNA strand.

At a step 640, a quantity of capture probes such as, for example, P7-biotin primers are captured onto the SA capture beads with extended amplicon/capture probe duplexes thereon. The P7-biotin primers include a P7 primer sequence and a biotin label. In this example, the P7-biotin primers are immobilized on the SA capture beads by formation of a biotin-streptavidin binding complex. The SA capture beads with extended amplicon/capture probe duplexes thereon now include a quantity of immobilized P7-biotin primers. The P7-biotin primers are used in subsequent exclusion amplification reaction for library normalization at step 645 as described below.

At a step 645, the nucleic acid sample is normalized using an exclusion amplification (ExAmp) reaction. Sample (ExAmp) normalization is performed to equalize sample quantities and adjust the concentration of DNA for subsequent sequencing. In some embodiments, preparation of the ExAmp reaction solution for library normalization is prepared on-actuator. In some embodiments, the ExAmp reaction solution for library normalization is prepared on-bench and subsequently loaded into a reagent dispensing reservoir of a droplet actuator. The ExAmp reaction solution includes reaction reagents and normalization primers (e.g., P5 primer sequences). The ExAmp library normalization reaction is an isothermal amplification reaction that uses a first set of normalization primers (e.g., P7-biotin primers) immobilized on the SA beads and a second set of normalization primers (e.g., P5 primers) in solution as normalization primers for library normalization. The reaction conditions (e.g., incubation time, P7 and/or P5 primer concentration, and reaction components) can be selected such that all P7-primer sites on the SA beads are converted, e.g., the reaction is run to saturation.

At a step 650, the library amplicons are eluted from the capture beads for sequencing. In one example, illustrated in FIG. 7B, amplicons 390 are eluted from SA beads 385 and denatured by heating at 95° C. for 4 minutes.

Figure 7A:
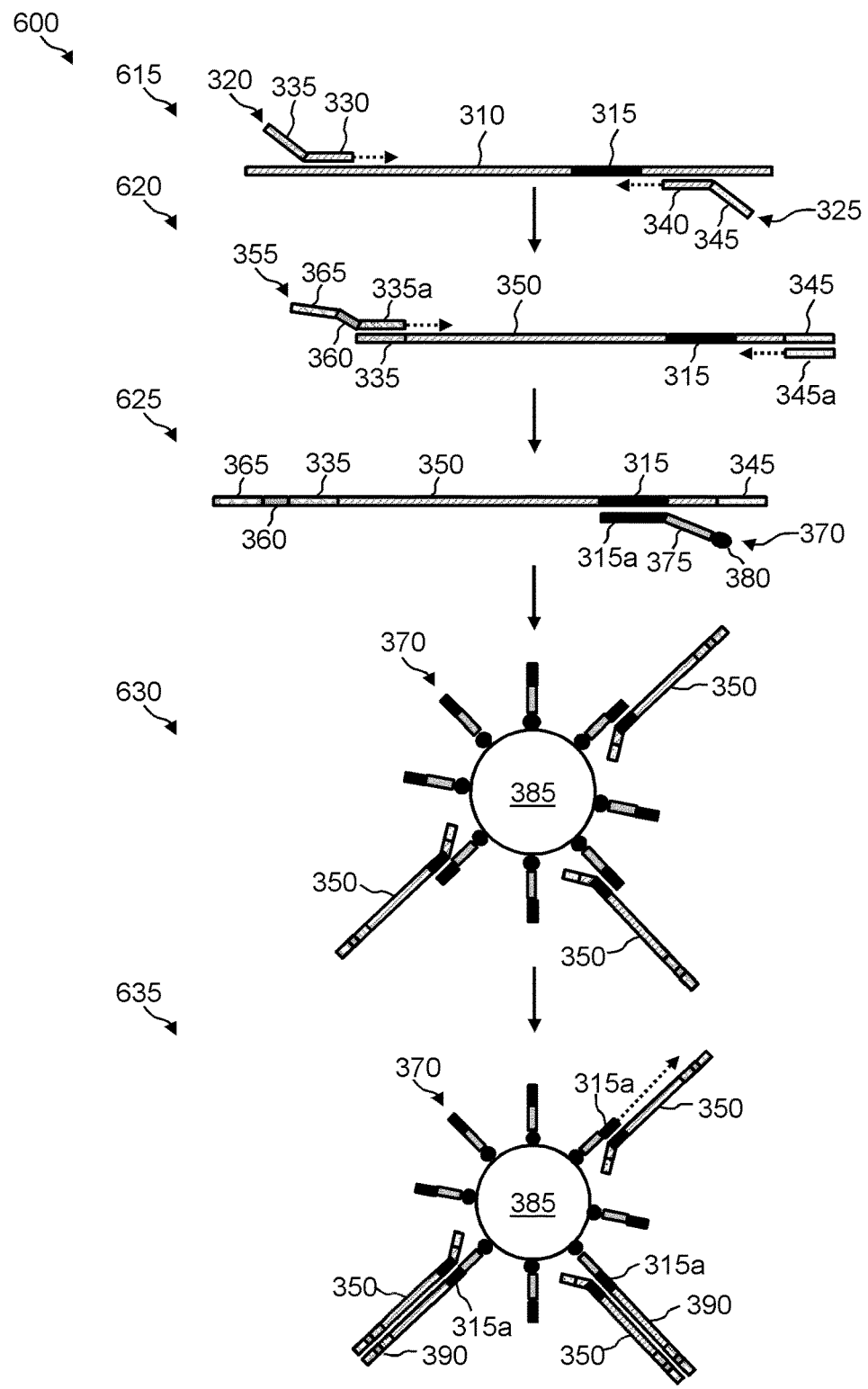
FIGS. 7A and 7B show pictorially the steps of the method of FIG. 6.
Figure 7B:
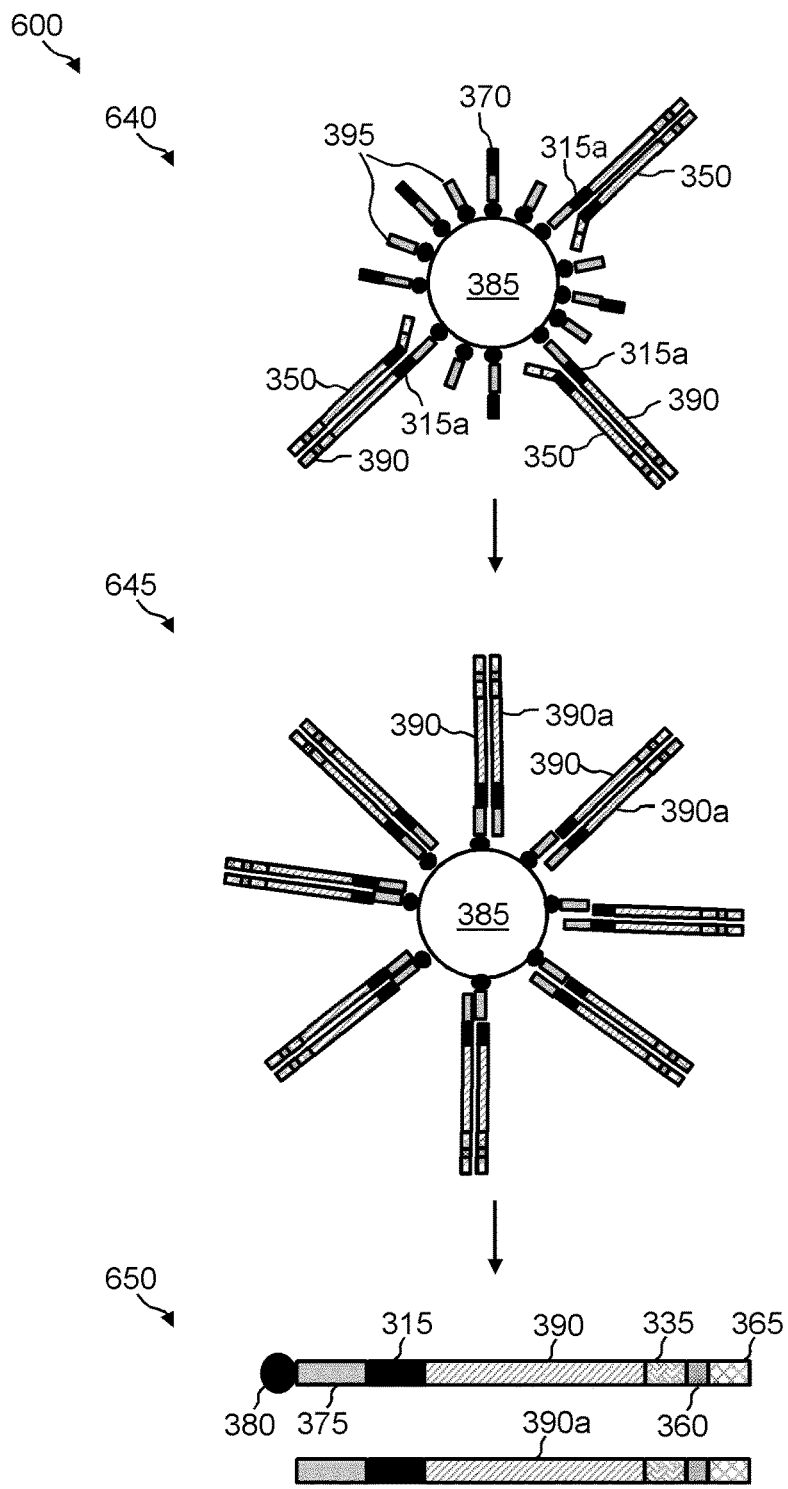
Figure 8:
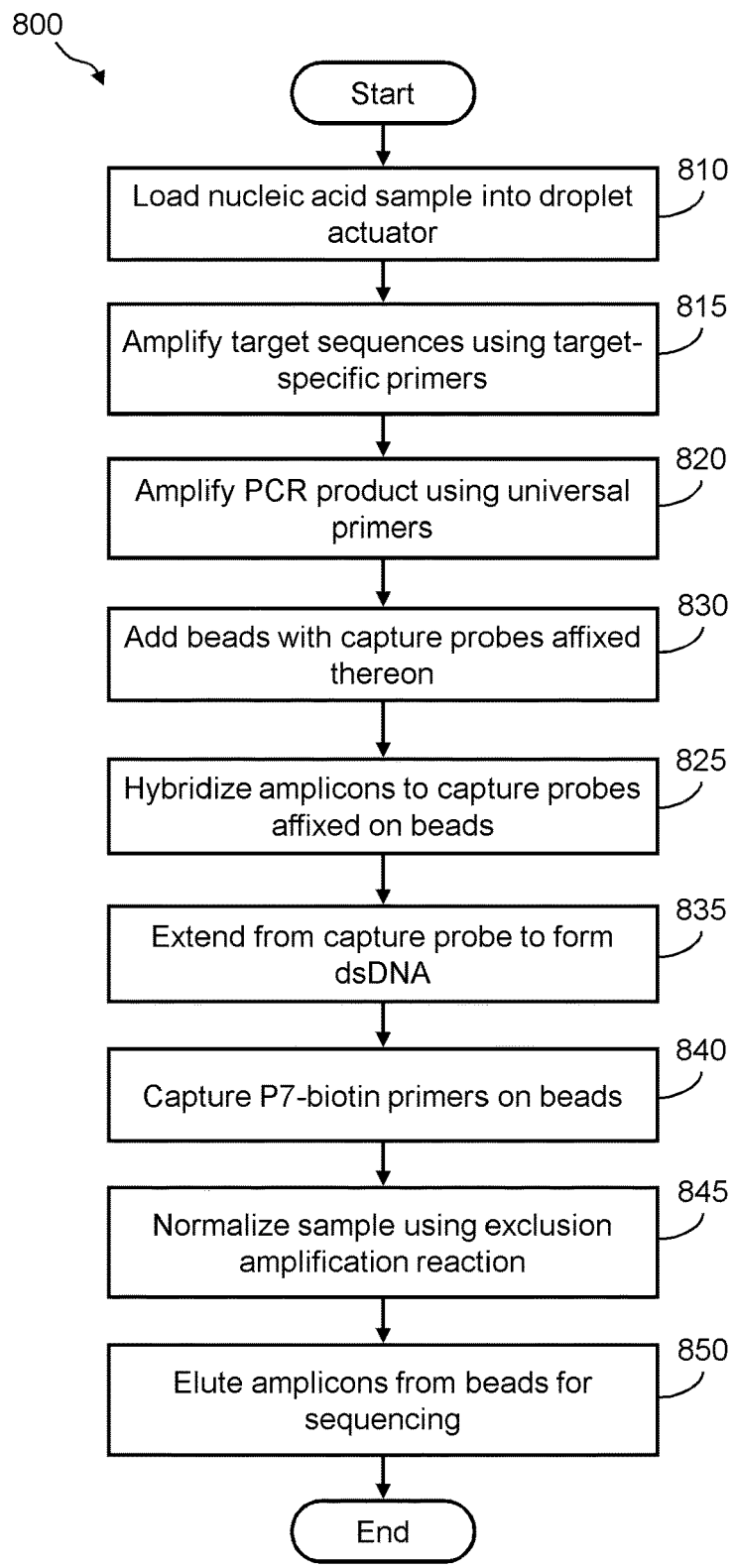
FIG. 8 depicts a flow diagram of another non-limiting example of a method of nucleic acid amplification and normalization in accordance with some embodiments of the disclosure.
Figure 9A:
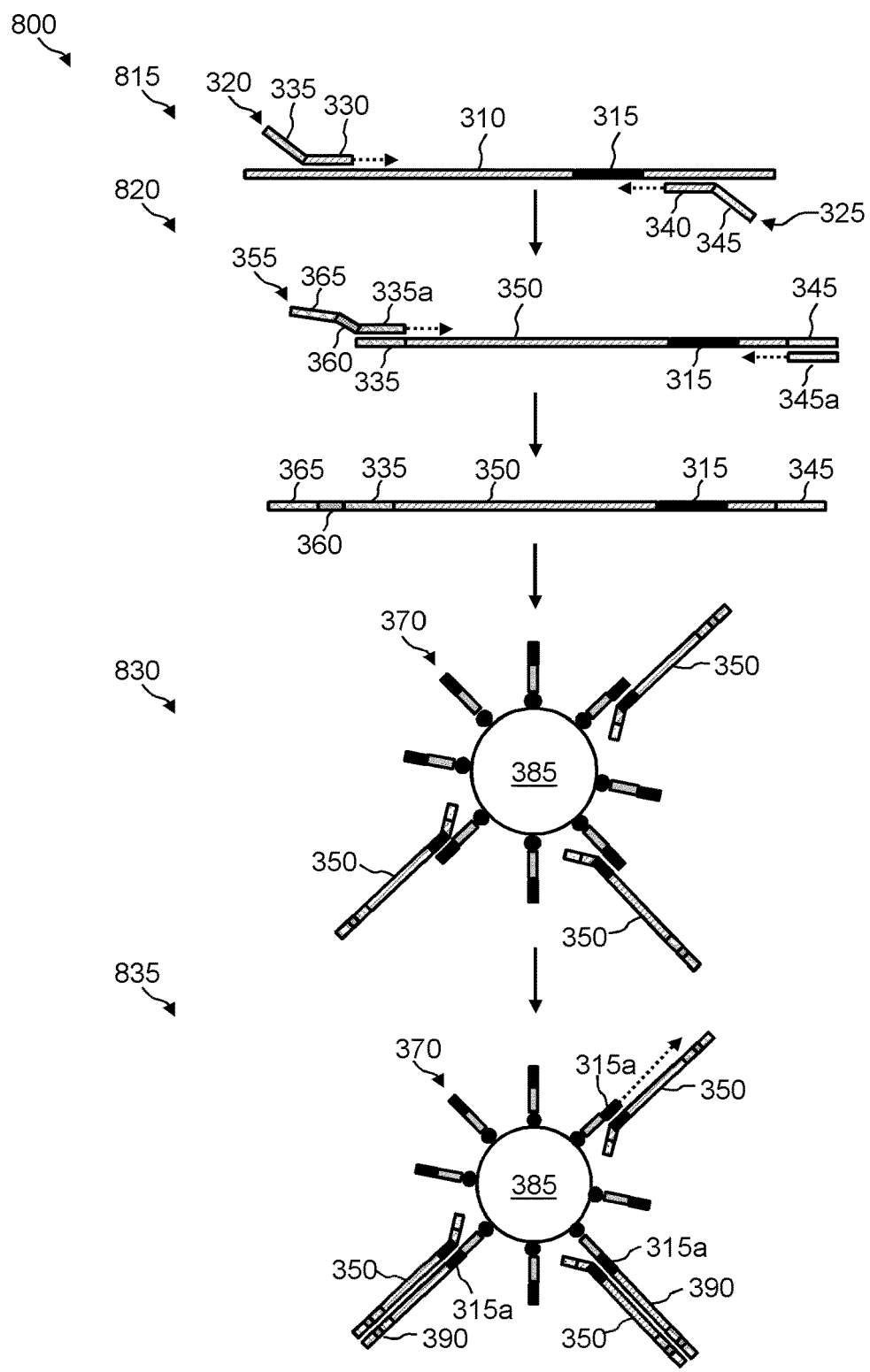
FIGS. 9A and 9B show pictorially the steps of the method of FIG. 8.
Figure 9B:
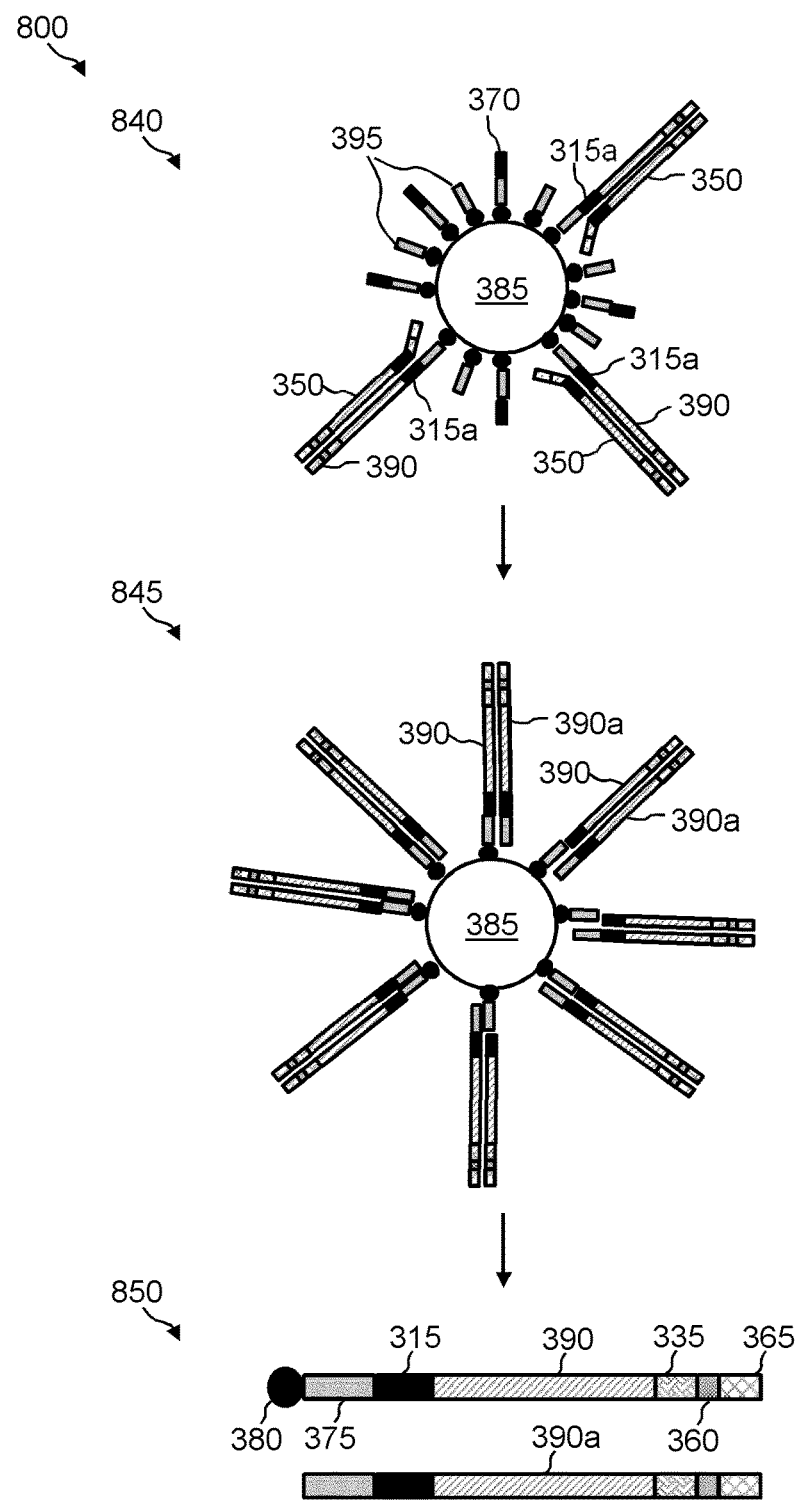

FIGS. 7A and 7B show pictorially the steps of method 600 of FIG. 6. Namely, a genomic DNA sample (not shown) includes a target nucleic acid molecule 310. The target nucleic acid molecule 310 includes a capture region 315. At step 615, target nucleic acid molecule 310 is amplified in a first enrichment amplification reaction, which is optionally carried out in multiplex format using a target-specific primer pair. The target-specific primer pair includes, for example, a target-specific forward primer 320 and a target-specific reverse primer 325. Forward primer 320 includes a target-specific region 330 and optionally a universal sequence. In some embodiments, the universal sequence includes a SBS primer sequence 335 (e.g., SBS3). Reverse primer 325 includes a target-specific region 340 and optionally a universal primer region 345. Target-specific regions 330 and 340 flank a region of interest in the target nucleic acid molecule 310. In general, any number of target-specific primer pairs can be used. In some examples, 200 target-specific primer pairs can be used in a multiplex amplification format (e.g., 200-plex) to target 200 DNA sequences of interest. The number of PCR cycles can generally be any number of cycles and can be, for example, from 2 to about 100 cycles, about 5 to about 60, about 10 to about 40, about 15 to about 30 PCR cycles. In some examples of the methods disclosed herein, the number of PCR cycles can be from 4 to about 10 cycles, about 6 to about 20, about 8 to about 15, about 10 to about 30 PCR cycles. In some embodiments, from 4 to 6 PCR cycles can be used to amplify the targeted DNA sequences. In some embodiments, 4 PCR cycles can be used to amplify the targeted DNA sequences. An amplicon 350 synthesized using forward primer 320 and reverse primer 325 now includes SBS primer region 335 and universal primer region 345.

At step 620, an optional second enrichment amplification reaction (e.g., 14 PCR cycles) is performed using a universal primer pair. The universal primer pair includes, for example, a universal forward primer 355 and a universal reverse primer 345a. In some embodiments, the universal forward primer 355 includes a region having sequence complementarity to the universal sequence of the target-specific forward primer 320 at step 615. In some embodiments, the universal forward primer 355 includes an SBS complementary region 335a that is complementary to SBS primer region 335. In some embodiments, universal forward primer 355 includes an index region 360, and optionally a primer region such as, for example a P5 primer region 365. The universal reverse primer 345a includes a sequence having sequence complementarity to the universal primer region 345 of the target-specific reverse primer 325 described at step 615 above. In general, any number of universal primer pairs can be used. The number of PCR cycles can generally be any number of cycles and can be, for example, from 2 to about 100 cycles, about 5 to about 60, about 10 to about 40, about 15 to about 30 PCR cycles. In some examples of the methods disclosed herein, the number of PCR cycles can be from 4 to about 10 cycles, about 6 to about 20, about 8 to about 15, about 10 to about 30 PCR cycles. In some embodiments, from 10 to 20 PCR cycles can be used to amplify the targeted DNA sequences. In some embodiments, 14 PCR cycles can be used to amplify the targeted DNA sequences. Amplicon 350 now includes P5 primer region 365, index region 360, SBS primer region 335 and universal primer region 345.

At step 625, amplicon 350 is hybridized to a capture probe 370 in a solution-based hybridization reaction. In some embodiments, the capture probe 370 includes a capture complementary region 315a that is complementary to capture region 315 in amplicon 350. In some embodiments, the capture probe 370 further includes a primer region such as, for example a P7 primer region 375, and optionally a labeling reagent such as, for example, a biotin label 380.

At step 630, a quantity of capture beads such as, for example, SA capture beads 385 are added to the hybridization reaction for capture of hybridized amplicon 350\capture probe 370 duplexes and optionally unhybridized capture probes 370. Hybridized amplicon\capture probe duplexes and un-hybridized capture probes are immobilized on the SA capture beads by formation of a biotin-streptavidin binding complex.

At step 635, the capture complementary region 315a of capture probe 370 is extended to form an immobilized DNA strand 390. DNA strand 390 immobilized on capture bead 385 now includes biotin label 380, P7 primer region 375, SBS primer region 335, index region 360, and P5 primer region 365.

At optional step 640, a quantity of modified capture probe 395, which is essentially the capture probe 370 devoid of the capture region the capture region 315, are added to the SA capture bead reaction. In this exemplary embodiment, the modified capture probe 395 includes P7 primer region 375 attached to biotin label 380. Modified capture probe 395 (e.g., P7-biotin primers) are immobilized on SA capture beads 385 by formation of a biotin-streptavidin binding complex. SA capture beads 385 with amplicon 390/capture probe 370 duplexes thereon now include a quantity of immobilized P7-biotin primers 395.

At step 645, a normalizing amplification is carried out, for example, under isothermal amplification procedure such as, for example, in an ExAmp reaction using immobilized P7-biotin primer 395 and P5 primers in the reaction solution (not shown) as normalization primers. The reaction conditions (e.g., incubation time, P7 and/or P5 primer concentration, and reaction components) can be selected such that all P7-primer sites on the SA beads are converted, e.g., the reaction is run to saturation. The amount of P7 primers immobilized on the solid substrate is used to control the amount of amplification product, thereby normalizes the amounts of end products across multiple nucleic acid samples or libraries.

At optional step 650, amplicons 390 are eluted from SA beads 385 for sequencing. In one example, amplicons 390 are eluted from SA beads 385 and denatured by heating at 95° C. for 4 minutes.

In addition or alternatively, in some embodiments of the methods according to this and other aspects of the disclosure, the hybridization of capture probes 370 with amplicon 350 can be carried out in solid phase, e.g., on capture beads. As illustrated in the flow diagrams shown at FIGS. 8 and 9A-9B, at step 830, a quantity of capture beads 385 with capture probes 370 affixed thereon are added to the hybridization reaction for capture of amplicons 350. The hybridization step 825 is then carried out, wherein the capture probes immobilized on the capture beads are hybridized with the amplicons 350 to form amplicon 350\capture probe 370 duplexes that are immobilized on the solid phase, e.g., capture beads. The remaining steps 830, 835, 840, 845, and 850 are carried out similarly to the corresponding steps 630, 635, 640, 645, and 650 of the alternative methods described in FIGS. 6 and 7A-7B.

III. Droplet Actuator Configured for Genomic DNA Input to Targeted Amplicon Sample Output In one aspect, some embodiments disclosed herein relate to certain droplet actuated molecular techniques. In some embodiments, a droplet actuator may, for example, include a bottom substrate and a top substrate that are separated by a droplet operations gap. The droplet operations gap contains filler fluid, such as silicone oil or hexadecane filler fluid. The bottom substrate can be, for example, a printed circuit board (PCB) that may include an arrangement of droplet operations electrodes (e.g., electrowetting electrodes). The top substrate can be, for example, a plastic or glass substrate. The top substrate may include a ground reference plane or electrode.

In one example, a droplet actuator may be adapted for use in conducting a multiplexed targeted amplicon sample preparation protocol. For example, the composition of the filler fluid may be selected for performance with reagents used in a particular protocol. Droplet transport voltage (e.g., electrowetting voltage) and frequency may also be selected for performance with reagents used in a particular protocol. Design parameters may be varied, e.g., number and placement of on-actuator reservoirs, number of independent electrode connections, size (volume) of different reservoirs, placement of magnets/bead washing zones, electrode size, inter-electrode pitch, and height (between top and bottom substrates) of the droplet operations gap.

The droplet actuator may be designed to fit onto an instrument deck that houses additional-droplet actuator features, such as one or more magnets for immobilization of magnetically responsive beads and one or more heater assemblies for controlling the temperature within certain reaction and/or washing zones.

Manipulation of droplets on a droplet actuator includes droplet operations such as dispensing, transporting, merging, incubating, splitting, and mixing. The size of a droplet can vary depending on the droplet operation used in a protocol step. In one example, a unit sized droplet, e.g., "droplet unit" (DU), is about 0.34 µL and can be described as a 1× droplet. Typical protocol reactions use a range of droplet sizes from about 1 DU (e.g., a 1× droplet) to about a 6 DU droplet (e.g., a 6× droplet).

FIG. 1 illustrates a top view of an example of an electrode arrangement 100 of a droplet actuator suitable for use in conducting a multiplexed targeted amplicon library preparation protocol in accordance with some exemplary embodiments of the disclosure. Electrode arrangement 100 is configured for multiplexed processing of multiple genomic DNA samples for construction of one or more targeted amplicon libraries. Droplet operations are conducted atop electrode arrangement 100 on a droplet operations surface. In this example, electrode arrangement 100 is configured for processing up to 8 different samples in parallel in dedicated reaction regions for construction of 8 different targeted amplicon sequencing libraries.

Electrode arrangement 100 includes 8 sample reservoir electrodes 110 (hereafter called sample reservoir electrodes 110a through 110h) for inputting and dispensing sample solutions (e.g., a genomic DNA sample). Electrode arrangement 100 also includes 8 PCR/biochemical reaction zones 115 (hereafter called PCR/biochemical reaction zones 115a through 115h) for performing certain processing steps for construction of each targeted amplicon library. Each of the PCR/biochemical reaction zones 115 includes a cluster or arrangement of multiple electrodes for conducting droplet operations. The processing steps include, for example, PCR amplification, capture probe hybridization, bead capture, primer extension, library normalization, and library elution. Electrode arrangement 100 also includes 8 index reservoir electrodes 120 (hereafter called index reservoir electrodes 120a through 120h) for dispensing 8 unique indexing oligonucleotide solutions for indexing each targeted amplicon library. Electrode arrangement 100 also includes 14 reagent reservoir electrodes 125 (hereafter called reagent reservoir electrodes 125a through 125n) configured for dispensing different reagent liquids (e.g., wash buffers, PCR master mix solutions, magnetically responsive capture beads, primer extension reagents, library normalization reagents, and elution/denaturation buffer solutions). In some implementations, reservoir electrodes 110 and index reservoir electrodes 120 are used as waste reservoir. In some implementations, reagent reservoir electrodes 125 are not used for waste.

Generally, the sample reservoir electrodes 110, PCR/biochemical zones 115, index reservoir electrodes 120, and reagent reservoir electrodes 125 are interconnected through an arrangement, such as a path or array, of droplet operations electrodes 130.

In electrode arrangement 100, sample reservoir electrode 110a corresponds to PCR/biochemical reaction zone 115a, which corresponds to index reservoir electrode 120a; sample reservoir electrode 110b corresponds to PCR/biochemical reaction zone 115b, which corresponds to index reservoir electrode 120b; and so on through sample reservoir electrode 110h corresponding to PCR/biochemical reaction zone 115h, which corresponds to index reservoir electrode 120h. The 8 arrangements of corresponding sample reservoir electrodes 110, PCR/biochemical reaction zones 115, and index reservoir electrodes 120 form 8 dedicated reaction lanes 135 (hereafter called reaction lanes 135a through 135h) for processing each sample input. The use of dedicated lanes for sample droplets minimizes cross-contamination among different genomic DNAs.

One or more magnets (not shown) may be located in proximity to certain droplet operations electrodes 130 for retaining a quantity of magnetically responsive beads. The magnet may, for example, be a permanent magnet or an electromagnet. In one example, the magnet may be a movable magnet that may be moved into proximity of and away from its respective droplet operations electrode 130. Each magnet is positioned in a manner which ensures spatial immobilization of nucleic acid-attached beads during certain processing steps (e.g., bead washing, library capture, enzymatic reactions, and bead removal following elution/denaturation of processed genomic DNA).

Electrode arrangement 100 may include one or more temperature control zones 140. In one example, three temperature control zones 140 may be used (e.g., temperature control zones 140a, 140b, and 140c). Temperature control elements (not shown) control the temperature of filler fluid (not shown) in vicinity of temperature control zones 140. Each temperature control zone 140 may be independently controlled to a certain temperature(s) sufficient for the different processing steps in a library construction protocol. For example, temperature control zone 140a may be heated to about 98° C., which is a temperature sufficient for denaturation of DNA, while temperature control zone 140b may be heated to from about 60° C. to about 72° C., which is a temperature range suitable for annealing and extension reactions. While three temperature control zones 140 are shown, any number of temperature control zones 140 may be associated with electrode arrangement 100.

Electrode arrangement 100 is an example of an electrode arrangement on a droplet actuator that can be used to facilitate the methods in accordance with some embodiments of the disclosure; namely, to facilitate automated liquid handling for amplification and selection of targeted regions of genomic DNA for processing into amplicon libraries for sequencing, as described herein.

IV. General Digital Microfluidic Protocol for Preparation of a Targeted Amplicon Library In another example, methods 200, 400, 600, and 800 of FIGS. 2, 4, 6, and 8, respectively, can be described as step-by-step, droplet-based protocols for preparation of a targeted amplicon library. An example of a droplet-based protocol for preparation of a targeted amplicon library includes, but is not limited to, the following droplet movements.

In another example of step 610 of method 600 of FIG. 6, a genomic DNA sample comprising a quantity of magnetically responsive SPRI beads is loaded into a sample reservoir of a droplet actuator. In one example, the genomic DNA sample includes about 1 ng of genomic DNA, a DNA binding buffer solution, and a quantity of magnetically responsive SPRI beads (e.g., from about 20 µL to about 50 µL). The genomic DNA sample with SPRI beads therein is incubated for a period of time sufficient for binding of the DNA onto the beads. Sample solution with SPRI beads is transported using droplet operations to an area of sample reservoir within the magnetic field of a magnet. In some examples, the entire volume of the sample (20-50 µl) is used rather than a few DUs are used. The magnetically responsive SPRI beads with genomic DNA thereon are immobilized by the magnetic field of the magnet. In one example, the magnet is a moveable magnet that can be moved into proximity of the certain droplet operations electrode and away from the certain droplet operations electrode. A supernatant is pulled back from the immobilized beads and returned using droplet operations to the sample reservoir for disposal. In some examples, the entire supernatant volume (20-50 µl) is pulled back. A 2× bead wash buffer droplet is dispensed from a reagent reservoir and transported using droplet operations to the immobilized SPRI beads with genomic DNA thereon to form a 2× wash buffer/SPRI bead droplet. The SPRI beads with genomic DNA thereon are re-suspended and washed using a bead washing protocol. The magnet is positioned in proximity of the 2× wash buffer/SPRI bead droplet such that the magnetically responsive SPRI beads are immobilized by the magnetic field of the magnet. A 2× supernatant droplet is pulled off and transported using droplet operations to the sample reservoir for disposal. A 1× elution buffer droplet is transported from a reagent reservoir to the immobilized magnetically responsive SPRI beads with genomic DNA thereon to form a 1× elution buffer/SPRI bead droplet. The 1× elution buffer/SPRI bead droplet is incubated at about 55° C. for about 2 minutes to elute the DNA from the SPRI beads. The magnetically responsive SPRI beads are then immobilized by the magnetic field of the magnet and a 1×DNA sample droplet is transported using droplet operations away from the immobilized magnetically responsive beads to a dedicated PCR/biochemical reaction zone. A 1× bead wash buffer droplet is transported from a reagent dispensing reservoir and merged with the immobilized magnetically responsive SPRI beads (now devoid of genomic DNA) to form a 1×SPRI bead/wash buffer droplet. The 1×SPRI bead/wash buffer droplet is transported using droplet operations to the sample reservoir for disposal.

In another example of step 615 of method 600 of FIG. 6, a 1×PCR reagent droplet is dispensed from a reagent dispensing reservoir. The 1×PCR reagent droplet includes, for example, buffer, polymerase, and dNTPs. The 1×PCR reagent droplet is combined using droplet operations with the 1×DNA sample droplet to yield a 2× amplification droplet. A 1× target-specific primer droplet is dispensed from a reagent dispensing reservoir and combined using droplet operations with the 2× amplification droplet to yield a 3× target-specific amplification droplet. In one example, the 1× target-specific primer droplet includes forward (e.g., forward primer 320 of FIGS. 7A-7B) and reverse (reverse primer 325 of FIGS. 7A-7B) pairs for a 200-plex amplification reaction. PCR cycling (e.g., 4 cycles) is performed in a flow-through format where for each cycle the 3× target-specific amplification droplet is cyclically transported using droplet operations between different temperature control zones on the droplet actuator. In one example, the amplification reaction is an initial incubation at 98° C. for 2 minutes, then 4 PCR cycles of the following sequence: 98° C. for 20 seconds, 70° C. for 20 seconds, 56° C. for 60 seconds, 72° C. for 75 s; followed by a final incubation at 72° C. for 60 seconds.

In another example of step 620 of method 600 of FIG. 6, a 2× index primer droplet (e.g., forward primer 355 of FIGS. 7A-7B) and a 1×PCR reagent droplet are dispensed from reagent dispensing reservoirs and combined using droplet operations to yield a 3× universal primer droplet. The 1×PCR reagent droplet includes, for example, buffer, polymerase, dNTPs, and a universal reverse primer (e.g., reverse primer 345a of FIG. 7A. In one example, the universal reverse primer is part of the 2× index primer droplet. The 3× universal primer droplet is split using droplet operations to yield two 1.5× universal primer droplets. One 1.5× universal primer droplet is combined using droplet operations with the 3× target-specific amplification droplet to yield a 4.5× universal amplification droplet. The second 1.5× universal primer droplet is transported using droplet operations to a waste collection reservoir. In one example, the waste collection reservoir is the sample port used as waste at this point of the workflow. PCR cycling (e.g., 14 cycles) is performed in a flow-through format where for each cycle the 4.5× universal amplification droplet is cyclically transported using droplet operations between different temperature control zones on the droplet actuator. In one example, the amplification reaction is an initial incubation at 98° C. for 30 seconds, then 14 PCR cycles of the following sequence: 98° C. for 20 seconds, 70° C. for 20 seconds, 60° C. for 60 seconds, 72° C. for 60 s; followed by a final incubation at 72° C. for 120 seconds.

In another example of step 625 of method 600 of FIG. 6, a 1× capture probes droplet (e.g., a plurality of different capture probe 370 of FIGS. 7A-7B) and two capture buffer droplets (e.g., a 2× and a 1× capture buffer droplet comprising 20×SSC) are dispensed from reagent dispensing reservoirs and combined using droplet operations to yield a 4× capture probes droplet. The 4× capture probes droplet is split using droplet operations into two 2× capture probes droplets. One 2× capture probes droplet is combined using droplet operations with the 4.5× universal amplification reaction droplet to yield a 6.5× amplicon/capture probe droplet. The second 2× capture probes droplet is transported using droplet operations to a waste collection reservoir. In one example, capture probe hybridization is performed by incubating the amplicon/capture probe hybridization droplet at 98° C. for 3 minutes, then 75° C. for 30 seconds, then 60° C. for 10 minutes, and then 40° C. for 5 minutes.

In another example of step 630 of method 600 of FIG. 6, streptavidin (SA)-coated magnetically responsive beads are prepared for capture of the hybridized amplicon/probe duplexes. For example, a 1× SA bead droplet is dispensed from a reagent dispensing reservoir and transported using droplet operations to a certain droplet operations electrode within the magnetic field of a magnet. The magnetically responsive beads within the 1× SA bead droplet are immobilized by the magnetic field of the magnet and a 1× supernatant droplet is split off and transported using droplet operations to a waste reservoir. A 2× PR2 wash buffer droplet is dispensed from a reagent reservoir and transported using droplet operations to the immobilized SA beads to form a 2× SA bead PR2 wash droplet. The beads are re-suspended and washed at room temperature for about 1 minute using a bead-wash protocol. A magnet is positioned in proximity of the 2× SA bead PR2 wash droplet such that the magnetically responsive SA beads are immobilized by the magnetic field of the magnet. A 2× supernatant droplet is pulled off and transported using droplet operations to a waste reservoir for disposal. The bead-washing protocol is repeated once using a 2×HT1 wash buffer droplet. At the end of the bead-washing protocol, a 1× HT1 resuspension droplet is dispensed and transported using droplet operations to the immobilized SA beads and the beads are re-suspended to form a 1× washed SA bead droplet. The 1× washed SA bead droplet is transported using droplet operations and merged with the 6.5× amplicon/capture probe droplet to yield a 7.5× library capture droplet. The 7.5× library capture droplet is incubated at room temperature for about 6 min for capture of amplicon/capture probe duplexes onto the SA beads via formation of a biotin-streptavidin binding complex. At the end of the incubation period, the magnetically responsive SA beads with amplicon/capture probe duplexes thereon are immobilized by the magnetic field of a magnet and a 7.5× supernatant droplet is transported using droplet operations away from the magnetic field to a waste collection reservoir. A 2× PR2 wash buffer droplet is dispensed from a reagent reservoir and transported using droplet operations to the immobilized SA beads with amplicon/capture probe duplexes thereon to form a 2× bead/amplicon wash droplet. The beads are re-suspended and washed at room temperature for about 1 minute using a bead-wash protocol. At the end of the incubation period, the magnetically responsive SA beads with amplicon/capture probe duplexes thereon are immobilized by the magnetic field of a magnet and a 2× supernatant droplet is transported using droplet operations away from the magnetic field to a waste collection reservoir.

In another example of step 635 of method 600 of FIG. 6, two 2× extension buffer droplets are dispensed from a reagent dispensing reservoir and transported using droplet operations to the immobilized SA beads with amplicon/capture probe duplexes thereon to form a 4× extension reaction droplet. The extension buffer includes, for example, buffer, polymerase, and dNTPs for synthesis of a complementary DNA strand. The 4× extension reaction droplet is incubated at about 60° C. for about 5 minutes to for extension of the target-specific capture sequence of capture probes hybridized to targeted DNA sequences. At the end of the incubation period, the magnetically responsive SA beads with extended amplicon/capture probe duplexes thereon are immobilized by the magnetic field of a magnet and a 4× supernatant droplet is transported using droplet operations away from the magnetic field to a waste collection reservoir. A 2× PR2 wash buffer droplet is dispensed from a reagent reservoir and transported using droplet operations to the immobilized SA beads with extended amplicon/capture probe duplexes thereon to form a 2× bead/amplicon wash droplet. The beads are re-suspended and washed at room temperature for about 1 minute using a bead-wash protocol. At the end of the incubation period, the magnetically responsive SA beads with extended amplicon/capture probe duplexes thereon are immobilized by the magnetic field of a magnet and a 2× supernatant droplet is transported using droplet operations away from the magnetic field to a waste collection reservoir.

In another example of step 640 of method 600 of FIG. 6, a 2× P7-biotin primer droplet is dispensed from a reagent dispensing reservoir and transported using droplet operations to the immobilized SA beads with extended amplicon/capture probe duplexes thereon to form a 2× library normalization droplet. The SA beads with extended amplicon/capture probe duplexes thereon are re-suspended and incubated at room temperature for about 6 minutes for capture of P7-biotin primers onto the SA capture beads. At the end of the incubation period, the magnetically responsive SA beads with extended amplicon/capture probe duplexes and P7-biotin primers thereon are immobilized by the magnetic field of a magnet and a 2× supernatant droplet is transported using droplet operations away from the magnetic field to a waste collection reservoir.

In another example of step 645 of method 600 of FIG. 6, the library is normalized using an exclusion amplification (ExAmp) reaction. To prepare an ExAmp reaction solution, two 2×ExAmp1 reagent droplets, one 1× ExAmp2 reagent droplet, two 2×ExAmp3-P5 reagent droplets, and one ExAmp3-P5 reagent droplet are dispensed from reagent dispensing reservoirs and combined using droplet operations to yield a 10× ExAmp reaction solution droplet. The 10× ExAmp reaction solution droplet is split using droplet operations into five 2×ExAmp reaction solution droplets. Three 2× ExAmp reaction solution droplets are transported using droplet operations to a waste collection reservoir. Two 2×ExAmp reaction solution droplet are transported using droplet operations to the immobilized SA beads with extended amplicon/capture probe duplexes and P7-biotin primers thereon to form a 4× normalization reaction droplet. The 4× normalization reaction droplet is incubated at 38° C. for about 20 minutes. At the end of the incubation period, the magnetically responsive SA beads with normalized amplicon library thereon are immobilized by the magnetic field of a magnet and a 4× supernatant droplet is transported using droplet operations away from the magnetic field to a waste collection reservoir.

In another example of step 650 of method 600 of FIG. 6, two 2×elution buffer droplets (e.g., TE buffer droplets) are dispensed from a reagent dispensing reservoir and transported using droplet operations to the immobilized SA beads with library amplicons thereon to form a 4× library elution droplet. The 4× library elution droplet is incubated at about 95° C. for about 4 for elution and denaturation of amplicons from the SA beads. At the end of the incubation period, the SA beads are immobilized by the magnetic field of the magnet and a 4× amplicon library droplet is transported using droplet operations away from the immobilized magnetically responsive SA beads for collection and subsequent sequencing.

All publications and patent applications mentioned in this specification are herein incorporated by reference to the same extent as if each individual publication or patent application was specifically and individually indicated to be incorporated by reference.

No admission is made that any reference cited herein constitutes prior art. The discussion of the references states what their authors assert, and the applicant reserves the right to challenge the accuracy and pertinence of the cited documents. It will be clearly understood that, although a number of information sources, including scientific journal articles, patent documents, and textbooks, are referred to herein, this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Additional embodiments are disclosed in further detail in the following examples, which are not in any way intended to limit the scope of this disclosure or the claims.

Example 1

Reaction Efficiency and Library Uniformity

To evaluate the reaction efficiency and uniformity of amplicons prepared using method 600 of FIG. 6, three different targeted amplicon libraries were prepared. A first targeted amplicon library was prepared using an on-bench amplification protocol, wherein target-specific primer pairs and a universal primer pair are combined in a single PCR reaction (e.g., a one-stage reaction). A second targeted amplicon library was prepared on a droplet actuator using a one-stage digital fluidic protocol, wherein target-specific primer pairs and a universal primer pair are combined in a single PCR reaction. A third targeted amplicon library was prepared on a droplet actuator using the two-stage amplification (e.g., steps 615 and 620) of method 600 of FIG. 6. For each library, amplicons were prepared using 1 ng of genomic DNA and a 161-plex, target-specific primer pool.

Figure 10:
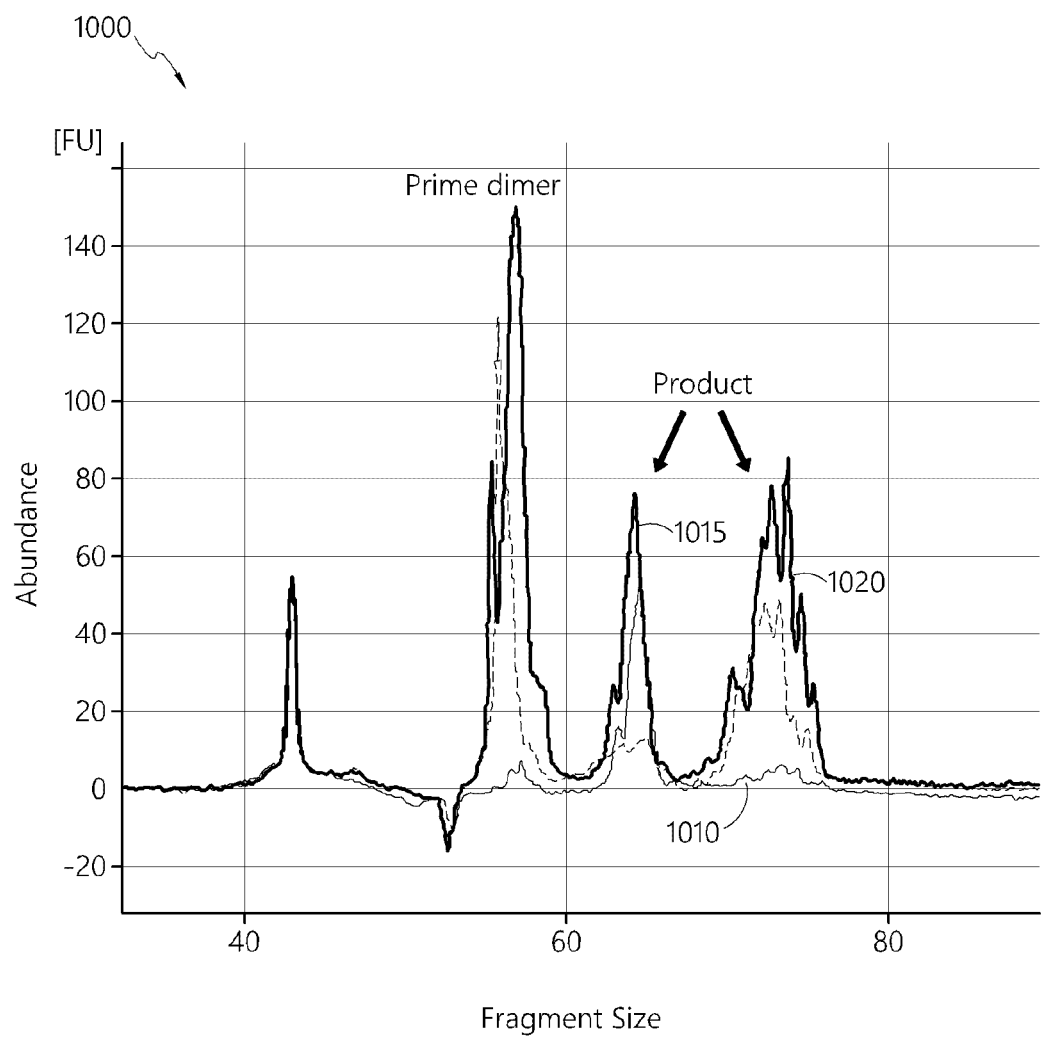
FIG. 10 shows a plot of the fragment size distributions in three targeted amplicon samples prepared using three different protocols, one being the two-stage on-actuator amplification reaction of the method of FIG. 6.

FIG. 10 shows a plot 1000 of the fragment size distributions in three targeted amplicon libraries prepared using three different protocols in accordance with some embodiments of the disclosure. Namely, one targeted amplicon library prepared using a one-stage on-bench amplification reaction, another targeted amplicon library prepared using a one-stage on-actuator amplification reaction, and yet another targeted amplicon library prepared using the two-stage on-actuator amplification reaction of method 600 of FIG. 6. Plot 1000 shows (1) a line 1010 of the fragment size distribution in the amplicon library prepared on-bench using a one-stage PCR reaction, (2) a line 1015 of the fragment size distribution in the amplicon library prepared on-actuator using a one-stage PCR reaction, and (3) a line 1020 of the fragment size distribution in the amplicon library prepared on-actuator using the two-stage amplification method 600 of FIG. 6. The data presented in FIG. 10 show that in all three amplicon libraries (lines 1010, 1015, and 1020) there was a bimodal distribution of desirable PCR products (indicated by arrows) and a peak of unwanted by-product (e.g., primer dimers). In the on-bench amplicon library prepared using a one-stage PCR reaction (line 1010), there was a substantial peak of primer dimers (a reaction by-product) and relatively low yield of desirable product. In the amplicon library prepared using an on-actuator one-stage PCR reaction (line 1015), there was a substantial reduction in the amount of primer dimers and an increase in the amount of desirable PCR product; that is the ratio of by-product to product is shifted toward desirable product and the formation of by-product (e.g., primer dimers) is minimized. Finally, in the amplicon library prepared using the two-stage on-actuator amplification reaction (line 1020) of method 600 of FIG. 6, formation of primer dimers was essentially eliminated and the amount of desirable PCR product was further increased. In addition, the two-stage on-actuator amplification reaction generally offers faster cycling in second stage (which saves time) and more modular system (which is better for development).

Figure 11A:
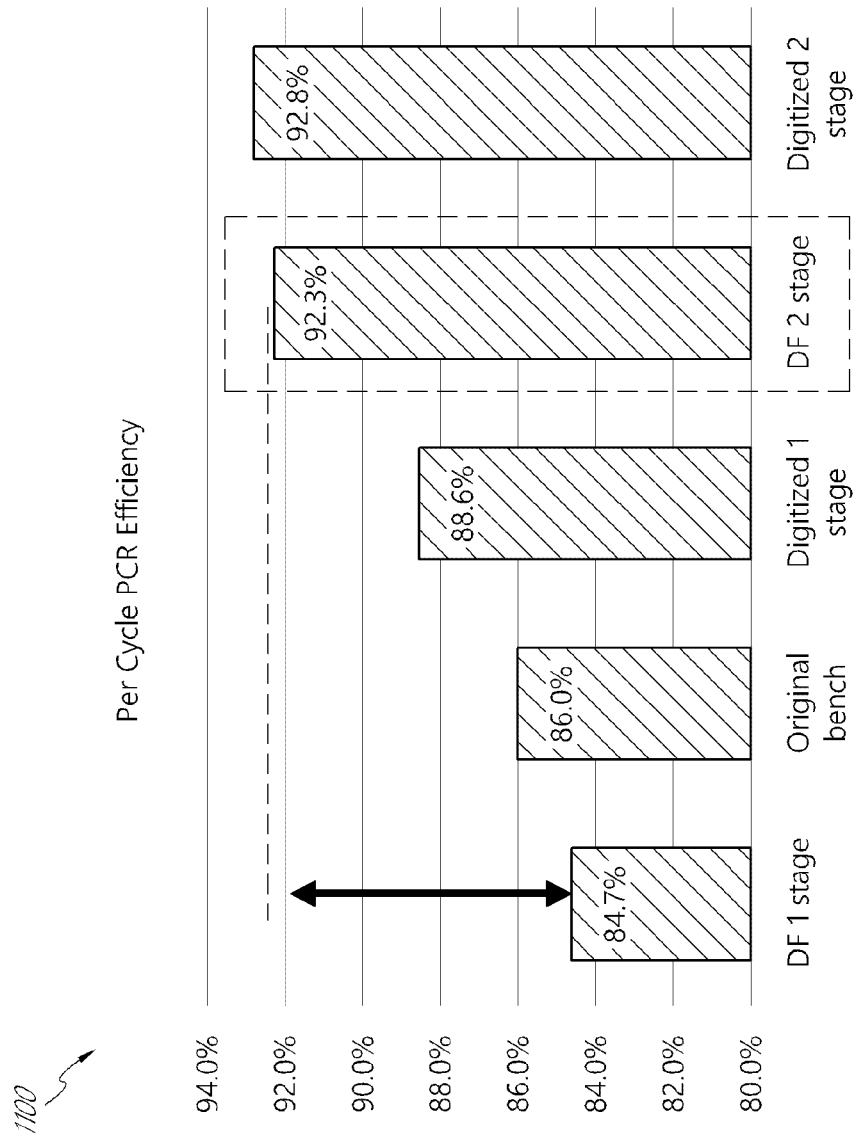
FIGS. 11A and 11B show a bar graph of PCR efficiency per cycle and a bar graph of the uniformity of amplicons in each library of FIG. 10.
Figure 11B:
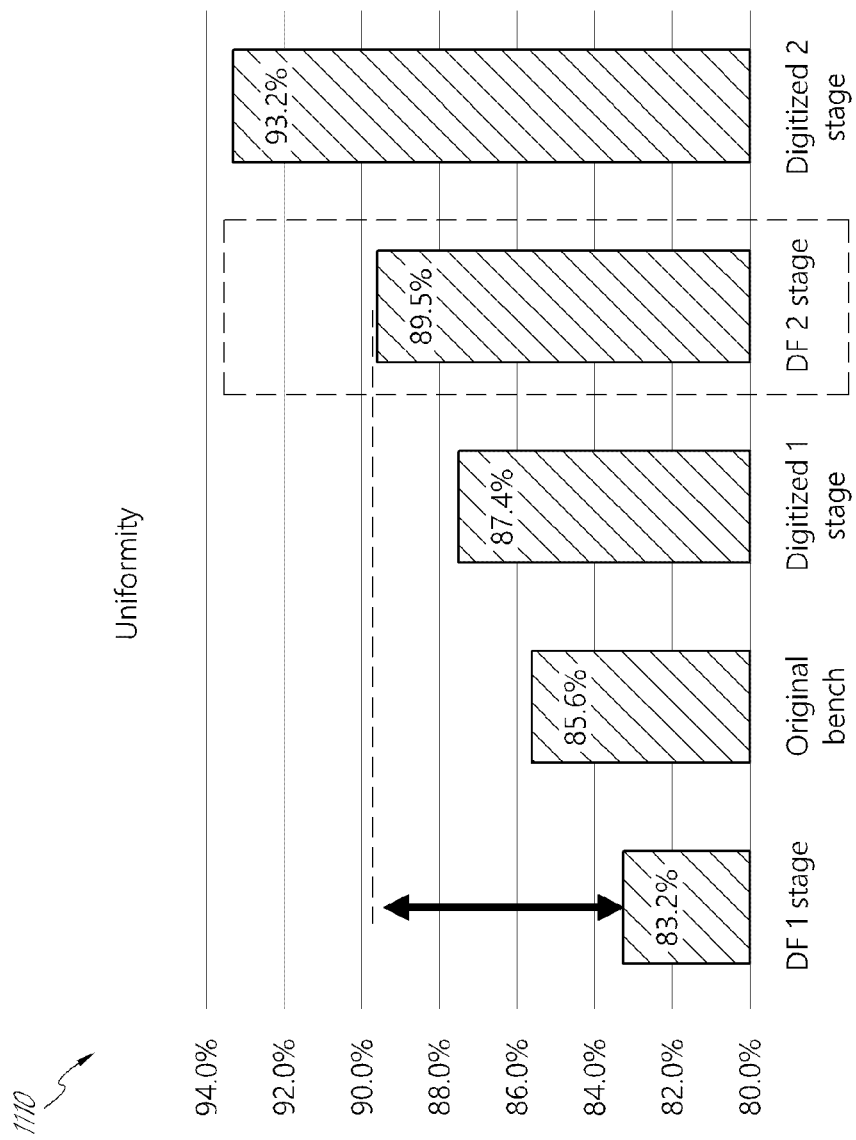

FIGS. 11A and 11B respectively show a bar graph 1100 illustrating PCR efficiency per cycle and a bar graph 1110 illustrating the uniformity of amplicons in each library of FIG. 10. Referring now to FIG. 11A, the data show that the efficiency of the PCR reaction performed on-actuator (about 92% per PCR cycle) is substantially improved using the two-stage amplification reaction of method 600 of FIG. 6 ("DF 2 stage") compared to the efficiency (about 85% per PCR cycle) of the one-stage amplification reaction ("DF 1 stage") performed on a droplet actuator. Regarding the two samples labelled "Digitized 1 stage" and "Digitized 2 stage", the term "digitized" refers to a type of experiment where reactions were run on bench but under conditions "simulating" DF. These conditions were designed to match different DF aspects as closely as possible but using regular lab equipment. In specific experiments shown in FIG. 11A as well as FIG. 11B described below, the PCR reactions were performed with the same reagent ratios as in the corresponding DF reactions, e.g. "DF 1 stage" and "DF 2 stage" (those digitized conditions were different than "Original bench" conditions) and under DF oil to simulate DF conditions. However, these digitized reactions were performed in regular thermocycler.

Referring now to FIG. 11B, the data show that distribution (or variability) of amplicons (about 89.5%) within the library generated using the two-stage amplification reaction of method 600 of FIG. 6 ("DF 2 stage") is substantially improved compared to the uniformity of amplicons (about 83%) within the library generated using the one-stage amplification reaction ("DF 1 stage") performed on a droplet actuator. Uniformity is defined as the distribution/variability of amplicons within the library. A higher uniformity means a more even distribution of amplicons in the library and provides for more efficient library coverage in sequencing.

Table 1 below shows a summary of an example of changes that were made to adapt an on-bench targeted amplification protocol to a digital fluidic format.

TABLE 1

Comparison of on-bench and digital fluidic targeted amplification protocols

| Changes | On-bench | Digital fluidic | Observed Effect |
| --- | --- | --- | --- |
| Protocol | One-stage PCR | Two-stage PCR | Yield and uniformity improvements |
| Reaction volume | 50 µL | 2 µL | Saving reagents and improving performance |
| gDNA concentration | 0.02 ng/µL | 0.5 ng/µL | Yield improvement |
| Phusion polymerase | 0.04 U/µL | 0.12 U/µL | Yield and robustness improvements |
| Target-specific primers | 10 nM each | 20 nM each | Uniformity and yield improvements |
| Universal reverse primer | 0.2 µM | 1.5 µM | Yield improvements |
| Annealing | 60° C. | 56° C. | Uniformity improvements |
| Thermal profile | 0.2° C./s cool | <0.4° C./s cool | Slower cycling |

Example 2

Solution-based Hybridization and Library Uniformity

This Example summarizes the results of experiments performed to evaluate the effect of a solution-based hybridization reaction (step 625 of method 600 of FIG. 6) on uniformity. To this end, three different libraries were prepared. One library, referred to here as "bead-based hybridization library", was prepared on-bench using traditional procedure where library capture probes are first immobilized on streptavidin coated magnetic beads through biotin streptavidin interaction and PCR amplicon is then hybridized to capture probes. In another library, referred to here as "Solution-based hybridization library and produced on-bench", PCR amplicon was first hybridized in solution to biotinylated capture probes and then immobilized through biotin streptavidin interaction on streptavidin coated magnetic beads. Finally, a third library referred to here as "Solution-based hybridization DF library" was prepared using the same sequence of steps as Solution-based hybridization library but was performed on-actuator.

Table 2 below shows the uniformity of the libraries prepared by these three different protocols. In some experiments, a fourth library was prepared based on a Bead-based hybridization performed on-actuator (DF). It was observed that the uniformity of Solution-based hybridization library was substantially improved over traditional Bead-based hybridization library. Uniformity of Solution-based hybridization in DF library prepared on-actuator was found to be improved even further.

TABLE 2

Comparison of bead- and solution-based hybridization reactions

| Condition | Uniformity |
| --- | --- |
| Bead-based hybridization | 82.5% |
| Solution-based hybridization | 87.5% |
| Solution-based hybridization in DF | 90.0% |

Example 3

Mathematical Model for Predicting Library Output

This Example summarizes experimental results illustrating that the flexibility and programmability of a droplet actuator device provides for fine control over the various biochemical reactions performed during construction of a targeted amplicon library. Because of the precise control of the biochemical reactions performed on a droplet actuator, mathematical models can be used to predict certain process outcomes. For example, product yield of amplicon hybridization and capture probes extension can be predicted from PCR product input (amplicon input) and capture probe input used in the hybridization and extension steps of method 600 of FIG. 6 using the following equation:

$$\text{Log(yield[pM])} = -0.703 + 0.846 * \text{log(probes conc.[pM each])} + 0.741 * \text{log(input conc.[pM each])}$$

Figure 12A:
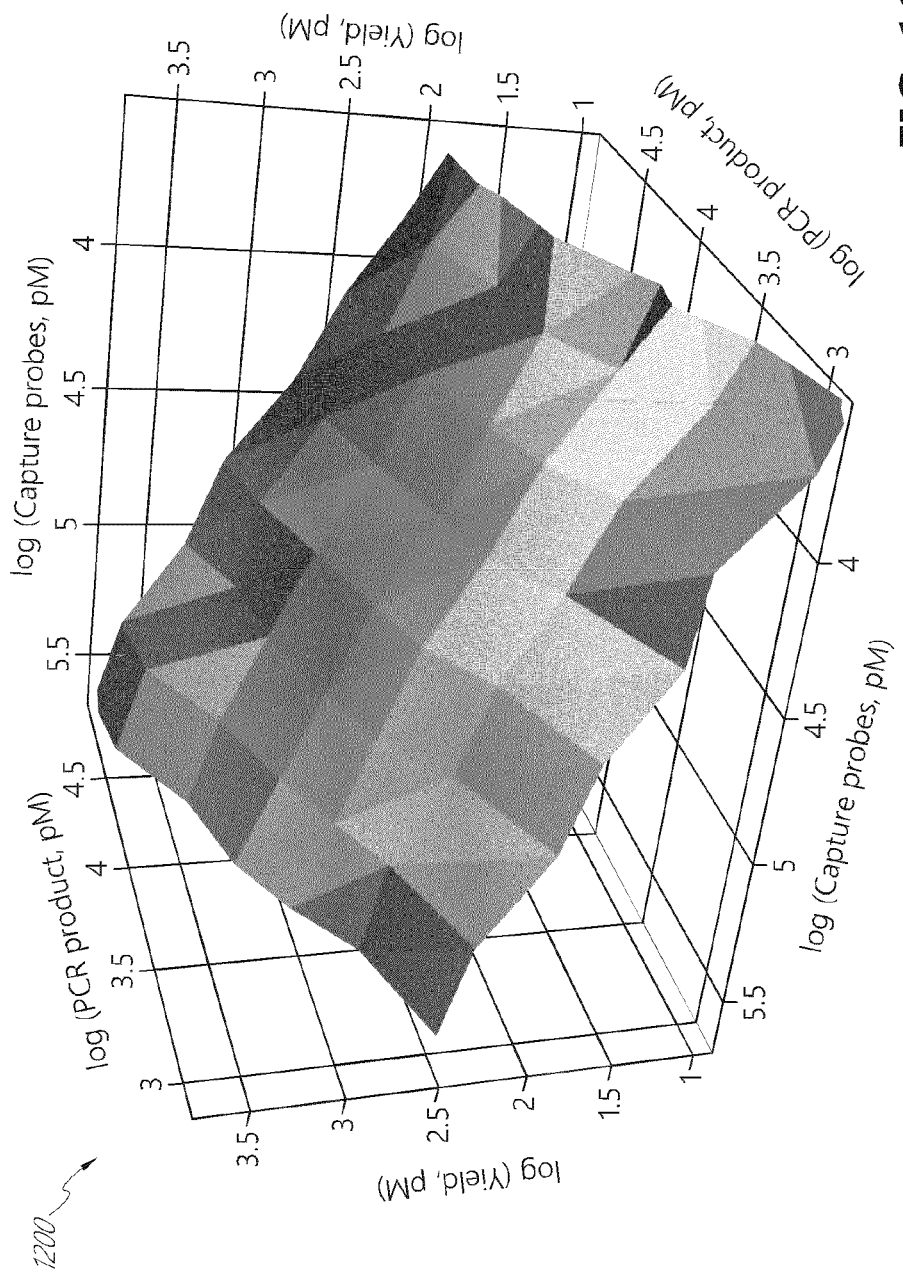
FIGS. 12A and 12B show a three dimensional plot of the predicted extended intermediate product yield and a plot of the predicted yield vs the actual yield based on PCR product and capture probe input.
Figure 12B:
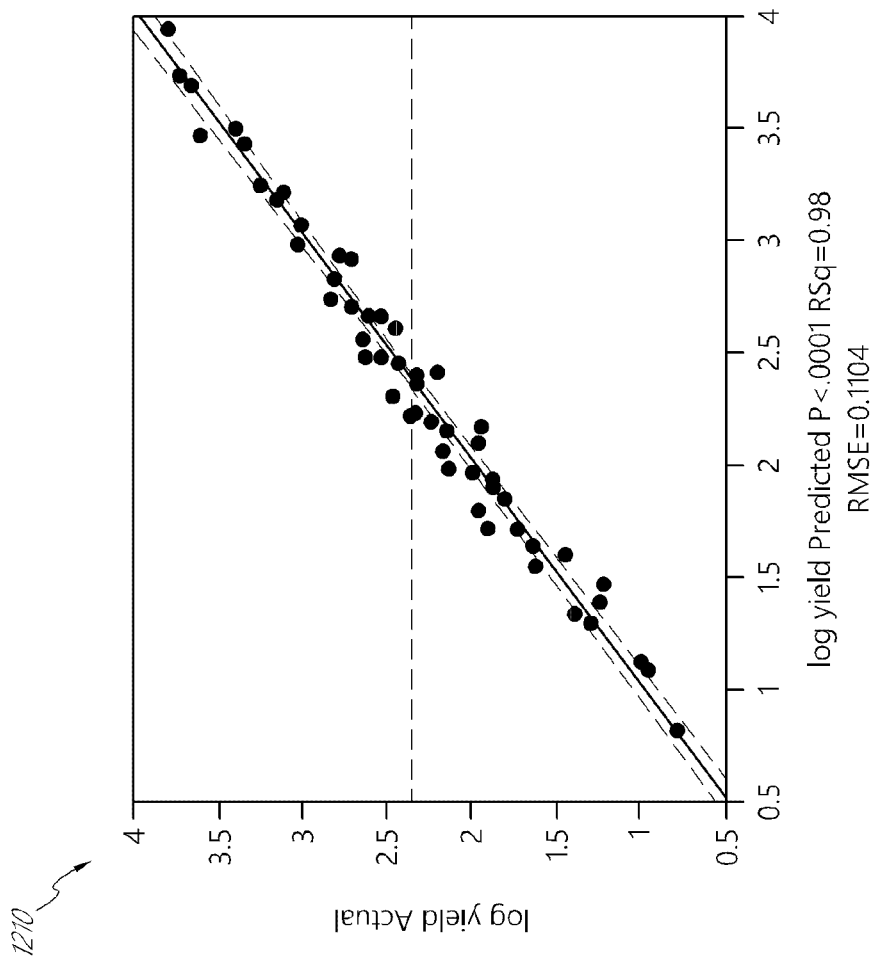

FIG. 12A shows a three dimensional plot 1200 of the hybridization and extension product yield. FIG. 12B shows a plot 1210 of the predicted yield vs the actual yield based on PCR product and capture probe input. Referring now to FIG. 12A, the data show dependency of hybridization and extension product yield on capture probes and PCR amplicon input concentration. Referring now to FIG. 12B, the plot shows correlation between actual yield (Y-axis) and yield predicted by mathematical equation described above. Good correlation between the two yields as shown in FIG. 12B is representative of good quality of the mathematical model and indicative of predictable and reproducible nature of the biochemical processes involved.

Example 4

Library (ExAmp) Normalization

This Example summarizes experimental results illustrating that the process of library normalization (step 645 of method 600 of FIG. 6) can be performed over a wide range of PCR product (amplicon) input by using a suitable amplification procedure such as kinetic exclusion amplification (KEA), also referred to as exclusion amplification (ExAmp). In this example, an ExAmp normalization reaction was used to substantially equalize sample quantities and adjust the concentration of PCR product (amplicon) input for subsequent sequencing applications.

Figure 13:
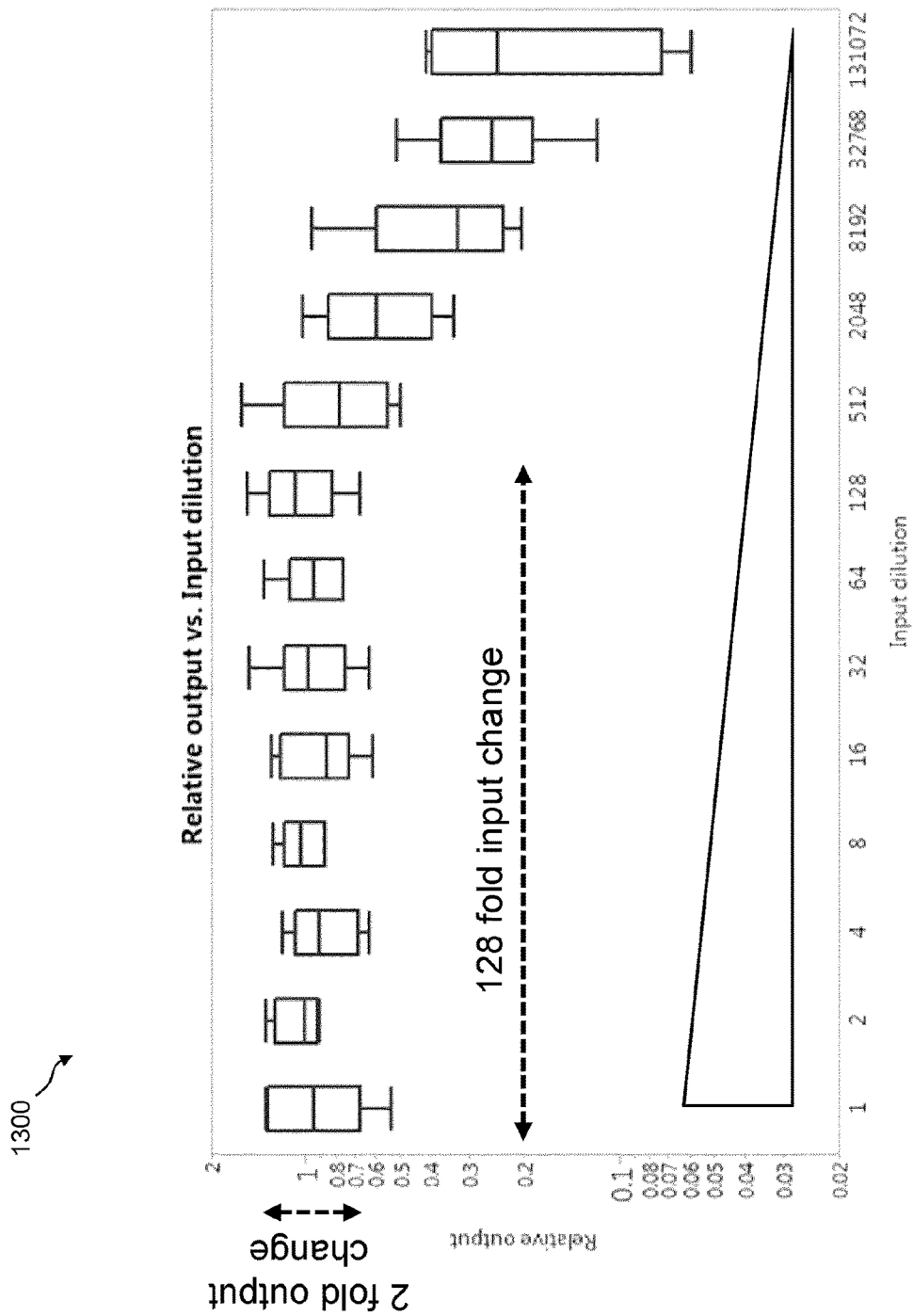
FIG. 13 shows a plot of the relative library output as a function of PCR product input in libraries prepared using the method of FIG. 6.

FIG. 13 shows a plot 1300 of the relative library output as a function of PCR product input in libraries prepared using method 600 of FIG. 6. The data show that the change in library output is relatively small compared to the change in PCR product input, e.g., there is about a 2-fold change in library output over a broad range of PCR product input concentrations (e.g., about a 128-fold change in PCR product input). The data also show that even beyond the 128-fold change in PCR product input that decrease in library output is relatively small relative to the change in PCR product input (e.g., about a 10-fold decrease in library output at about a 100,000-fold dilution in PCR product input).

Figure 14A:
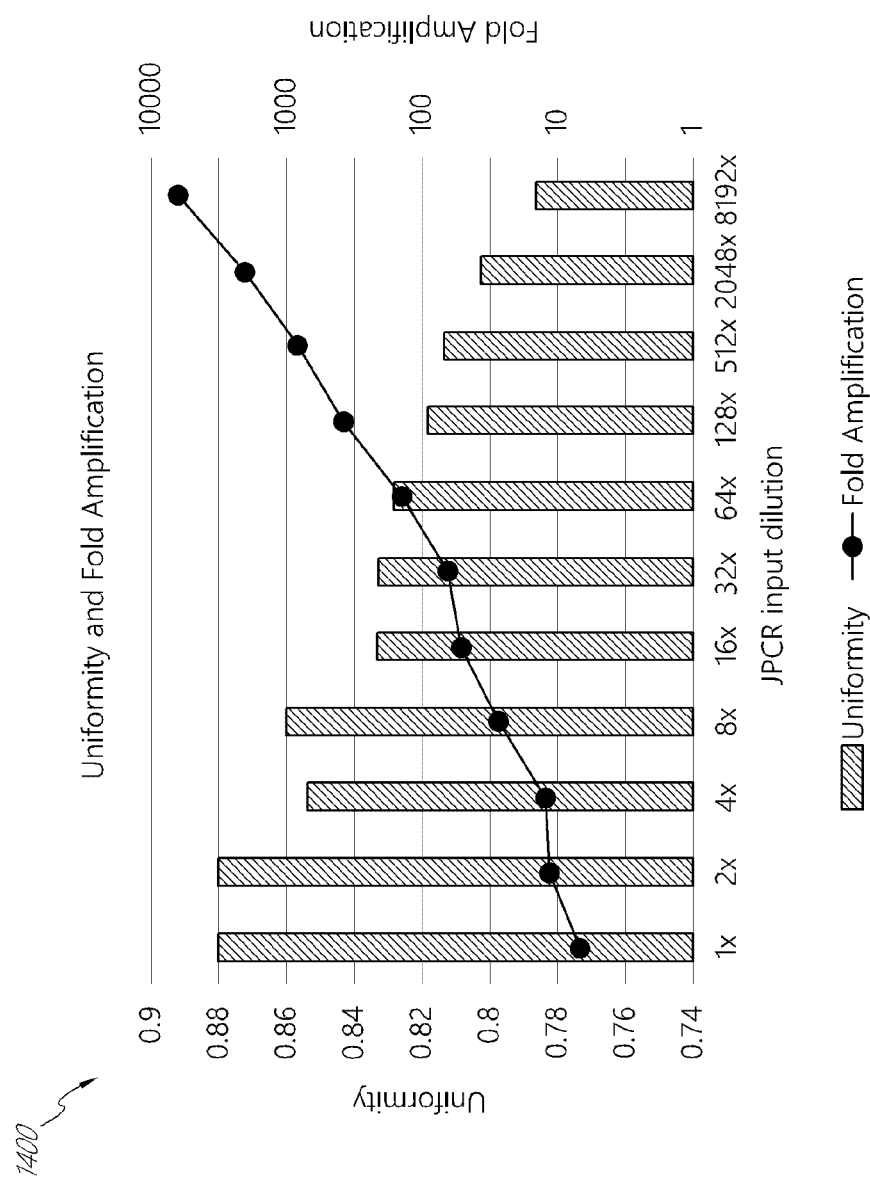
FIGS. 14A and 14B show a plot of library uniformity and fold amplification as a function of PCR product input (input dilution) and a plot of amplification bias, respectively, in libraries prepared using the method of FIG. 6.
Figure 14B:
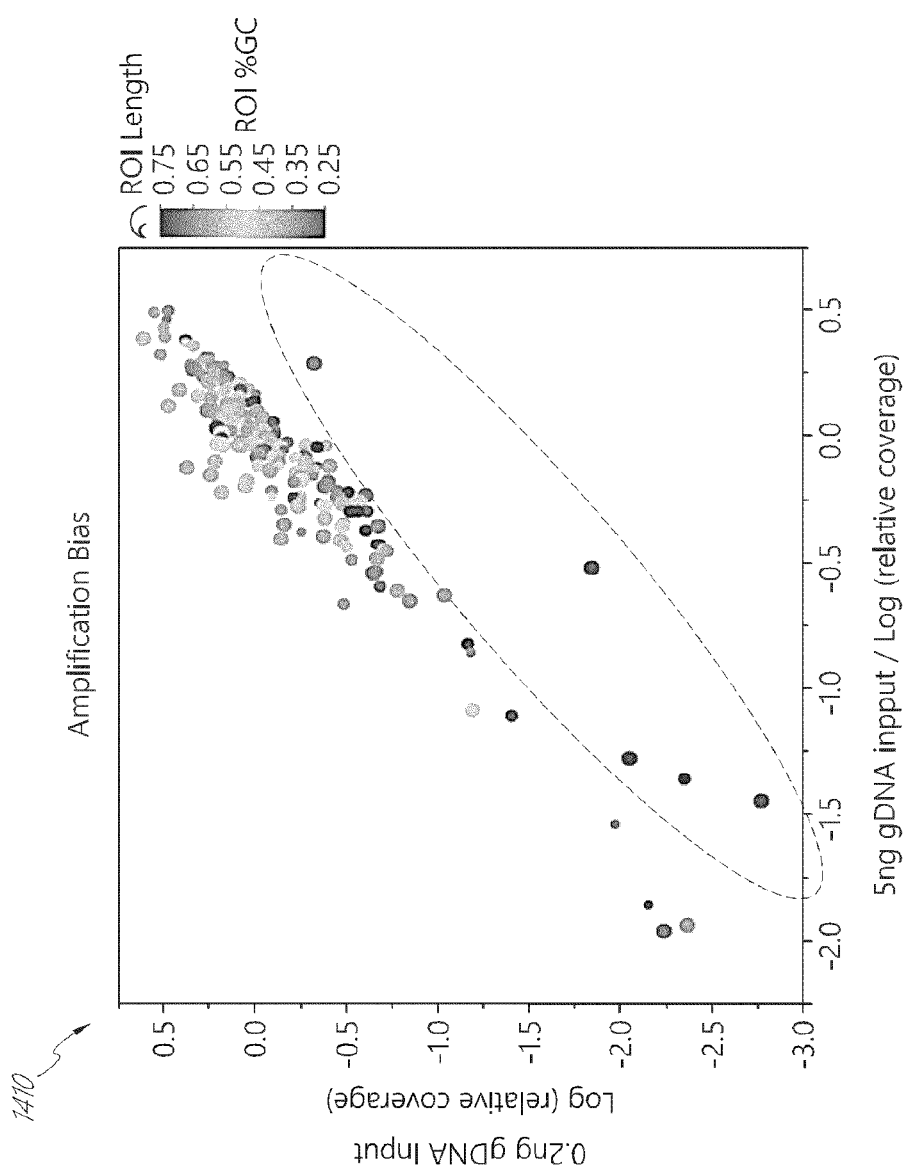

FIGS. 14A and 14B show a plot 1400 of library uniformity and fold amplification as a function of PCR product input (input dilution) and a plot 1410 of amplification bias, respectively, in libraries prepared using method 600 of FIG. 6. Referring to plot 1400 of FIG. 14A, the data show that as PCR product input decreases, there is a slight decrease in library uniformity (bar graph). The data also show that as the fold amplification (line) increases, library uniformity decreases. By minimizing the fold amplification during library normalization (e.g., targeting from about 10 to about 20 fold amplification), the effect on library uniformity can be substantially avoided.

Referring to plot 1410 of FIG. 14B, the data show correlation of library members coverage for two different DNA input quantities. Several library members that deviate from diagonal correlation are highlighted in dashed ellipse. This is indicative of amplification bias where these particular library members are not efficiently amplified. Overlaying amplicon GC content information, defined as fraction of amplicon DNA sequence consisting of dG or dC bases and shown as dot shade, shows all highlighted library members with amplification bias has high amplicon GC content.

Figure 15A:
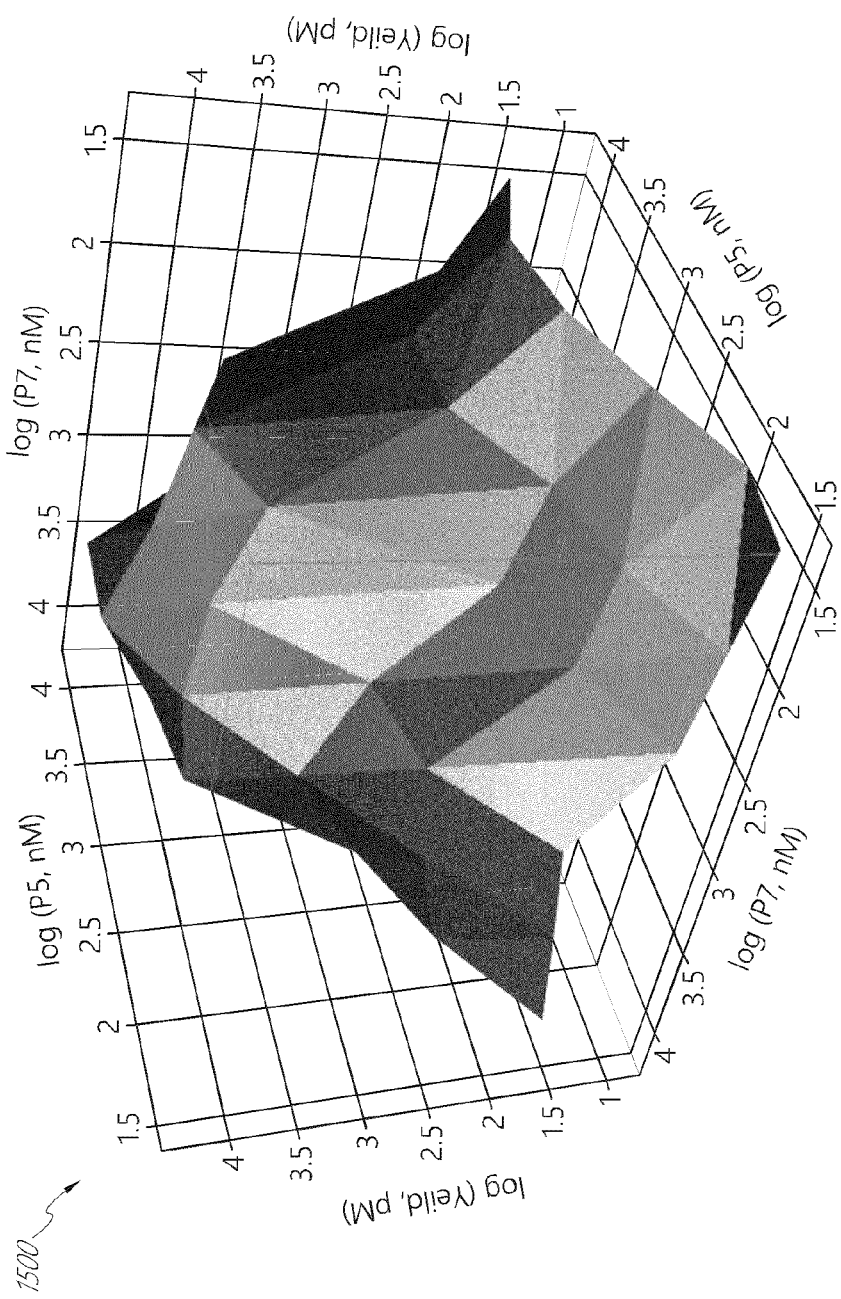
FIGS. 15A and 15B show a three dimensional plot of ExAmp yield and a plot of predicted vs. actual ExAmp yield as a function of P5 primer and P7-biotin primer concentrations.
Figure 15B:
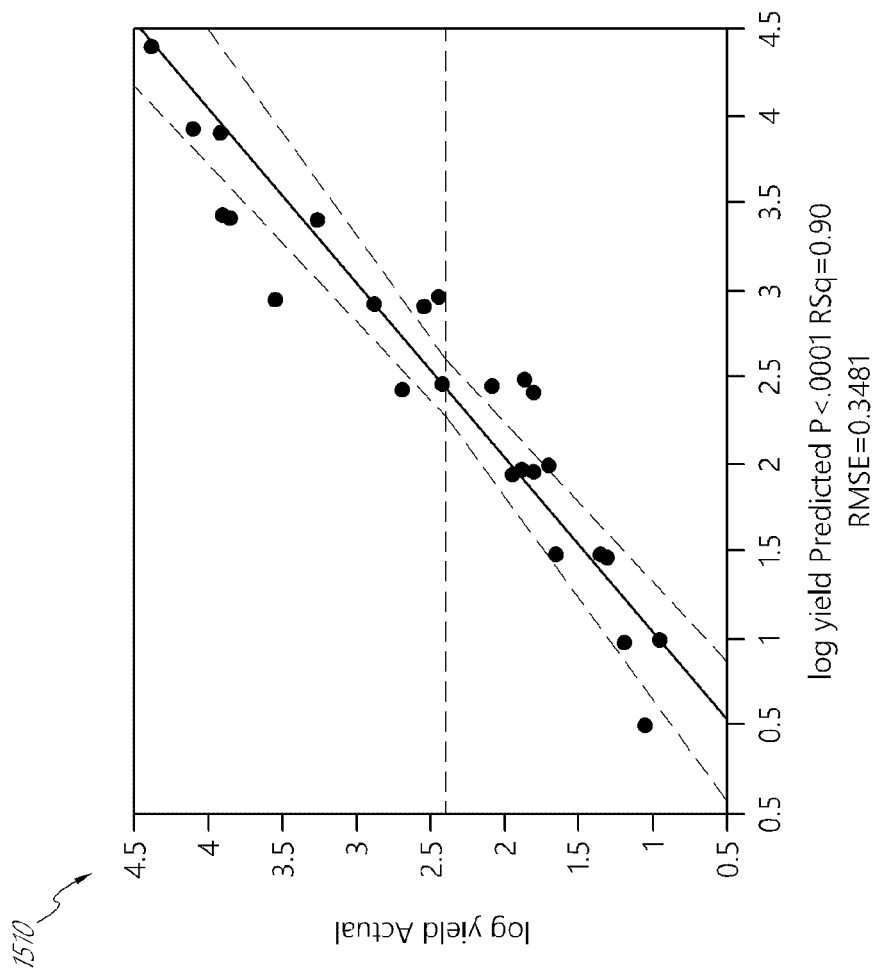

FIGS. 15A and 15B show a three dimensional plot 1500 of ExAmp yield and a plot 1510 of predicted vs. actual ExAmp yield as a function of P5 primer and P7-biotin primer concentrations. Referring to FIG. 15A, plot 1500 shows dependency of ExAmp amplification product yield on concentration of P5 and biotin-P7 primers. The data shows that yield can be modulated by changing both P5 and biotin-P7 concentrations.

Referring to FIG. 15B, plot 1510 shows correlation between actual ExAmp normalization yield and yield predicted by mathematical equation derived from the data on plot 1500. The predicted ExAmp normalization yield can be described as a function of P5 and P7-biotin primer concentrations by the following equation:

$$\log(\text{yield[pM]}) = 3.7974 + 1.0340 \cdot \log(P5 \text{ conc.}[\mu M]) + 1.0014 \cdot \log(P7\text{-biotin conc.}[\mu M]).$$

Example 5

Library Elution Efficiency

Table 3 below shows the effect of buffer composition, temperature, and incubation time on the efficiency of library elution from streptavidin beads (step 650 of method 600 of FIG. 6). The highest elution efficiency was achieved using a TE+Tween elution buffer at a temperature of 95° C. and an incubation time of 3 minutes. The data presented in Table 3 also show that the elution was robust both to times shorter than 3 min and temperature lower than 95° C.

TABLE 3

Streptavidin beads biotin elution efficiency

|  | 1 min | 2 min | 3 min | 4 min | 5 min |
|---|---|---|---|---|---|
| TE with Tween |  |  |  |  |  |
| 95 C. | 106% | 105% | 110% | 102% | 99% |
| 90.2 C. | 97% | 98% | 101% | 94% | 93% |
| 84.4 C. | 91% | 93% | 95% | 90% | 89% |
| 79.1 C. | 84% | 86% | 89% | 85% | 85% |
| 75.1 C. | 76% | 82% | 84% | 81% | 82% |
| 70 C. | 67% | 71% | 76% | 76% | 77% |
| Water |  |  |  |  |  |
| 95 C. | 100% | 103% | 102% | 99% | 90% |
| 90.2 C. | 97% | 101% | 101% | 97% | 90% |
| 84.4 C. | 94% | 99% | 98% | 96% | 90% |
| 79.1 C. | 89% | 96% | 94% | 92% | 89% |
| 75.1 C. | 80% | 91% | 90% | 90% | 86% |
| 70 C. | 70% | 77% | 82% | 84% | 81% |
| HT1 |  |  |  |  |  |
| 95 C. | 99% | 105% | 101% | 98% | 75% |
| 90.2 C. | 73% | 86% | 84% | 86% | 69% |
| 84.4 C. | 38% | 53% | 54% | 57% | 47% |
| 79.1 C. | 11% | 16% | 21% | 21% | 18% |
| 75.1 C. | 4% | 5% | 9% | 7% | 9% |
| 70 C. | 2% | 2% | 4% | 3% | 4% |

Figure 16:
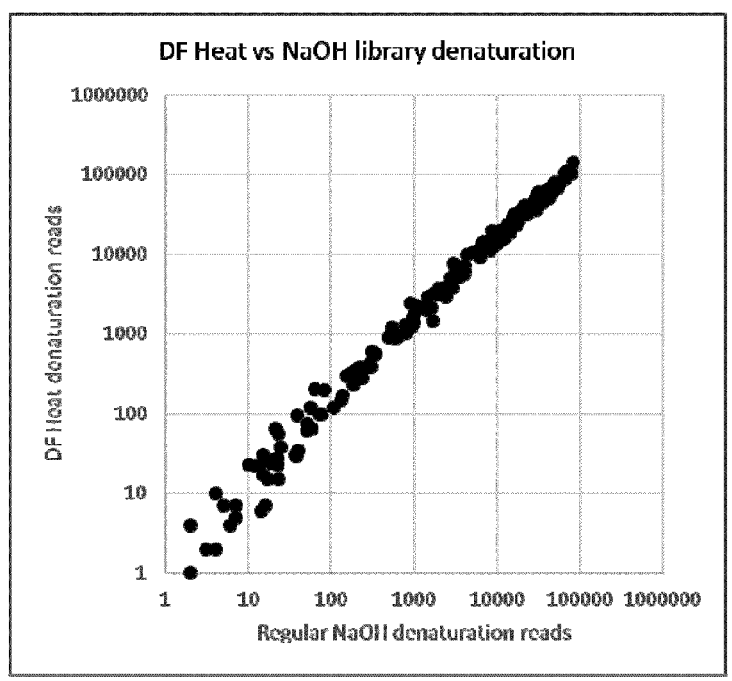
FIG. 16 shows a plot of per target sample reads obtained from samples eluted from streptavidin beads using heat denaturation on a droplet actuator and samples that has been additionally denatured by NaOH treatment on bench.

FIG. 16 shows a plot 1600 of correlation between the library-per-target coverage obtained from libraries eluted from streptavidin beads using heat denaturation on a droplet actuator and the same libraries subsequently denatured by standard NaOH treatment. Plot 1600 shows good correlation, demonstrating that subsequent NaOH denaturation was not needed and that library was fully and efficiently denatured by head on-actuator.

Example 6

Library Uniformity Versus Genomic Input

To evaluate library uniformity as a function of genomic DNA input, 5 libraries were prepared using method 600 of FIG. 6 and 5 different genomic DNA samples.

Figure 17:
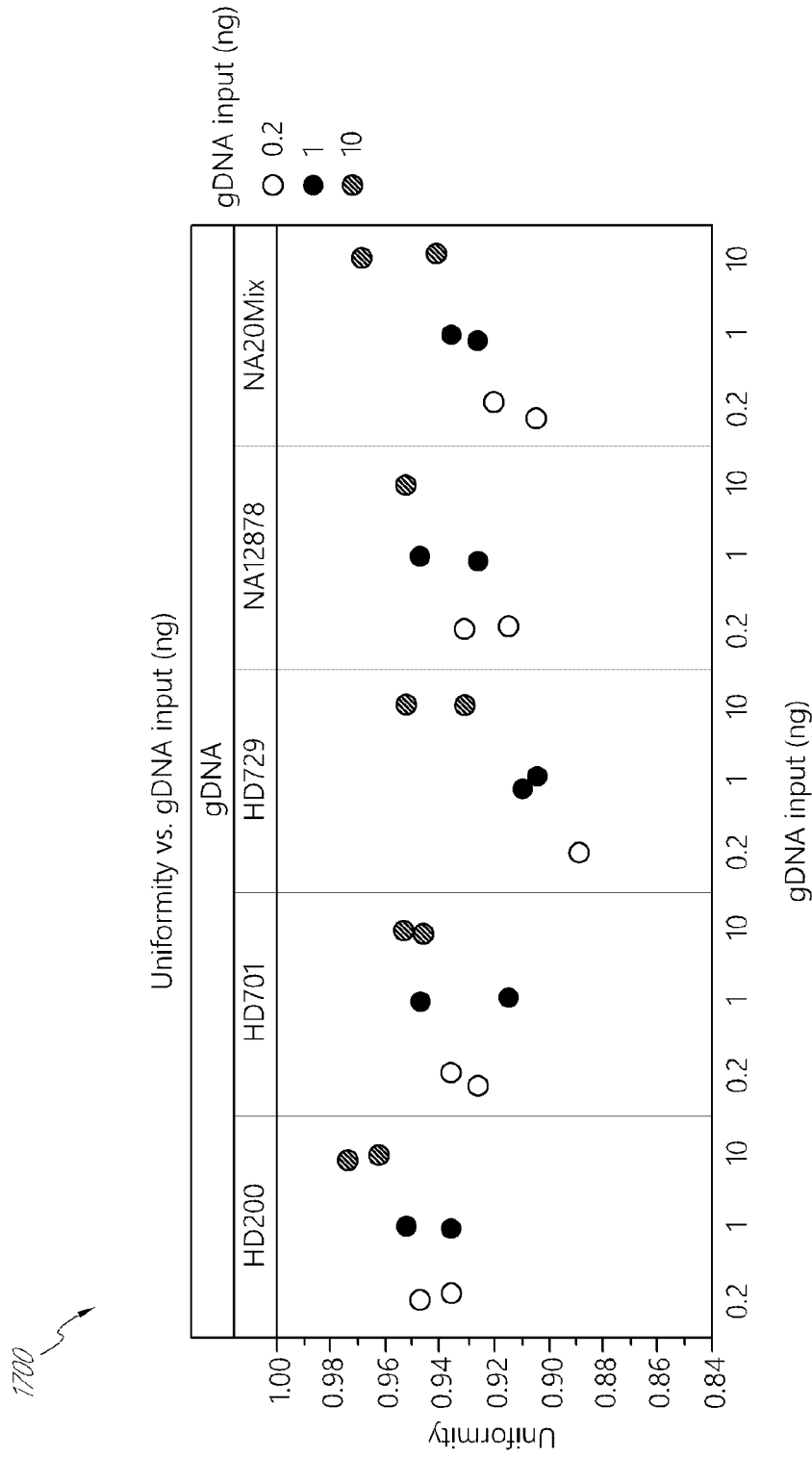
FIG. 17 shows a plot of library uniformity as a function of genomic DNA input for 5 different samples.

FIG. 17 shows a plot 1700 of library uniformity as a function of genomic DNA input for 5 different libraries prepared in accordance with some embodiments of the disclosure. The libraries were prepared using 0.2, 1, and 10 ng of 5 different genomic DNA samples (HD200, HD701, HD729, NA12878, and NA20Mix genomic DNA samples) and MJ191-plex target-specific primer pool. Typically, genomic DNA sample input of 1 ng corresponds to about 300 genomes, 0.2 ng corresponds to about 60 genomes, and 10 ng corresponds to about 3000 genomes. The data presented at FIG. 17 show good uniformity (>90% for most libraries) across all genomic DNA samples and input ranges examined. Specificity across all genomic DNA samples was >95%. In this experiment, the specificity was defined as the percentage of filtered reads corresponding to the intended targets.

Example 7

Variant Calling Accuracy

To evaluate the accuracy of variant calling in libraries prepared using method 600 of FIG. 6, the correlation between expected and observed variant frequencies for certain alleles was determined for the NA20mix and HD200 libraries of FIG. 17.

Figure 18A:
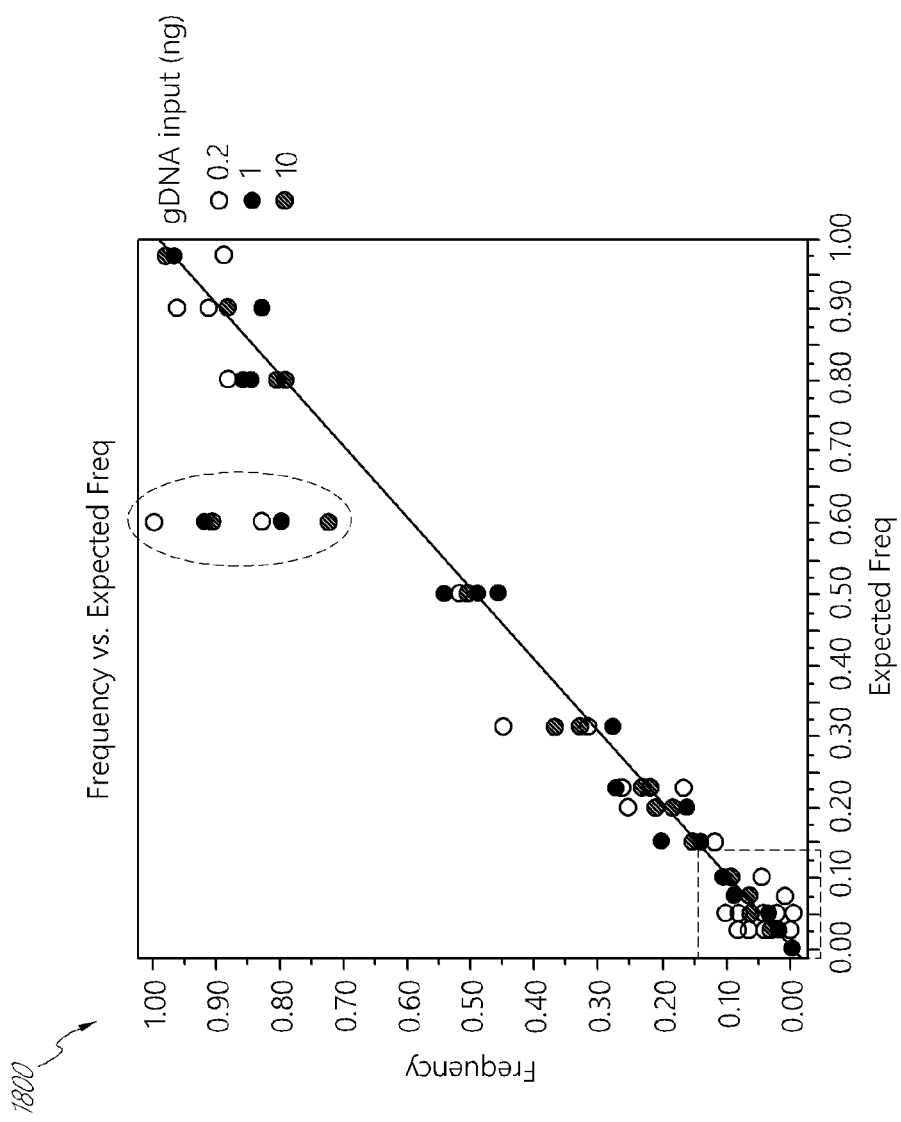
FIGS. 18A and 18B show a plot of TP (true positive) variant calling accuracy in the NA20mix samples and a plot of TP variant calling accuracy in the HD200 sample, respectively, of FIG. 17.
Figure 18B:
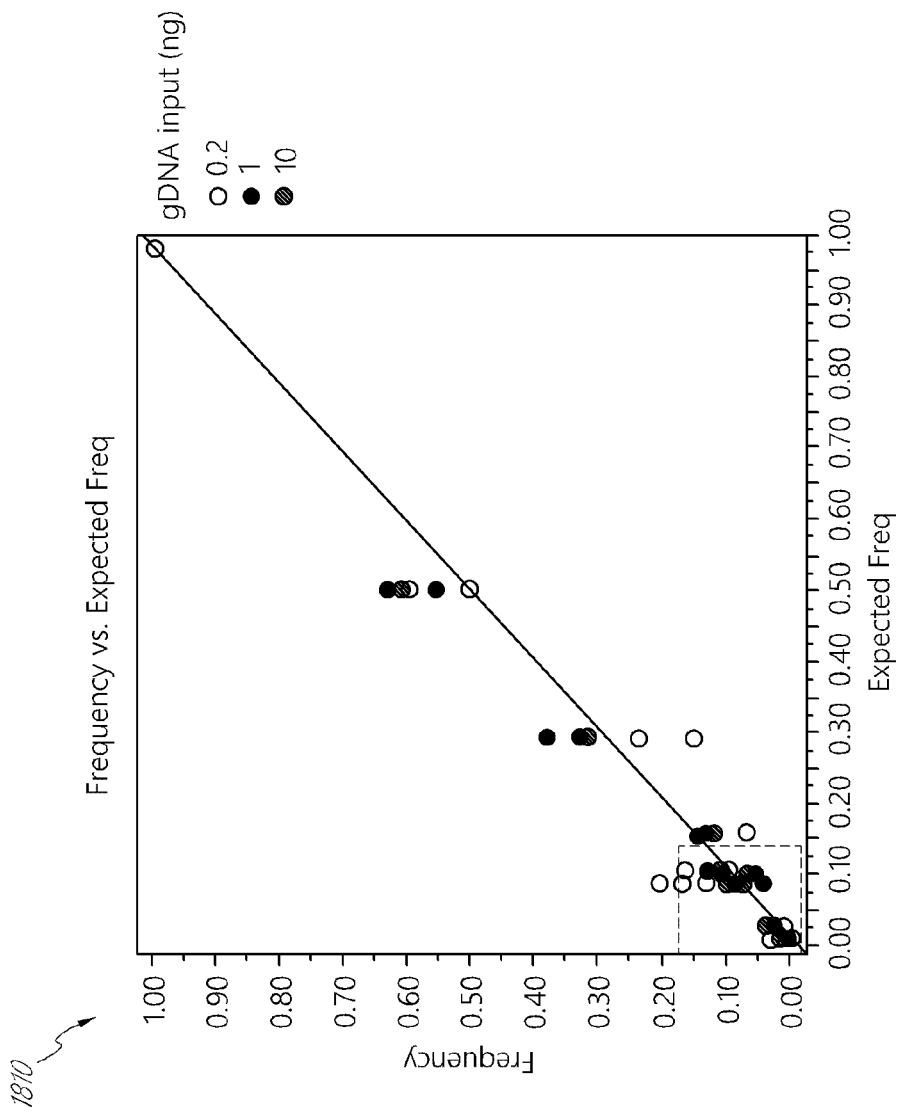

FIGS. 18A and 18B show a plot 1800 of TP (true positive) variant calling accuracy in the NA20mix library described in FIG. 17 and a plot 1810 of TP variant calling accuracy in the HD200 library described in FIG. 17, respectively. The data show, for example, that for 1 ng (e.g., about 300 genome equivalents) input, there is a good correlation between the expected variant frequency and observed variant frequency for TP variant calling in both the NA20mix and HD200 libraries. Referring to FIGS. 18A and 18B, the boxed areas represent about less than 30 copies of the genome for lng of gDNA input (e.g., less than 30 copies of those specific variants/mutations). Some of the boxed variants correspond to as low as 7 or 3 genome copies per lng gDNA input and demonstrate the sensitivity of the digital fluidic system and method for accurate variant calling using relatively low genomic DNA input. Circled area in FIG. 18A corresponds to particular variant that was detected at frequency higher than expected. This is attributed to low reads coverage on this particular target resulting in increased noise.

Figure 19A:
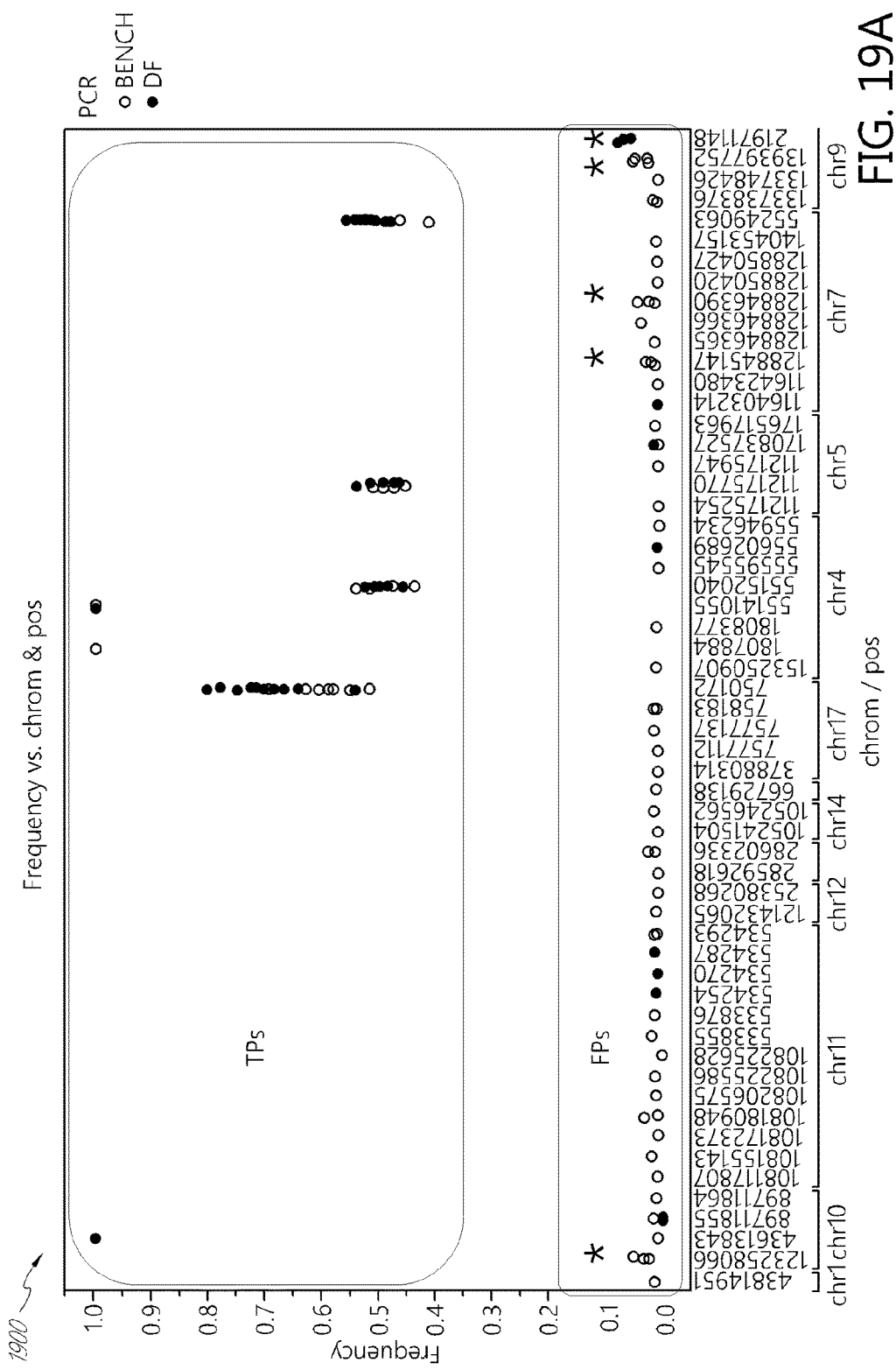
FIG. 19A shows a plot of the TP and FP (false positive) variant frequency as a function of chromosome and position in genomic libraries prepared using an on-bench protocol and on-actuator using the method of FIG. 6.

FIG. 19A shows a plot 1900 of the TP and FP (false positive) variant frequency as a function of chromosome and position in genomic libraries prepared using an on-bench protocol and on-actuator using method 600 of FIG. 6. Libraries (e.g., 19 digital fluidic (on-actuator) samples and 9 on-bench samples) were prepared using 1 ng input NA12878 genomic DNA and the MJ191-plex target-specific primer pool. In the NA12878 genome, there are 7 true positive variants. The data show that all TP variants were accurately called in both the on-bench and on-actuator samples. The data also show the frequency of random and persistent (indicated by an asterisk) FP variants that were called in either all the on-bench or all the on-actuator samples. The frequency of the FP variant calls is substantially lower than the frequency of TP variant calls. Additionally, sequencing base quality is often, but not always, substantially lower for FP variants relative to TP variants indicative of sequencing noise. FP variants can be removed, for example, during analysis by filtering using both these criteria. It is apparent that on-actuator method results in fewer FP variants than on-bench method.

Figure 19B:
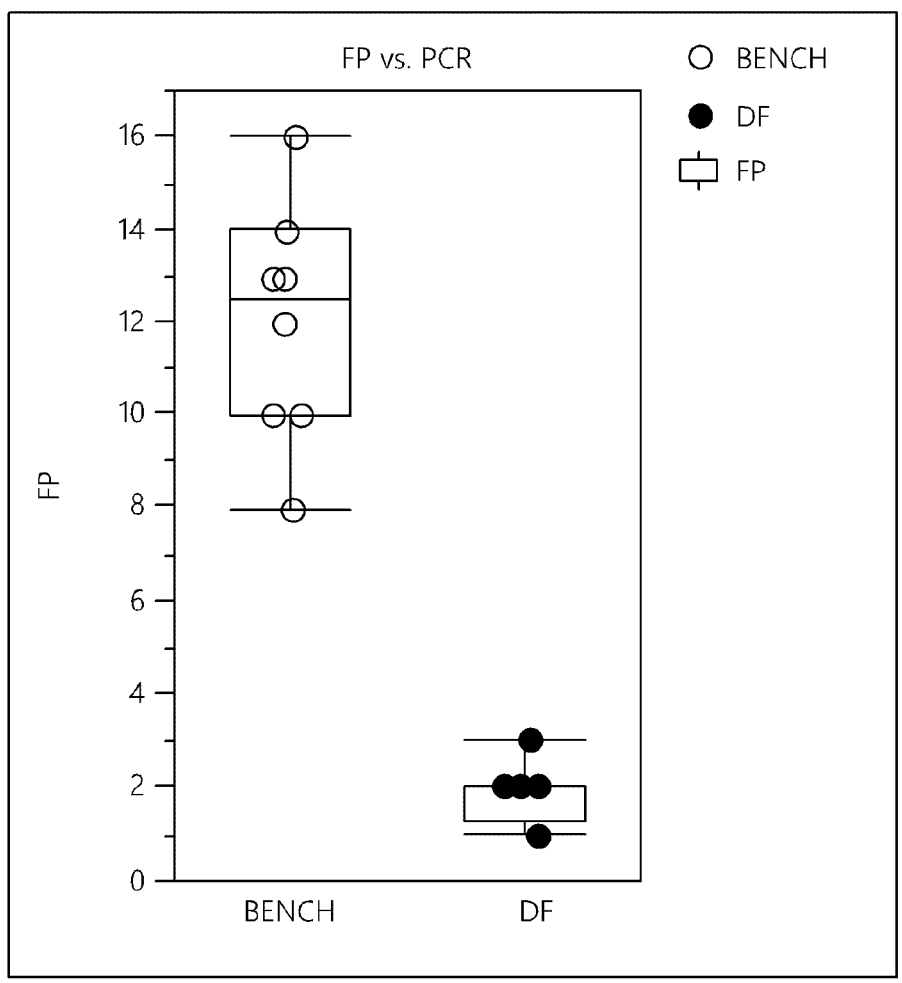
FIG. 19B shows a plot of the average number of FP variant calls in the on-bench samples and the on-actuator samples of FIG. 19A.

FIG. 19B shows a plot 1910 of the average number of FP variant calls in the on-bench samples and the on-actuator samples of plot 1900 of FIG. 19A. The data show that on average, there were about 12 FP variants called in the on-bench samples compared to about 2 FP variants called in the on-actuator samples. The lower FP variant call rate in the samples prepared on-actuator compared to the samples prepared on-bench may be due, in part, to the differences in the PCR step(s) of the library preparation protocols. For example, the on-bench library preparation protocol used a combined target-specific and universal PCR reaction of about 30 cycles for amplification of the input genomic DNA. The on-actuator library preparation protocol used a first target-specific amplification of about 4 to about 6 cycles (step 615 of method 600 of FIG. 6) and a second universal amplification (step 620 of method 600 of FIG. 6) of about 14 cycles for amplification of the input genomic DNA (e.g., total PCR of about 20 cycles or less). Lower total number of PCR cycles is possible to achieve in on-actuator protocol due to improved PCR and biochemistry efficiency.

Example 8

Amplicon Scalability

To evaluate library uniformity as a function of the complexity of target-specific primer pools, targeted amplicon libraries were prepared using method 600 of FIG. 6 and 5 different multiplexed primer pools. Libraries were prepared using 1 and 5 ng of NA12878 and NA20Mix genomic DNA and a 192-plex primer pool (Pool 1; 192 targets), or a second 192-plex primer pool (Pool 2; 192 targets), or a 196-plex primer pool (Pool 3; 193 targets), or a 384-plex combined primer pool (Pool Mix 1 to 2; 384 targets), or a 580-plex combined primer pool (Pool Mix 1 to 3; 580 targets).

Figure 20:
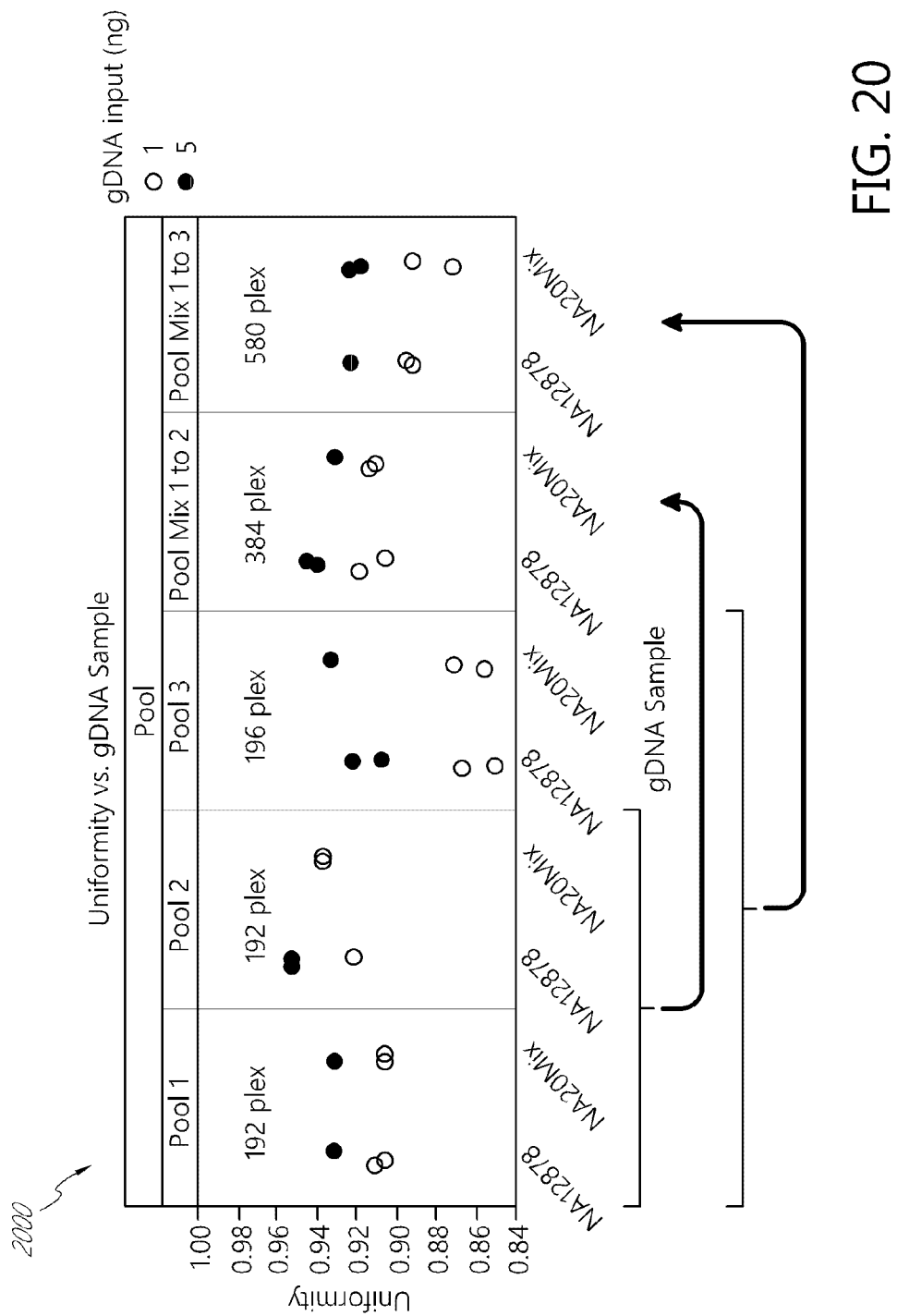
FIG. 20 shows a plot of library uniformity as a function of genomic DNA and primer pool complexity.

FIG. 20 shows a plot 2000 of library uniformity as a function of genomic DNA and primer pool complexity. In plot 2000, the data show good uniformity (most libraries >90%) for both genomic DNA samples and input amounts. The data also show that as the complexity of the primer pool increased from a lower complexity (e.g., 192- or 196-plex) to a higher complexity (e.g., 384- or 580-plex), there was relatively little change in uniformity.

Uniformity for samples prepared on-bench (data not shown) was about 70% for pool mix 1 to 3. The higher uniformity in libraries prepared on-actuator (about 90%) compared to on-bench uniformity (about 70%) provides for more efficient library coverage in sequencing (e.g., decreases sequencing depth by about an order of magnitude). Specificity for all genomic DNA samples and primer pools was about 95%.

Figure 21A:
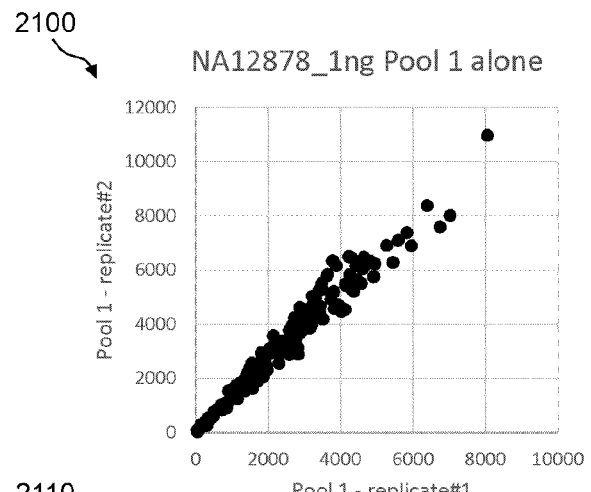
FIGS. 21A, 21C, and 21B show a plot of target coverage in the 192-plex Pool 1 library, a plot of 192-plex Pool 1 target coverage in the 384-plex Pool Mix 1-2 library, and a plot of 192-plex Pool 1 target coverage in the 580-plex Pool Mix 1-3 library described in FIG. 20.
Figure 21B:
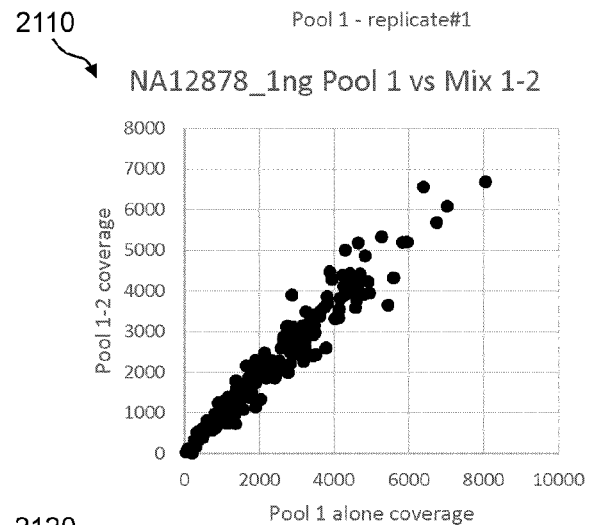
Figure 21C:
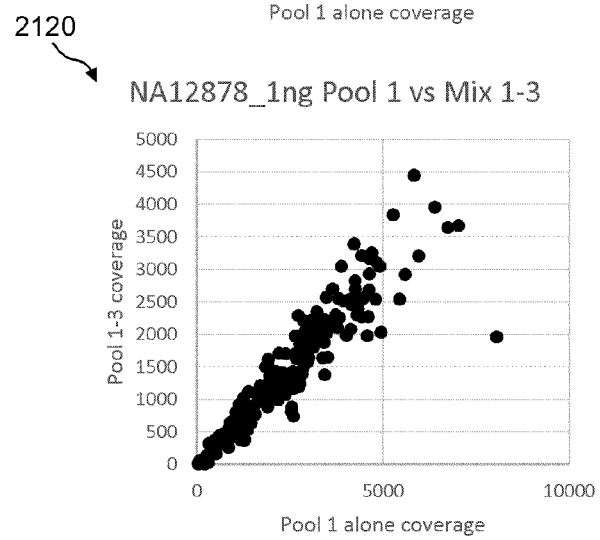

FIGS. 21A, 21B, and 21C show a plot 2100 of target coverage in the 192-plex Pool 1 library, a plot 2110 of 192-plex Pool 1 target coverage in the 384-plex Pool Mix 1-2 library, and a plot 2120 of 192-plex Pool 1 target coverage in the 580-plex Pool Mix 1-3 library described in plot 2000 of FIG. 20.

The data show that when the complexity of a library increases (e.g., increased target-specific primer pairs and genomic targets in Pool Mix 1-2 and Pool Mix 1-3 libraries), there is a relatively small effect on the coverage of the 192-plex Pool 1 library targets.

Example 9

Systems

Figure 22:
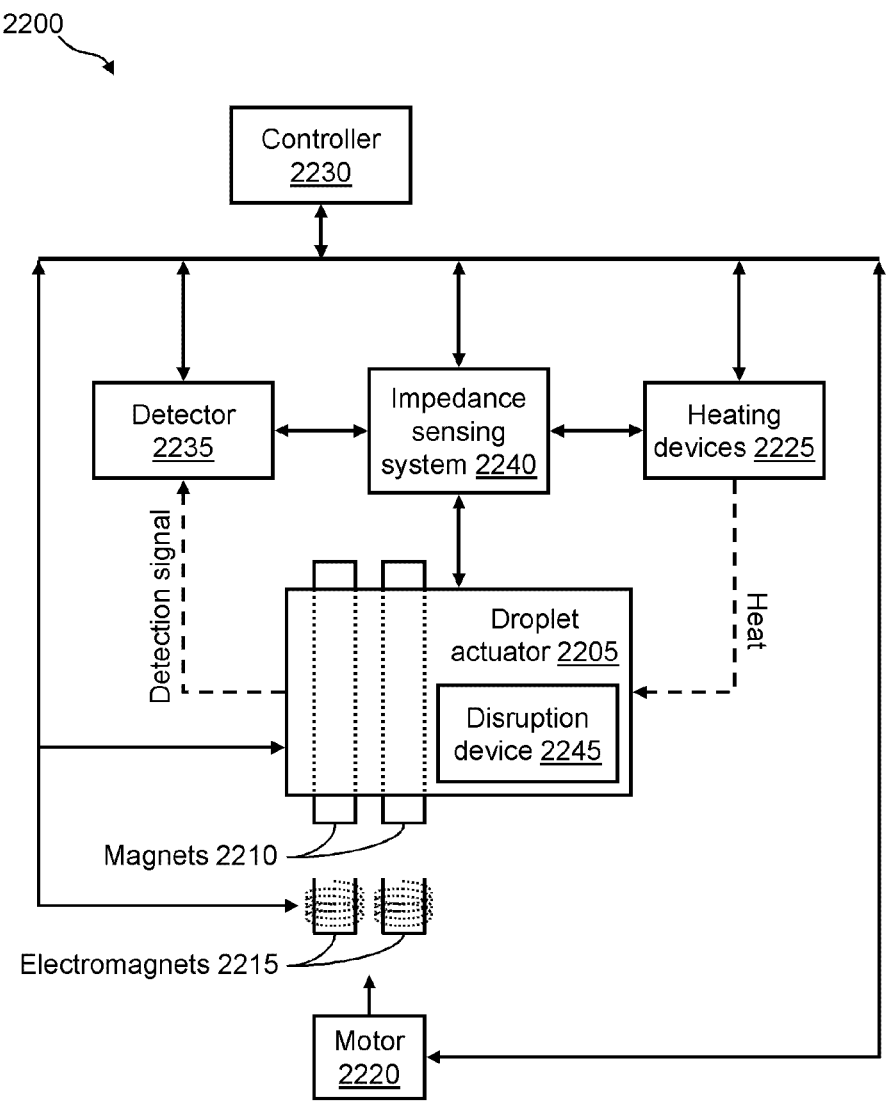
FIG. 22 illustrates a functional block diagram of a non-limiting example of a microfluidics system that includes a droplet actuator, which is one example of a fluidics cartridge.
Figure 23:
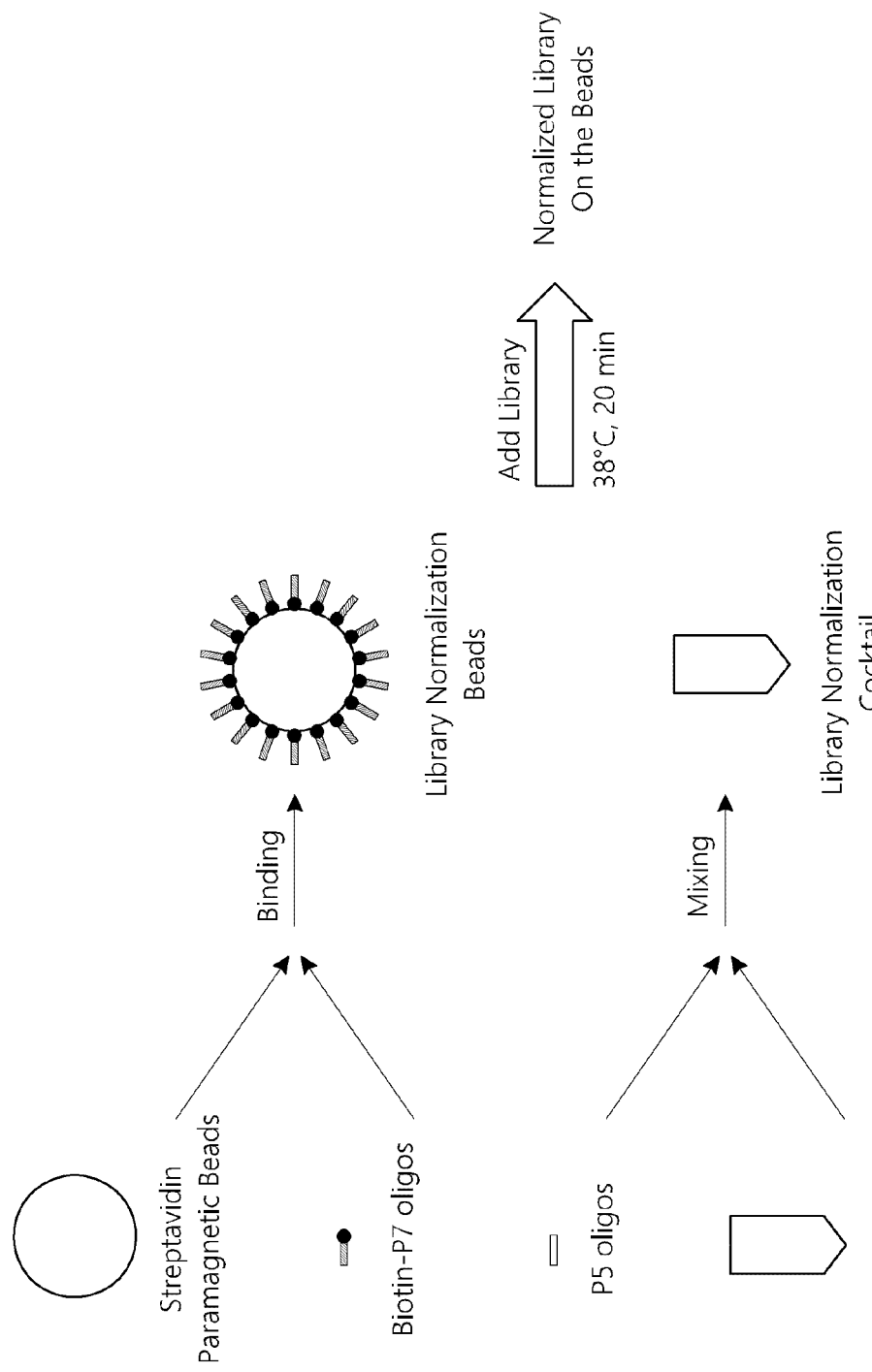
FIG. 23 graphically illustrates a non-limiting example of a method of using Ex-Amp reagents for nucleic acid amplification and normalization in accordance with some embodiments of the disclosure.
Figure 24:
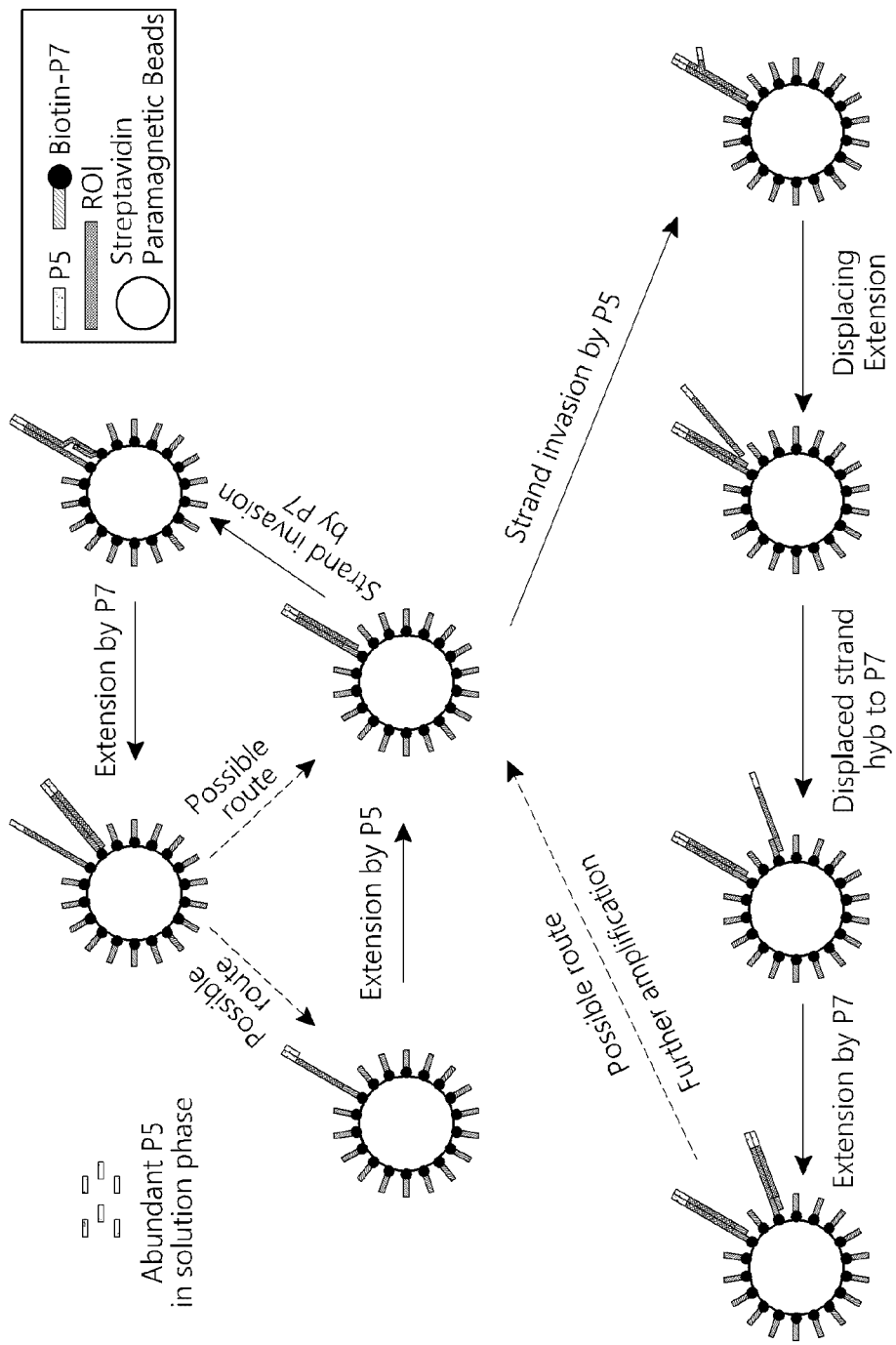
FIG. 24 illustrates another non-limiting example of a method of using Ex-Amp reagents for nucleic acid amplification and normalization in accordance with some embodiments of the disclosure. Depending on the specific workflow, extendable primers used in this exemplary method can be amplification primers or normalization primers. First amplification or normalization primers P7 immobilized on a solid phase support offer ability to normalize the nucleic acid samples and ease of purification, while second amplification or normalization primers P5 in solution phase offer fast kinetics.
Figure 25:
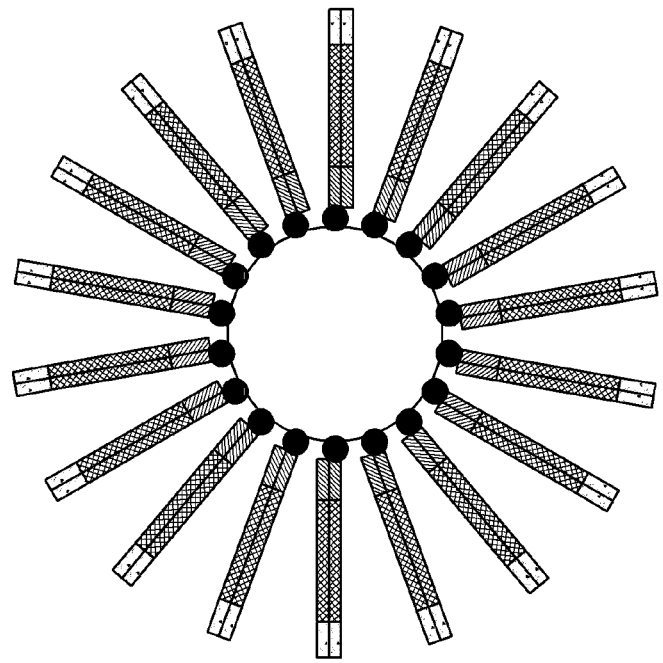
FIG. 25 graphically summarizes net effects of a non-limiting example of a method of nucleic acid amplification in accordance with some embodiments of the disclosure.
Figure 25:
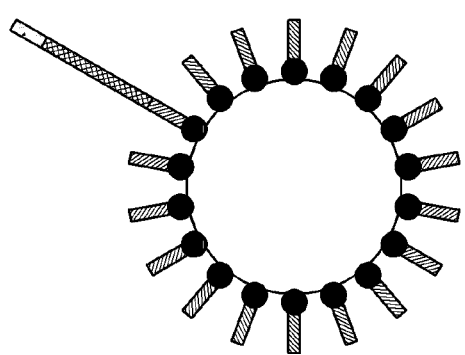
Figure 26:
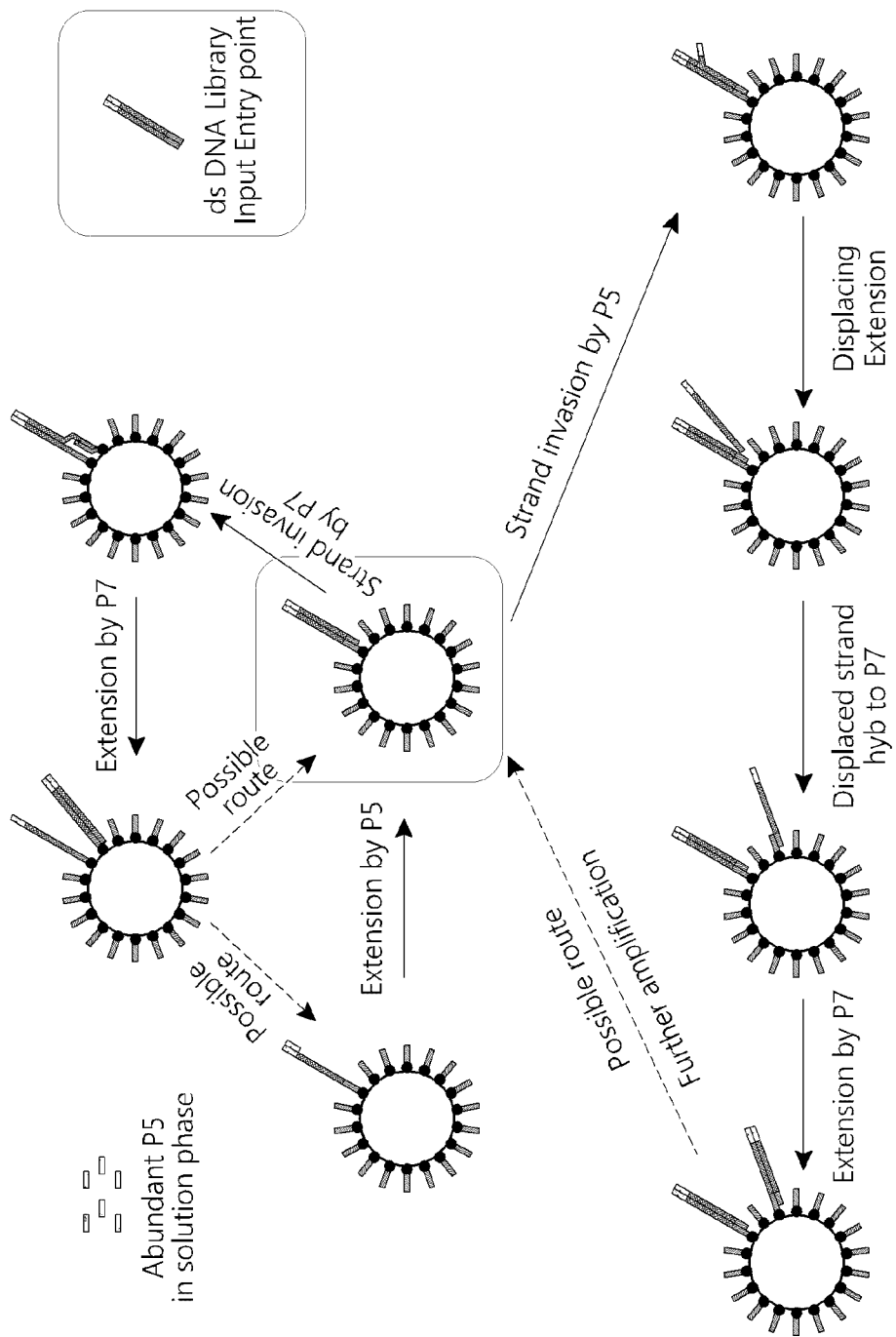
FIG. 26 illustrates a non-limiting example of a method of nucleic acid amplification and normalization in accordance with some embodiments of the disclosure, in which the input sample contains double-stranded nucleic acids. In this experiment, double-stranded DNA (dsDNA) enters the reaction core by strand invasion, either by first amplification or normalization primer P5 in solution phase or by second amplification or normalization primer P7 immobilized to bead surface (indicated by a boxed bead).
Figure 27:
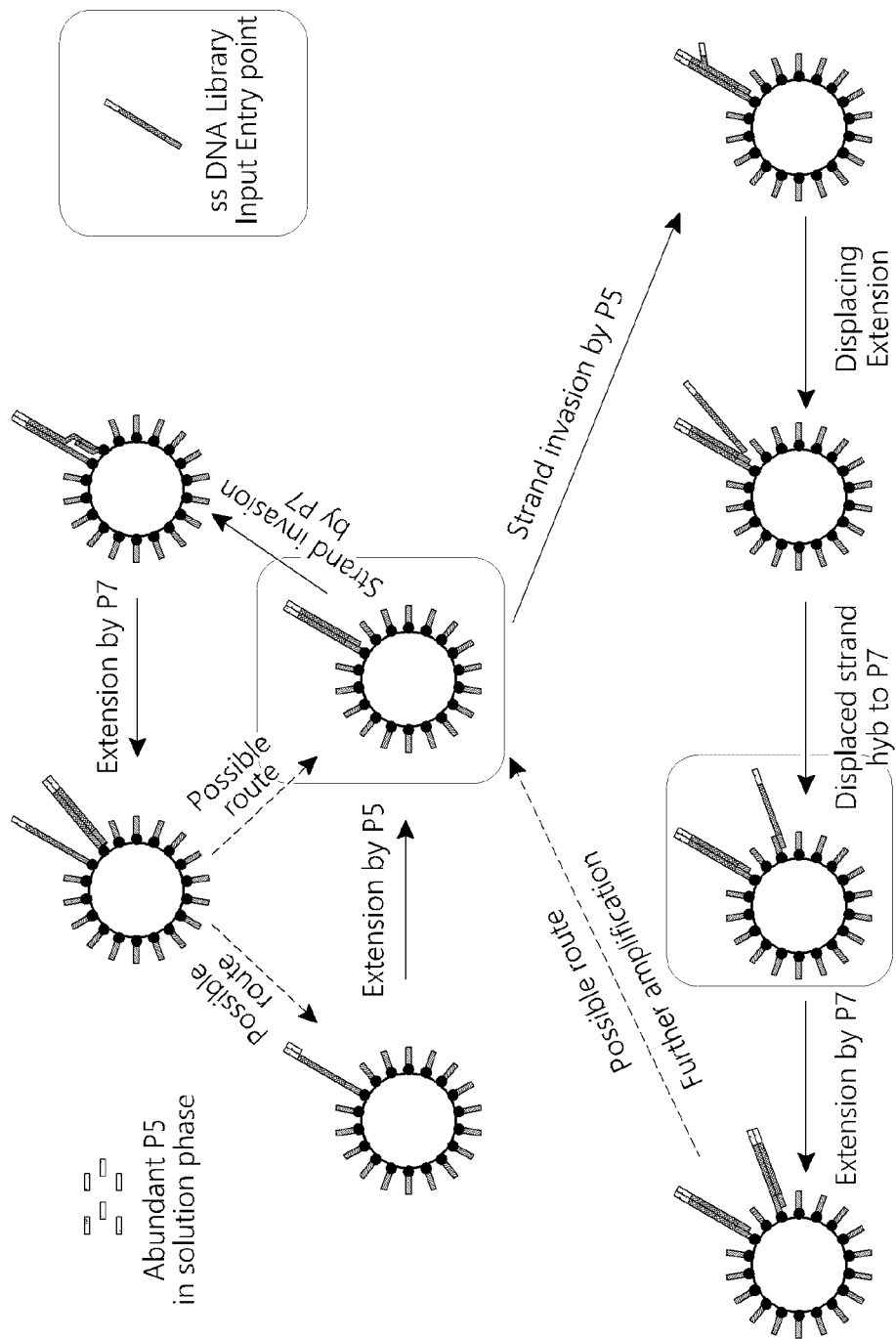
FIG. 27 illustrates a non-limiting example of a method of nucleic acid amplification and normalization in accordance with some embodiments of the disclosure, in which the input nucleic acid sample contains single-stranded nucleic acids such as, for example, single-stranded DNA (ssDNA). Single-stranded DNA enters either by hybridization to primer P7 immobilized to bead surface or by being converted into dsDNA by primer P5 in solution phase (indicated by boxed beads).
Figure 28:
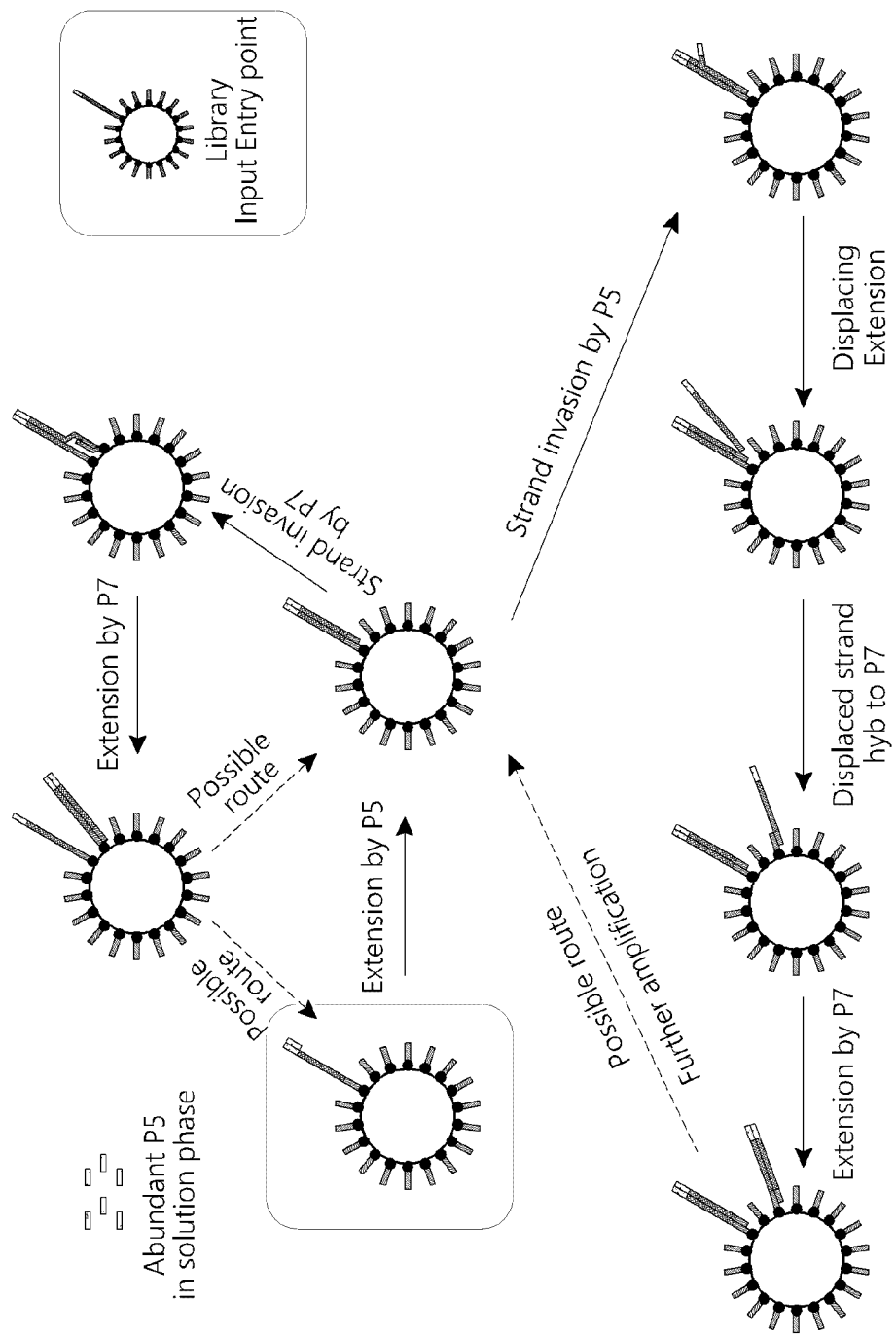
FIG. 28 illustrates another non-limiting example of a method of nucleic acid amplification and normalization in accordance with some embodiments of the disclosure. The input nucleic acid sample, which contains nucleic acids already affixed onto beads (boxed), enters the reaction core by hybridizing to primer P5 in solution phase.

FIG. 22 illustrates a functional block diagram of an example of a microfluidics system 2200 that includes a droplet actuator 2205, which is one example of a fluidics cartridge. Digital microfluidic technology conducts droplet operations on discrete droplets in a droplet actuator, such as droplet actuator 2205, by electrical control of their surface tension (electrowetting). The droplets may be sandwiched between two substrates of droplet actuator 2205, a bottom substrate and a top substrate separated by a droplet operations gap. The bottom substrate may include an arrangement of electrically addressable electrodes. The top substrate may include a reference electrode plane made, for example, from conductive ink or indium tin oxide (ITO). The bottom substrate and the top substrate may be coated with a hydrophobic material. Droplet operations are conducted in the droplet operations gap. The space around the droplets (e.g., the gap between bottom and top substrates) may be filled with an immiscible inert fluid, such as silicone oil, to prevent evaporation of the droplets and to facilitate their transport within the device. Other droplet operations may be effected by varying the patterns of voltage activation; examples include merging, splitting, mixing, and dispensing of droplets.

Droplet actuator 2205 may be designed to fit onto an instrument deck (not shown) of microfluidics system 2200. The instrument deck may hold droplet actuator 2205 and house other droplet actuator features, such as, but not limited to, one or more magnets and one or more heating devices. For example, the instrument deck may house one or more magnets 2210, which may be permanent magnets. Optionally, the instrument deck may house one or more electromagnets 2215. Magnets 2210 and/or electromagnets 2215 are positioned in relation to droplet actuator 2205 for immobilization of magnetically responsive beads. Optionally, the positions of magnets 2210 and/or electromagnets 2215 may be controlled by a motor 2220. Additionally, the instrument deck may house one or more heating devices 2225 for controlling the temperature within, for example, certain reaction and/or washing zones of droplet actuator 2205. In one example, heating devices 2225 may be heater bars that are positioned in relation to droplet actuator 2205 for providing thermal control thereof.

A controller 2230 of microfluidics system 2200 is electrically coupled to various hardware components of the apparatus set forth herein, such as droplet actuator 2205, electromagnets 2215, motor 2220, and heating devices 2225, as well as to a detector 2235, an impedance sensing system 1640, and any other input and/or output devices (not shown). Controller 2230 controls the overall operation of microfluidics system 2200. Controller 2230 may, for example, be a general purpose computer, special purpose computer, personal computer, or other programmable data processing apparatus. Controller 2230 serves to provide processing capabilities, such as storing, interpreting, and/or executing software instructions, as well as controlling the overall operation of the system. Controller 2230 may be configured and programmed to control data and/or power aspects of these devices. For example, in one aspect, with respect to droplet actuator 2205, controller 2230 controls droplet manipulation by activating/deactivating electrodes.

In one example, detector 2235 may be an imaging system that is positioned in relation to droplet actuator 2205. In one example, the imaging system may include one or more light-emitting diodes (LEDs) (e.g., an illumination source) and a digital image capture device, such as a charge-coupled device (CCD) camera. Detection can be carried out using an apparatus suited to a particular reagent or label in use. For example, an optical detector such as a fluorescence detector, absorbance detector, luminescence detector or the like can be used to detect appropriate optical labels. Systems designed for array-based detection are particularly useful. For example, optical systems for use with the methods set forth herein may be constructed to include various components and assemblies as described in Banerjee et al., U.S. Pat. No. 8,241,573, entitled "Systems and Devices for Sequence by Synthesis Analysis," issued on Aug. 14, 2012; Feng et al., U.S. Pat. No. 7,329,860, entitled "Confocal Imaging Methods and Apparatus," issued on Feb. 12, 2008; Feng et al., U.S. Pat. No. 8,039,817, entitled "Compensator for Multiple Surface Imaging," issued on Oct. 18, 2011; Feng et al., U.S. Patent Pub. No. 20090272914, entitled "Compensator for Multiple Surface Imaging," published on Nov. 5, 2009; and Reed et al., U.S. Patent Pub. No. 20120270305, entitled "Systems, Methods, and Apparatuses to Image a Sample for Biological or Chemical Analysis," published on Oct. 25, 2012, the entire disclosures of which are incorporated herein by reference. Such detection systems are particularly useful for nucleic acid sequencing embodiments.

Impedance sensing system 2240 may be any circuitry for detecting impedance at a specific electrode of droplet actuator 2205. In one example, impedance sensing system 2240 may be an impedance spectrometer. Impedance sensing system 2240 may be used to monitor the capacitive loading of any electrode, such as any droplet operations electrode, with or without a droplet thereon. For examples of suitable capacitance detection techniques, see Sturmer et al., International Patent Pub. No. WO/2008/101194, entitled "Capacitance Detection in a Droplet Actuator," published on Dec. 30, 2009; and Kale et al., International Patent Pub. No. WO/2002/080822, entitled "System and Method for Dispensing Liquids," published on Feb. 26, 2004, the entire disclosures of which are incorporated herein by reference.

Droplet actuator 2205 may include disruption device 2245. Disruption device 2245 may include any device that promotes disruption (lysis) of materials, such as tissues, cells and spores in a droplet actuator. Disruption device 2245 may, for example, be a sonication mechanism, a heating mechanism, a mechanical shearing mechanism, a bead beating mechanism, physical features incorporated into the droplet actuator 2205, an electric field generating mechanism, armal cycling mechanism, and any combinations thereof. Disruption device 2245 may be controlled by controller 2230.

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electro-magnetic, infrared, or semiconductor system, apparatus, device, or propagation medium. The computer readable medium may include transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed herein). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

Example 10

Indexed Library Preparation

Indexed multiplex PCR was performed with the OTMI buffer (Illumina Part#15059758), 161-plex SBS3-GS-F primer (gene specific forward) and GS-R primer (gene specific reverse) mix in betaine, universal forward primer (UF-4) with different indexes, universal reverse primer (UR) and human genomic DNA. Primer concentrations used were 10 nM each of GS-F and GS-R, 300 nM of UF-4, and 200 nM of UR primer in final PCR reaction. Coriell NA12878 genomic DNA was used at 0.02 ng/μL final as input for PCR. The DNA polymerase used was 0.04 U/μl Phusion HSII DNA polymerase (Thermo Fisher Scientific). The thermocycling parameters used in this experiment are shown in Table 4.

TABLE 4

| Parameters used in thermocycling reactions | |
|---|---|
| 98° C. | 2 min |
| 30 cycles | 98° C. 20" |
| | 70° C. 30" |
| | 60° C. . . . 60" (from 70° C. ramp to 60° C., 0.2° C./sec) |
| | 72° C. . . . 75" (from 60° C. ramp to 72° C., 0.2° C./sec) |
| 72° C. | 2 min |
| 10° C. | hold |

The resulting PCR product had adaptors on the ends that were complementary to the P7 and P5 primers used in Example 12 below.

Example 11

Preparation of Capture Beads for Ex-Amp Normalization

Streptavidin beads (Illumina Part#11118442) were washed with a buffer containing 5 mM Tris-HCl pH 7.5, 500 nM EDTA, and 1M NaCl (BW buffer) and re-suspended in 75 μl Biotin-P7-Index-SBS491' in BW-Buffer to a final concentration of 10 μM. The beads were vortexed for 15 min at room temperature, washed in 1×BW buffer and re-suspended in 37.5 or 0.25 nM each Capture Probe Template oligo, in HT1 buffer (as in MiSeq V3 150 cycle kit; Illumina catalog# MS-102-3001). The beads were incubated for 5 minutes at 60° C. followed by 5 minutes at 40° C., then washed and re-suspended in AMS-6 buffer (as in HiSeq PE Cluster Kit V4 for cBot (Illumina Catalog#PE-401-4001). After incubation at 40° C. for 5 minutes, the beads were re-suspended in 100 μL of 0.1N NaOH and incubated for additional 5 minutes at room temperature. The beads were then washed at least once in 100 μL HT1 buffer and re-suspended in 150 μL HT1 buffer. The resulting beads contained bound biotin-P7 amplification or normalization primer.

Example 12

On-bead Extension and Ex-Amp Normalization

Ten-fold serial dilutions of the indexed PCR product of Example 10 were prepared in 1×HT1 buffer and denatured in 20×SSC by heating at 98° C. for 3 minutes then keep on ice. Equal volume of capture beads of Example 11 was added to denatured PCR product and incubated at 75° C. for 30 sec, then at 65° C. for 10 min, then 40° C. for 5 min, followed by washing in PR2 buffer (in MiSeq V3 150 cycle kit, Illumina catalog# MS-102-3001).

On bead Ex-Amp normalization was performed as follows. Briefly, each sample was incubated at room temperature for 8 min with 1 μL of 100 μM P5 primer, 4 μL of H$_2$O and 5 μL of 0.1N NaOH. Prepared EPX mix following the manufacturer's recommendations (Illumina PN 15067046) and 35 μL of the EPX mix was added to 15 μL of the denatured P5 primer. PR2 buffer was removed from the beads (on magnet) and 50 μL of the EPX+P5 cocktail was added to the beads, and then re-suspended and incubated at 38° C. for 20 min followed by removal of supernatant. The libraries were denatured with 0.1N NaOH, washed and re-suspended in PR2 buffer.

Figure 29A:
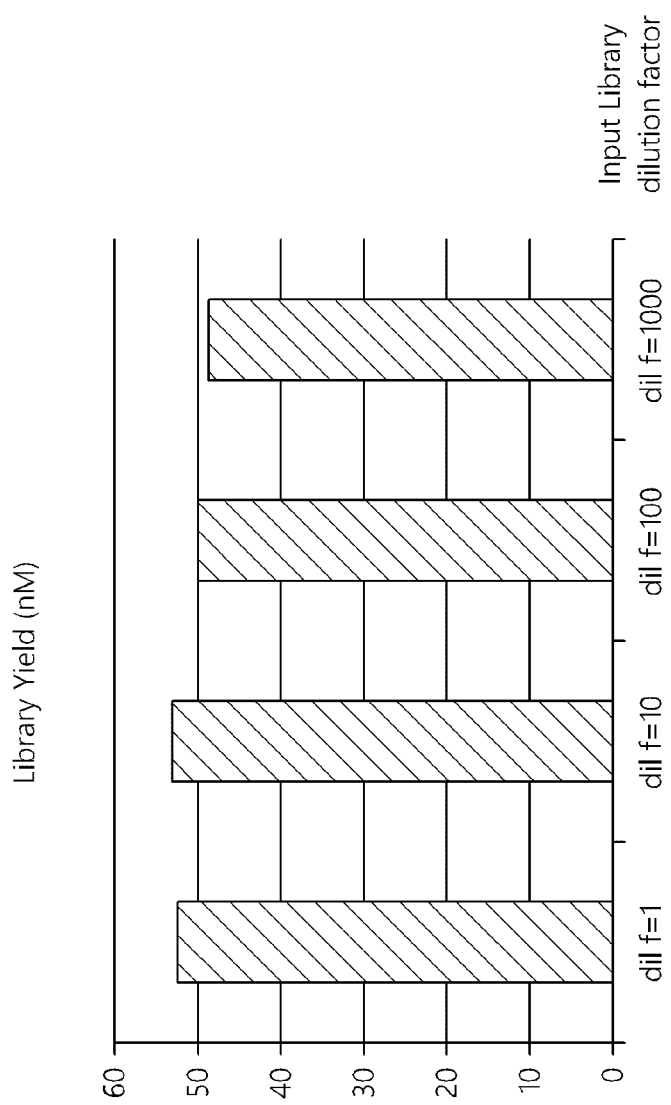
FIGS. 29A, 29B, and 29C graphically summarizes the results from experiments performed to illustrate a non-limiting example of a method of library normalization in accordance with some embodiments of the disclosure. 29A: Dilution factors in input nucleic acid libraries 29B: Library yields obtained from a standard library preparation procedure; 29C: Library yields obtained from a library preparation procedure that was performed according to a non-limiting example of a method of nucleic acid amplification and normalization of the disclosure.

The libraries were quantitated using SYBR Green qPCR library quantification kits (KAPA Biosystems, Part number KK4824). As shown in FIG. 29A, the output library yields were normalized regardless of the diverse input sample concentrations.

Example 13

High-throughput Sequencing (HiSeq)

Samples from Example 12 were normalized based on the reported qPCR yield. Total library concentration used was 10 pM. In this Example, normalized samples from Example 12 were sequenced on Illumina's HiSeq2000 using HiSeq V4 chemistry (Illumina Catalog numbers: PE-401-4001, FC-401-4002 and FC-401-4003), following standard single index settings as per manufacturer's recommendations. The top level sequencing metrics are shown in Table 5.

TABLE 5

Summary of sequencing metrics for individual nucleic acid samples whose DNA concentration have been normalized as described in Example 12.

| Sample Name | Total PF | On Target | Mean | Specificity | Uniformity | CV | Span95 |
|---|---|---|---|---|---|---|---|
| S1-30Cyc-Dil-1-ExAmp_S1 | 77760589 | 77169353 | 482308 | 0.992 | 0.90625 | 0.713 | 22 |
| S2-30Cyc-Dil-10-ExAmp_S2 | 78706859 | 78295323 | 489346 | 0.995 | 0.85 | 0.965 | 49 |
| S3-30Cyc-Dil-100-ExAmp_S3 | 75718469 | 75305133 | 470657 | 0.995 | 0.825 | 1.089 | 74 |
| S4-30Cyc-Dil-1000-ExAmp_S4 | 73640185 | 72479744 | 452998 | 0.984 | 0.8125 | 1.112 | 79 |

As shown in Table 5, it was observed that even with the aggressive dilution of the input PCR product, the library specificity remained high (>0.98). The uniformity dropped as expected with further dilution of the library however, even at 1000 fold diluted PCR product input, the uniformity is still at acceptable level (>0.80). Thus, as shown in Table 5, the sequencing metrics for the libraries of Example 12 resulting from the method described in the present disclosure are comparable to the standard library preparation method.

Example 14

On-bead Extension and Ex-Amp Normalization

Figure 29B:
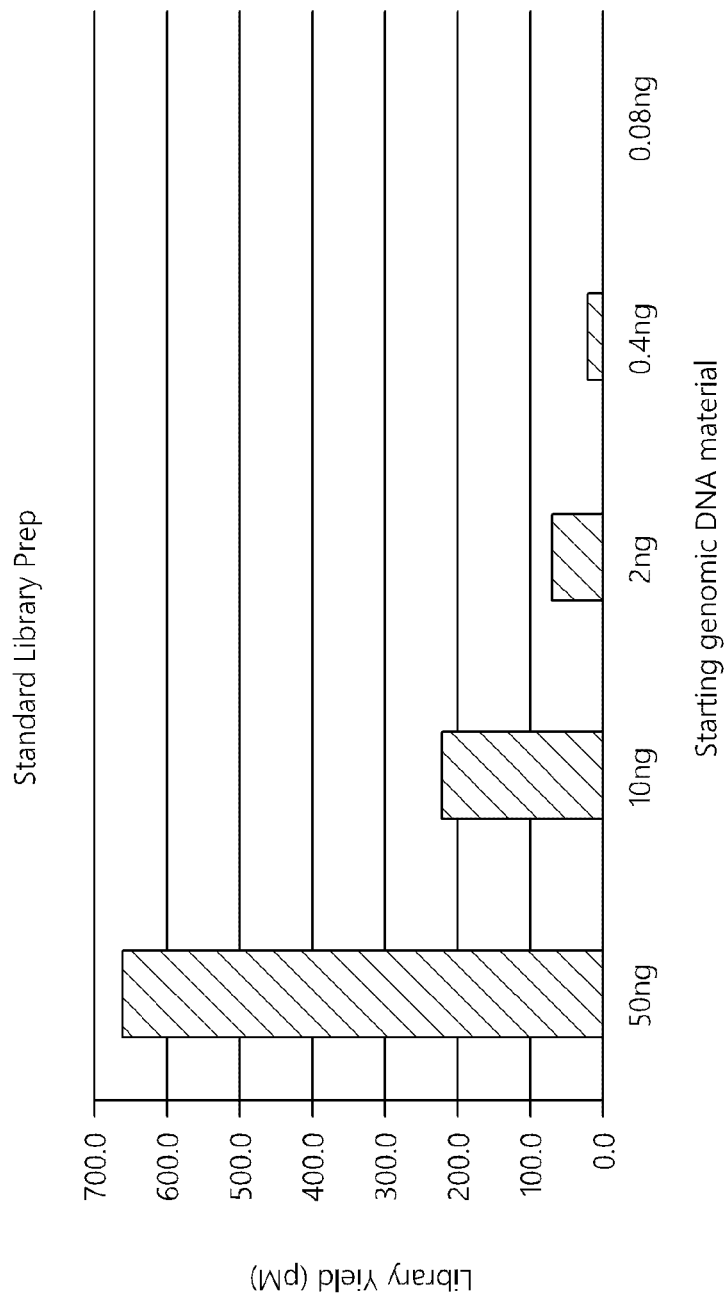
Figure 29C:
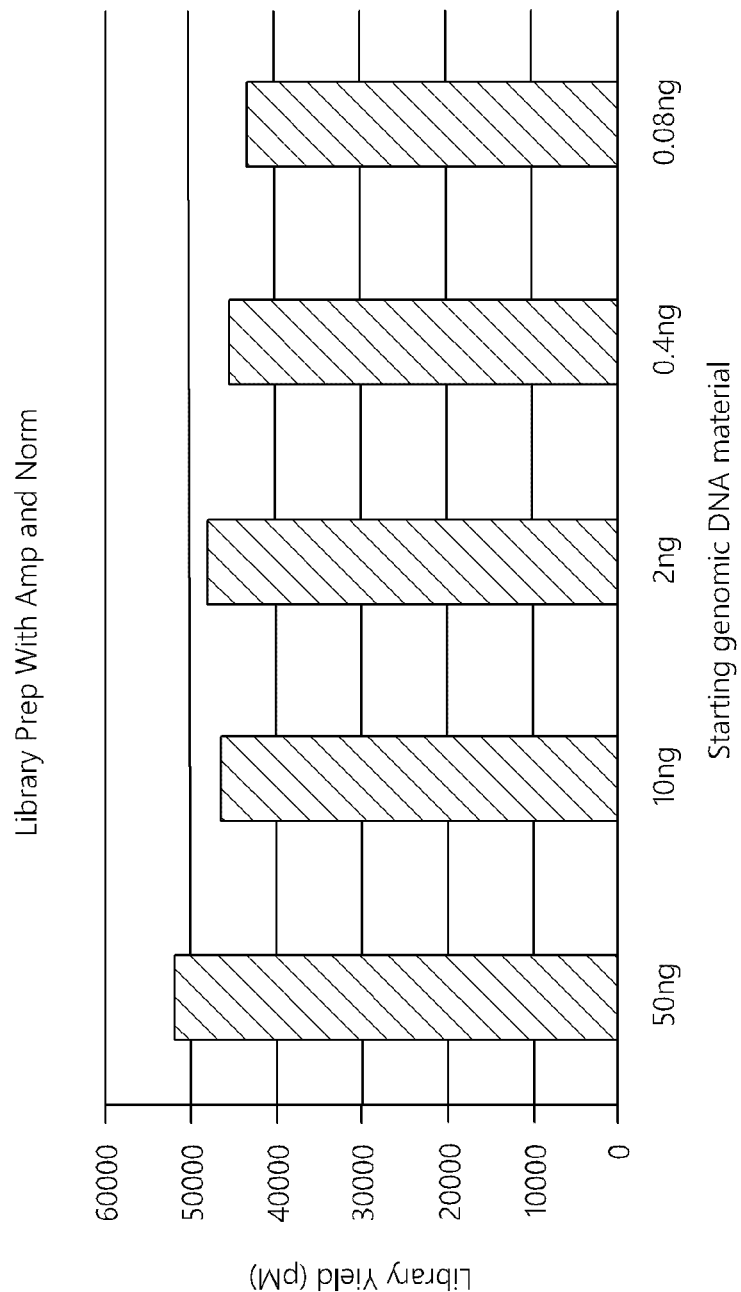

In another experiment, the experimental procedure outlined above in Example 12 was followed except that the template DNA used was genomic DNA from formalin-fixed paraffin-embedded (FFPE) samples (HorizonDX HD751). Input samples containing 50, 10, 2, 0.4 and 0.08 ng of genomic DNA was tested using the standard library prep protocol using TrueSeq library preparation kit (Illumina FC-121-4001) as per manufacturer's recommendations or using the method described in the present disclosure. The library yields were quantitated using KAPA library quantitation kit. The data shown in FIG. 29B was generated by using the standard library preparation method where the output library yields were approximately 659, 216, 67, 18 and 5.3 pM for the input DNA range 50, 10, 2, 0.4 and 0.08 ng respectively. In comparison, using the method described in the present disclosure, the output library yields were consistent across the input range resulting in approximately 51500, 46250, 47628, 45220 and 43238 pM, respectively, as shown in FIG. 29C.

Example 15

On-bead Extension and Ex-Amp Normalization

In this Example, the samples were normalized based on the reported qPCR yield. The yield from the standard library preparation using 0.4 ng and 0.08 ng of DNA, (samples S05 and S06 in the table below) were too low to be normalized. Total normalized library concentration was 20 pM. The libraries were sequenced on Illumina's MiSeq sequencer using MiSeq V3 150 cycle kit (Illumina Catalog# MS-102-3001), following standard dual index settings. The top level sequencing metrics are given in Table 6. Samples S02-S06 are the standard library preparations shown in FIG. 29B, while S08-S012 are the samples from FIG. 29C. Samples S01 and S07 are controls.

TABLE 6

Summary of sequencing metrics for individual nucleic acid samples whose DNA concentrations have been normalized as described in Example14.

| Sample Name | Total PF | On Target | Mean | Specificity | Uniformity | CV | Span95 |
|---|---|---|---|---|---|---|---|
| S01-AXE-NTC_S1 | 75263 | 22117 | 138 | 0.294 | 0.388 | 6.699 | 462 |
| S02-AXE-50ngHD751_S2 | 4622638 | 4590000 | 28688 | 0.993 | 0.906 | 0.905 | 26 |
| S03-AXE-10ngHD751_S3 | 5624965 | 5592099 | 34951 | 0.994 | 0.844 | 0.99 | 49 |
| S04-AXE-2ngHD751_S4 | 4387777 | 4359280 | 27246 | 0.994 | 0.756 | 1.286 | 138 |
| S05-AXE-o4ngHD751_S5 | 2890741 | 2854572 | 17841 | 0.987 | 0.681 | 1.471 | 604 |
| S06-AXE-o08ngHD751_S6 | 615260 | 593796 | 3711 | 0.965 | 0.544 | 1.699 | inf |
| S07-ExAmp-NTC_S7 | 1215577 | 422982 | 2644 | 0.348 | 0.031 | 8.812 | 435 |
| S08-ExAmp-S0ngHD751_S8 | 4042970 | 4009345 | 25058 | 0.992 | 0.863 | 1.031 | 38 |
| S09-ExAmp-10ngHD751_S9 | 3993705 | 3967177 | 24795 | 0.993 | 0.794 | 1.132 | 70 |
| S10-ExAmp-2ngHD751_S10 | 3897994 | 3869129 | 24182 | 0.993 | 0.688 | 1.449 | 210 |
| S11-ExAmp-o4ngHD751_S11 | 3825284 | 3787323 | 23671 | 0.99 | 0.65 | 1.689 | 833 |

TABLE 6-continued

Summary of sequencing metrics for individual nucleic acid samples whose DNA concentrations have been normalized as described in Example14.

| Sample Name | Total PF | On Target | Mean | Specificity | Uniformity | CV | Span95 |
|---|---|---|---|---|---|---|---|
| S12-ExAmp-o08ngHD751_S12 | 3284845 | 3177453 | 19859 | 0.967 | 0.512 | 1.829 | 200862 |

As shown in Table 6, the sequencing metrics for the libraries resulting from the amplification and normalization method described in the present disclosure (S08-S12) are comparable to the standard library preparation method (S02-S06).

Thus, as FIGS. 29A and 29C demonstrate, the amplification and normalization methods disclosed herein provide a simple method of providing a normalized amount of output DNA libraries across a wide range of concentrations of input DNA samples, where no further dilution or concentration of the resulting output libraries is required before pooling the libraries for subsequent sequencing. In particular, the experimental data presented in Tables 5 and 6 show that the quality of the amplified product is comparable to existing library preparation methods across a wide range of input DNA concentrations.

All of the references disclosed herein, including but not limited to journal articles, textbooks, patents and patent applications, are hereby incorporated by reference for the subject matter discussed herein and in their entireties. Throughout this disclosure, various information sources are referred to and incorporated by reference. The information sources include, for example, scientific journal articles, patent documents, textbooks, and World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use the embodiments disclosed herein, any discussion and comment in a specific information source should no way be considered as an admission that such comment was widely accepted as the general opinion in the field.

What is claimed is:

1. A method for normalizing a plurality of nucleic acid amplification reactions comprising:
    performing a first and second normalized amplifications, wherein the first normalized amplification comprises:
    a) providing an input sample comprising target nucleic acids;
    b) contacting the input sample with a reaction mixture comprising a plurality of first amplification primers and a plurality of second amplification primers, wherein:
        i. the plurality of first amplification primers is immobilized on a solid support, the first amplification primers being capable of specifically hybridizing to a first sequence of the target nucleic acids, wherein the plurality of first amplification primers is provided in an amount which limits the yield of amplification products comprising the first amplification primers, wherein the amount of the first amplification primers is substantially the same in the first and second normalized amplifications, and
        ii. the plurality of second amplification primers is in solution, the plurality of second primers being capable of specifically hybridizing to a second sequence of the target nucleic acids, wherein the plurality of second amplification primers is provided in an amount that exceeds the amount of the first amplification primers;
    c) amplifying the target nucleic acids under isothermal conditions, wherein amplification reagents except the first amplification primers are provided in excess amounts such that substantially all of the first amplification primers are incorporated into amplification products, thereby normalizing the amplification reaction to the amount of the first amplification primers; and
    performing the second normalized amplification, comprising: repeating (a)-(c) with a different input sample, thereby obtaining an amount of first amplification products comprising first amplification primers from a first normalized amplification which is substantially the same as an amount of second amplification products comprising first amplification primers from a second normalized amplification.

2. The method of claim 1, wherein the plurality of first amplification primers is hybridized with the target nucleic acids prior to being immobilized on the solid support.

3. The method of claim 1, wherein the plurality of first amplification primers is immobilized on the solid support prior to being hybridized with the target nucleic acids.

4. The method of claim 1, wherein the solid support comprises a plurality of beads.

5. The method of claim 1, wherein the solid support is a surface of a reaction site.

6. The method of claim 1, wherein at least one of the first amplification primers and/or the second amplification primers comprises a region having sequence complementarity to known nucleotide sequences within the target nucleic acids.

7. The method of claim 6, wherein the known nucleotide sequences correspond to a first end or a second end of the target nucleic acids.

8. The method of claim 7, wherein the first end or the second end of the target nucleic acids comprises a universal primer region that has been added to the target nucleic acids.

9. The method of claim 8, wherein the universal primer region comprises a sequencing-by-synthesis (SBS) primer sequence.

10. The method of claim 9, wherein at least one of the first and/or second amplification primers further comprises an indexing portion.

11. The method of claim 8, wherein at least one of the first and/or second amplification primers further comprises a region having sequence complementarity to the universal primer region added to the target nucleic acids.

12. The method of claim 1, wherein at least a portion of the first amplification primers further comprises a capture portion having sequence complementarity to a cognate region of the target nucleic acids in addition of a known sequence of the target nucleic acids.

13. The method of claim 1, wherein prior to step (a), the target nucleic acids in the input sample are subjected to a first enrichment amplification reaction comprising a first target-specific primer and a second target-specific primer.

14. The method of claim 13, wherein each of the first target-specific primer and the second target-specific primer comprises a region having sequence complementarity to known sequences of the target nucleic acids.

15. The method of claim 13, wherein each of the first target-specific primer and the second target-specific primer further comprises a universal primer region.

16. The method of claim 15, wherein the universal primer region of the first target-specific primer or the second target-specific primer comprises a sequencing-by-synthesis (SBS) primer sequence.

17. The method of claim 13, wherein prior to step (a), the target nucleic acids in the input sample are further subjected to a second enrichment amplification reaction comprising a first universal primer and a second universal primer, wherein:
   a) the first universal primer comprises a region having sequence complementarity to the universal primer region of the first target-specific primer; and
   b) the second universal primer comprises a region having sequence complementarity to the universal primer region of the second target-specific primer.

18. The method of claim 17, wherein at least one of the first and/or second universal primers further comprises an indexing portion.

19. The method of claim 1, wherein the method is performed in multiplexed format using a droplet actuator.

20. A method for normalizing multiplexed amplification of target nucleic acids on a droplet actuator, comprising:
   a) providing a plurality of input samples comprising target nucleic acids;
   b) loading the plurality of input samples onto a droplet operations surface of the droplet actuator having droplet operations electrodes arranged thereon;
   c) dispensing a normalization reagent droplet to each of the loaded input samples to obtain a plurality of reaction droplets, wherein the normalization reagent droplet comprises a plurality of first amplification primers and a plurality of second amplification primers, wherein:
      i. the plurality of first amplification primers is immobilized on a solid support, the first amplification primers being capable of specifically hybridizing to a first sequence of the target nucleic acids, wherein the plurality of first amplification primers is provided in an amount which limits the yield of amplification products comprising the first amplification primers, wherein the amount of the first amplification primers is substantially the same in each normalization reagent droplet; and
      ii. the plurality of second amplification primers is in solution, the plurality of second primers being capable of specifically hybridizing to a second sequence of the target nucleic acids, wherein the plurality of second amplification primers is provided in an amount that exceeds the amount of the first amplification primers;
   d) amplifying the target nucleic acids of the reaction droplets under isothermal conditions, wherein amplification reagents except the first amplification primers are provided in excess amounts such that substantially all of the first amplification primers are incorporated into amplification products, thereby obtaining a plurality of output samples each comprising substantially the same amount of amplified target nucleic acids, and thereby normalizing the multiplexed amplification to the amount of the first amplification primers.

21. The method of claim 20, wherein prior to step (c) further comprising:
   dispensing a first enrichment PCR reagent droplet onto a droplet operations surface of the droplet actuator, wherein the first enrichment PCR reagent droplet comprising a first target-specific primer and a second target-specific primer;
   dispensing a second enrichment PCR reagent droplet onto a droplet operations surface of the droplet actuator, wherein the second enrichment PCR reagent droplet comprising a first universal primer and a second universal primer;
   combining the second enrichment PCR reagent droplet with the first enrichment PCR reagent droplet using droplet operations to form a combined enrichment PCR reagent droplet; and
   thermally cycling the target nucleic acids in the plurality of input samples to form enriched nucleic acid samples.

22. The method of claim 1, wherein the plurality of second amplification primers is provided in an amount that exceeds the amount of the first amplification primers by at least about 100%.

23. The method of claim 20, wherein the plurality of second amplification primers is provided in an amount that exceeds the amount of the first amplification primers by at least about 100%.

24. A method for normalizing a plurality of nucleic acid amplification reactions comprising:
   providing a first set of target nucleic acids;
   performing a first amplification reaction, comprising:
      a) providing first amplification primers which bind to a first sequence of the target nucleic acids, are immobilized on a solid support, and are provided in an amount which limits the yield of amplification products, and
      b) providing second amplification primers which bind to a second sequence of the target nucleic acid, are in solution, and are provided in an amount that exceeds the amount of the first amplification primers; and
      c) amplifying the target nucleic acids with the first and second amplification primers under isothermal conditions such that substantially all of the first amplification primers are incorporated into amplification products to yield a first limited amount of amplification products; and
   performing a second amplification reaction by repeating steps (a)-(c) with a second, different, target nucleic acid sample, thereby obtaining a second limited amount of amplification products that is substantially the same as the first limited amount of amplification products.

* * * * *